United States Patent
Towner et al.

(10) Patent No.: US 12,415,851 B2
(45) Date of Patent: Sep. 16, 2025

(54) MONOCLONAL ANTIBODIES TO ELTD1 AND USES THEREOF

(71) Applicants: Oklahoma Medical Research Foundation, Oklahoma City, OK (US); Seoul National University R&DB Foundation, Seoul (KR)

(72) Inventors: Rheal A. Towner, Piedmont, OK (US); Junho Chung, Seoul (KR)

(73) Assignees: Oklahoma Medical Research Foundation, Oklahoma City, OK (US); Seoul National University R&DB Foundation, Seoul (KR)

( * ) Notice: Subject to any disclaimer, the term of this patent is extended or adjusted under 35 U.S.C. 154(b) by 999 days.

(21) Appl. No.: 17/290,501

(22) PCT Filed: Nov. 1, 2019

(86) PCT No.: PCT/US2019/059488
§ 371 (c)(1),
(2) Date: Apr. 30, 2021

(87) PCT Pub. No.: WO2020/092969
PCT Pub. Date: May 7, 2020

(65) Prior Publication Data
US 2022/0195024 A1    Jun. 23, 2022

Related U.S. Application Data

(60) Provisional application No. 62/754,684, filed on Nov. 2, 2018.

(51) Int. Cl.
| | |
|---|---|
| C07K 16/22 | (2006.01) |
| A61K 39/00 | (2006.01) |
| A61K 39/395 | (2006.01) |
| A61K 45/06 | (2006.01) |
| A61P 35/00 | (2006.01) |
| C07K 16/06 | (2006.01) |
| C07K 16/28 | (2006.01) |
| G01N 33/574 | (2006.01) |

(52) U.S. Cl.
CPC .......... *C07K 16/22* (2013.01); *A61K 39/3955* (2013.01); *A61K 45/06* (2013.01); *A61P 35/00* (2018.01); *C07K 16/2869* (2013.01); *G01N 33/57492* (2013.01); *A61K 39/395* (2013.01); *A61K 39/39516* (2013.01); *A61K 2039/505* (2013.01); *C07K 16/06* (2013.01); *C07K 2317/31* (2013.01); *C07K 2317/35* (2013.01); *C07K 2317/565* (2013.01); *C07K 2317/622* (2013.01); *C07K 2317/76* (2013.01); *C07K 2317/92* (2013.01); *G01N 2333/726* (2013.01)

(58) Field of Classification Search
None
See application file for complete search history.

(56) References Cited

U.S. PATENT DOCUMENTS

| | | | |
|---|---|---|---|
| 4,472,509 | A | 9/1984 | Gansow et al. |
| 4,938,948 | A | 7/1990 | Ring et al. |
| 5,021,236 | A | 6/1991 | Gries et al. |
| 2012/0128632 | A1 | 5/2012 | Teumer et al. |
| 2016/0143997 | A1 | 5/2016 | Teague et al. |
| 2017/0008969 | A1* | 1/2017 | Towner ............... C12Q 1/6886 |

FOREIGN PATENT DOCUMENTS

| | | |
|---|---|---|
| WO | 2016028141 A1 | 2/2016 |
| WO | 2017055327 A1 | 4/2017 |
| WO | 2020092969 A1 | 5/2020 |
| WO | 2020092969 A8 | 5/2020 |

OTHER PUBLICATIONS

Edwards et al. J. Mol. Biol. 2003. 334: 103-118 (Year: 2003).*
Lloyd et al. Protein Engineering, Design & Selection. 2009. 22(3): 159â168 (Year: 2009).*
Meyer et al. British Journal of Haematology. 2018. 180: 808â820 (Year: 2018).*
Vajdos et al. J Mol Biol. 2002. 320: 415-428 (Year: 2003).*
Zalles et al. J Cell Mol Med. Dec. 14, 2021. 26: 570-582 (Year: 2021).*
Ziegler. Dissertation. May 11, 2018. University of Oklahoma. (Year: 2018).*
Fang et al. Nature Biotech. Apr. 17, 2005. 23(5): 584-590 (Year: 2005).*
Zalles, M., "ID: 461 In Vivo Detection of ELTD1, a Biomarker for Angiogensis, using Molecular-Targeted MRI in a Mouse G55 Xenograft Model for GBM," Proceedings of the World Molecular Imaging Congress 2018, Sep. 12-15, 2018: General Abstracts, Molecular Imaging and Biology 20, 1-584, Abstract only.
International Search Report and Written Opinion of USPTO for PCT/US2019/059488 dated Feb. 21, 2020, 13 pp.
Poellinger L, et al., "Modulating Notch signaling by pathway-intrinsic and pathway-extrinsic mechanisms," Curr Opin Genet Dev Sep. 2008; 18: 449-454.
Razpotnik R, et al., "Targeting Malignant Brain Tumors with Antibodies," Front Immunol. Sep. 25, 2017; 8: 1181, 1-14.
Reichert JM, et al., "Monoclonal antibody successes in the clinic," Nat Biotechnol. Sep. 2005; vol. 23, No. 9, 1073-1078.
Serban F, et al., "Silencing of epidermal growth factor, latrophilin and seven transmembrane domain-containing protein 1 (ELTD1) via siRNA-induced cell death in glioblastoma," J Immunoassay Immunochem. Sep. 2017; vol. 38, No. 1, 21-33.
Stupp R, et al., "Radiotherapy plus concomitant and adjuvant temozolomide for glioblastoma," N Engl J Med Mar. 10, 2005; 352:10, pp. 987-996.

(Continued)

Primary Examiner — Daniel E Kolker
Assistant Examiner — Brianna K Swartwout
(74) Attorney, Agent, or Firm — Edwin S. Flores; Daniel J. Chalker; Chalker Flores, LLP

(57) ABSTRACT

The present disclosure is directed to novel monoclonal antibodies that bind to ELTD 1 and methods for use thereof, including, detection and treatment of cancer, multiple sclerosis, retinopathy, or promoting tissue regeneration.

12 Claims, 30 Drawing Sheets

Specification includes a Sequence Listing.

(56) References Cited

OTHER PUBLICATIONS

Suhardja A, et al., "Role of growth factors and their receptors in proliferation of microvascular endothelial cells," Microsc Res Tech. 2003; 60: 70-75.
Tamimi AF, et al., Epidemiology and Outcome of Glioblastoma. In: De Vleeschouwer S, editor, "Glioblastoma," Codon Publications, Brisbane (AU), Sep. 2017.
Thakkar JP, et al., "Epidemiologic and molecular prognostic review of glioblastoma," Cancer Epidemiol Biomarkers Prev. Jul. 22, 2014; 23: 1985-1996.
Torre D, et al., "BioJupies: Automated Generation of Interactive Notebooks for RNA-Seq Data Analysis in the Cloud," Cell Syst. Nov. 28, 2018; 7(5) 556-561 e3.
Towner RA, et al., "In vivo detection of inducible nitric oxide synthase in rodent gliomas," Free Radic Biol Med. 2010; 48: 691-703.
Towner RA, et al., "ELTD1, a potential new biomarker for gliomas," Neurosurgery, Jan. 2013; 72(1) 77-91.
Varley KE, et al., "Recurrent read-through fusion transcripts in breast cancer," Breast Cancer Res Treat. Jun. 15, 2014; 146: 287-97.
Van Tellingen, et al., "Overcoming the blood-brain tumor barrier for effective glioblastoma treatment," Drug Resist Updat Feb. 2015; 19: 1-12.
Wang J, et al., "CD133 negative glioma cells form tumors in nude rats and give rise to CD133 positive cells," Int J Cancer. 2008; 122: 761-768.
Wei LC, et al., "Nestin small interfering RNA (siRNA) reduces cell growth in cultured astrocytoma cells," Brain Res. 2008; 1196: 103-12.
Wen PY, et al., "Malignant gliomas in adults," N Engl J Med Jul. 31, 2008; 359: 492-507.
Wren JD, et al., "Knowledge discovery by automated identification and ranking of implicit relationships," Bioinformatics. Jan. 22, 2004; vol. 20, No. 3, 389-398.
Wren JD, "A global meta-analysis of microarray expression data to predict unknown gene functions and estimate the literature-data divide," Bioinformatics. May 15, 2009; vol. 25, No. 13, 1694-1701.
Xing D, et al., "Expression of neonatal Nav1.5 in human brain astrocytoma and its effect on proliferation, invasion and apoptosis of astrocytoma cells," Oncol Rep. Mar. 28, 2014; 31: 2692-2700.
Yang L, et al., "Single chain epidermal growth factor receptor antibody conjugated nanoparticles for in vivo tumor targeting and imaging," Small Feb. 2009; 5(2), 235-243.
Yang X, et al., The correlation of bone morphogenetic protein 2 with poor prognosis in glioma patients. Tumour Biol. Aug. 7, 2014; 35: 11091-11095.
Yuan J, et al., "CHST9 rs1436904 genetic variant contributes to prognosis of triple-negative breast cancer," Sci Rep. Sep. 18, 2017; 7: 11802, 1-8.
Zeng J, et al., "Identification of the role of TRPM8 in glioblastoma and its effect on proliferation, apoptosis and invasion of the U251 human glioblastoma cell line," Oncol Rep. Jul. 2019, vol. 42, 1517-1526.
Zhang Y, et al., "Association between polymorphisms in COMT, PLCH1, and CYP17A1, and non-small-cell lung cancer risk in Chinese nonsmokers," Clin Lung Cancer. 2013; vol. 14, No. 1 pp. 45-49.
Zhao C, et al., "SCUBE3 overexpression predicts poor prognosis in non-small cell lung cancer," Biosci Trends. 2013; 7(6) 264-269.
Zhu W, et al., "Heterogeneity of tumor vasculature and antiangiogenic intervention: insights from MR angiography and DCE-MRI," PLoS One Jan. 23, 2014; vol. 9, Iss. 1, e86583, 1-7.
Zhu X, et al., "Identification of internalizing human single-chain antibodies targeting brain tumor sphere cells," Mol Cancer Ther Jul. 2010; 9(7) 2131-2141.
Zhuo H, et al., "Tumor endothelial cell-derived cadherin-2 promotes angiogenesis and has prognostic significance for lung adenocarcinoma," Mol Cancer. 2019; 18: 34, 107.

Ziegler J, et al., "ELTD1, an effective anti-angiogenic target for gliomas: preclinical assessment in mouse GL261 and human G55 xenograft glioma models," Neuro Oncol 2017; 19(2) 175-185.
Ziegler J, et al., Targeting ELTD1, an angiogenesis marker for glioblastoma (GBM), also affects VEGFR2: molecular-targeted MRI assessment. Am J Nucl Med Mol Imaging. 2019; 9: 93-109.
Zou Q, et al., "Survey of the translation shifts in hepatocellular carcinoma with ribosome profiling," Theranostics. vol. 9, Iss. 14, May 31, 2019; 4141-4155.
Dieterich, et al., "Transcriptional profiling of human glioblastoma vessels indicates a key role of VEGF-A and TGFB2 in vascular abnormalization," Journal of Pathology, Aug. 31, 2023, vol. 228, pp. 378-390.
Dieterich LC, "Transcriptional profiling of human glioblastoma vessels indicates a key role of VEGF-A and TGFbeta2 in vascular abnormalization," J Pathol. Aug. 31, 2012; 228: 378-90.
Supplemental Partial European Search Report for 19879054.5 dated Jun. 30, 2022, 17 pp.
"Proceedings of the World Molecular Imaging Congress 2018" Seattle, Washington, Sep. 12-15, 2018, General Abstracts, Molecular Imaging & Biology, Elsevier Boston, vol. 20, No. 1, Sep. 12, 2018, 584 pp.
Ziegler, J. et al., "ELTD1, an effective anti-angiogenic target for gliomas: preclinical assessment in mouse GL261 and human G55 Xenograft Glioma models," Neuro-Oncology, Jul. 14, 2016, pp. 175-185.
Alves TR, "Glioblastoma cells: a heterogeneous and fatal tumor interacting with the parenchyma," Life Sci. Apr. 27, 2011; 89: 532-9.
Andris-Widhopf J, et al., "Methods for the generation of chicken monoclonal antibody fragments by phage display" J Immunol Methods, May 17, 2000; 242: pp. 159-181.
Bao S, et al., "Targeting cancer stem cells through L1CAM suppresses glioma growth," Cancer Res. Aug. 1, 2008; 68: 6043-6048.
Beal K, et al., "Antiangiogenic agents in the treatment of recurrent or newly diagnosed glioblastoma: analysis of single-agent and combined modality approaches," Radiat Oncol. 2011; 6:2, pp. 1-15.
Boussif, O, et al., "A versatile vector for gene and oligonucleotide transfer into cells in culture and in vivo: polyethylenimine" Proc Natl Acad Sci U S A, Feb. 25, 1995; 92: 7297-7301.
Brescia P, et al., "CD133 is essential for glioblastoma stem cell maintenance," Stem Cells. Jan. 10, 2013; 31: 857-69.
Buss, NA, et al., "Monoclonal antibody therapeutics: history and future," Curr Opin Pharmacol, Aug. 2012; 12: 615-622.
Cai Y, et al., "Downregulation of microRNA-645 suppresses breast cancer cell metastasis via targeting DCDC2," Eur Rev Med Pharmacol Sci. 2017; 21: 4129-4136.
Chang PM, et al., "High expression of CHRNA1 is associated with reduced survival in early stage lung adenocarcinoma after complete resection," Ann Surg Oncol. Jun. 18, 2013; 20: 3648-3654.
Chen EY, et al., "Enrichr: interactive and collaborative HTML5 gene list enrichment analysis tool," BMC Bioinformatics. 2013; 14:128, pp. 1-14.
Chinot OL, et al., "Bevacizumab plus radiotherapy-temozolomide for newly diagnosed glioblastoma," N Engl J Med Feb. 20, 2014; 370: 709-722.
Dafni H, et al., "MRI and fluorescence microscopy of the acute vascular response to VEGF165: vasodilation, hyper-permeability and lymphatic uptake, followed by rapid inactivation of the growth factor," NMR Biomed 2002; 15: 120-131.
Dai S, et al., "MicroRNA-139-5p acts as a tumor suppressor by targeting ELTD1 and regulating cell cycle in glioblastoma multiforme," Biochem Biophys Res Commun. Oct. 2015; 467: 204-210.
Das S, et al. "Angiogenesis in glioblastoma," N Engl J Med, Oct. 17, 2013; 369: 1561-1563.
Dolecek TA, et al., "CBTRUS statistical report: primary brain and central nervous system tumors diagnosed in the United States in 2005-2009," Neuro Oncol. 2012; 14 Suppl 5: v1-v49.
Ewels P, "MultiQC: summarize analysis results for multiple tools and samples in a single report" Bioinformatics. 2016; 32(19), pp. 3047-3048.
Farrell CJ, "Genetic causes of brain tumors: neurofibromatosis, tuberous sclerosis, von Hippel-Lindau, and other syndromes," Neurol Clin 2007; 25: 925-946.

(56) References Cited

OTHER PUBLICATIONS

Friedman HS, et al., "Bevacizumab alone and in combination with irinotecan in recurrent glioblastoma," J Clin Oncol Oct. 1, 2009; 27: 4733-4740.
Furnari FB, et al., "Malignant astrocytic glioma: genetics, biology, and paths to treatment," Genes Dev. 2007; 21: 2683-2710.
Genentech, Inc., Avastin Prescribing Information, Rev. Jan. 2021.
Ghiaseddin A, "Use of bevacizumab in recurrent glioblastoma," CNS Oncol. 2015; 4(3) 157-169.
Guo M, "miR-656 inhibits glioma tumorigenesis through repression of BMPR1A," Carcinogenesis, Jan. 30, 2014; 35, No. 8, pp. 1698-1706.
Han J, "A phosphorylation pattern-recognizing antibody specifically reacts to RNA polymerase II bound to exons," Exp Mol Med 2016; 48: e271, pp. 1-7.
Hermanson G, Chapter 3, "Zero-Length Cross-linkers," Bioconjugate techniques: New York: Academic Press; 1996, 53 pp.
Huang J, "Adenosine deaminase and adenosine kinase expression in human glioma and their correlation with gliomaassociated epilepsy," Mol Med Rep. Aug. 5, 2015; 12: 6509-6516.
Ishiwata T, "Neuroepithelial stem cell marker nestin regulates the migration, invasion and growth of human gliomas," Oncol Rep. Mar. 29, 2011; 26: 91-99.
Iwadate Y, "Transforming growth factor-beta and stem cell markers are highly expressed around necrotic areas in glioblastoma," J Neurooncol. May 18, 2016; 129: 101-107.
Izumoto S, "Gene expression of neural cell adhesion molecule L1 in malignant gliomas and biological significance of L1 in glioma invasion," Cancer Res. Mar. 15, 1996; 56: 1440-1444.
Jensen RL, "Preoperative dynamic contrast-enhanced MRI correlates with molecular markers of hypoxia and vascularity in specific areas of intratumoral microenvironment and is predictive of patient outcome," Neuro Oncol 2014; 16: 280-291.
Jin X, "Cell surface Nestin is a biomarker for glioma stem cells," Biochem Biophys Res Commun. Mar. 21, 2013; 433: 496-501.
Karpel-Massler G, et al., "Therapeutic inhibition of the epidermal growth factor receptor in high-grade gliomas: where do we stand?" Mol Cancer Res Jul. 7, 2009; 7: 1000-1012.
Kiefel H, et al., "L1CAM: a major driver for tumor cell invasion and motility" Cell Adh Migr. Jul./Aug. 2012; 6: 374-384.
Kitange GJ, et al., "Induction of MGMT expression is associated with temozolomide resistance in glioblastoma xenografts," Neuro Oncol Jun. 2009; 11: 281-291.
Kreisl TN, et al., "Phase II trial of single-agent bevacizumab followed by bevacizumab plus irinotecan at tumor progression in recurrent glioblastoma," J Clin Oncol Feb. 10, 2009; 27:5, pp. 740-745.
Kuan CT, et al., "Recombinant single-chain variable fragment antibodies against extracellular epitopes of human multidrug resistance protein MRP3 for targeting malignant gliomas," Int J Cancer Aug. 1, 2010; 127: 598-611.
Lariviere M, et al., "Multimodal molecular imaging of atherosclerosis: Nanoparticles functionalized with scFv fragments of an anti-alphaIIbbeta3 antibody," Nanomedicine Jun. 4, 2019; 22: 102082, 12 pp.
Lee CY, "Strategies of temozolomide in future glioblastoma treatment," Onco Targets Ther, Jan. 9, 2017; 10: 265-270.
Lee JW, et al., "MicroRNA-708-3p mediates metastasis and chemoresistance through inhibition of epithelial-to-mesenchymal transition in breast cancer," Cancer Sci. Mar. 2, 2018; 109: 1404-1413.
Love MI, et al., "Moderated estimation of fold change and dispersion for RNA-seq data with DESeq2," Genome Biol. 2014; 15: 550, 1-21.
Lu Z, et al., "Generation of a Fully Human scFv that binds Tumor-Specific Glycoforms," Sci Rep Mar. 25, 2019; 9: 5101.
Masiero M, et al., "A core human primary tumor angiogenesis signature identifies the endothelial orphan receptor ELTD1 as a key regulator of angiogenesis," Cancer Cell, Aug. 12, 2013; 24: 229-241.
Matsuda Y, et al., "Nestin is a novel target for suppressing pancreatic cancer cell migration, invasion and metastasis," Cancer Biol Ther. Mar. 1, 2011; 11: 512-523.
Mazzocco C, et al., "In vivo imaging of prostate cancer using an anti-PSMA scFv fragment as a probe," Sci Rep Mar. 4, 2016; 6: 23314, 1-10.
Miller AC, et al., "Cis-Inhibition of Notch by endogenous Delta biases the outcome of lateral inhibition," Curr Biol Aug. 25, 2009; 19(16) 1378-1383.
Nechiporuk T, et al., "ETL, a novel seven-transmembrane receptor that is developmentally regulated in the heart. ETL is a member of the secretin family and belongs to the epidermal growth factor-seven-transmembrane subfamily" J Biol Chem Feb. 9, 2001; vol. 276, No. 6, pp. 4150-4157.
Ohgaki H, et al., "Genetic pathways to glioblastoma: a population-based study," Cancer Res Oct. 1, 2004; 64: 6892-6899.
Olar A, et al., "Using the molecular classification of glioblastoma to inform personalized treatment," J Pathol. Jan. 2014; 232(2), 165-177.
Patil SS, "Novel anti IGFBP2 single chain variable fragment inhibits glioma cell migration and invasion," J Neurooncol Apr. 20, 2015; 123: 225-235.
Lee, Y., et al., "An antibody reactive to the Gly63-Lys68 epitope of NT-proBNP exhibits O-glycosylation-independent binding," Exp. & Mol. Med. Jul. 2014, vol. 46, e114, 1-9.

* cited by examiner

UNTREATED pAb mAb

1. DEVELOPMENTAL GENES
2. NESTIN-RELATED
3. CELL PROLIFERATION/ANGIOGENESIS
4. ASTROCYTE/MICROGLIA INFLAMMATION

SEQUENCE LISTING

<160> NUMBER OF SEQ ID NOS: 132

<210> SEQ ID NO 1
<211> LENGTH: 756
<212> TYPE: DNA
<213> ORGANISM: Artificial Sequence
<220> FEATURE:
<223> OTHER INFORMATION: Synthetic primer

<400> SEQUENCE: 1

```
gccctgactc agccgtcctc ggtgtcagca aacccgggag aaaccgtcaa gatcacctgc      60
tccgggagta gtggcagcta ctatggctgg caccagcaga gtctcctgg cagtgcccct      120 gtcactctga tctatgacaa caccaacaga ccctcggaca tcccttcacg attcttcggt      180
tccaaatccg gttccacagc cacattaacc atcactgggg tccaagccga cgacgaggct      240
gtctattact gtgggagctg ggacagcagc agtggtgctg gtatatttgg ggccgggaca      300
accctgaccg tcctaggtca gtcctctaga tcttccagcg gtggtggcag ctccggtggt      360
ggcggttccg ccgtgacgtt ggacgagtcc ggggcgcc tccagacgcc cggaggagcg      420
ctcagcctcg tctgcaaggc ctccgggttc accttcagca gttacgccat gaactgggtg      480
cgacaggcgc ccggcaaggg gctggagtgg gtcgcagcta ttagcagtga tggtagtagc      540
acaggatatg ggccggcggt ggagggccgt gccaccatct cgagggacaa cgggcagagc      600
acagtgaggc tgcagctgaa caacctcagg gctgaggaca ccggcaccta ctactgcgcc      660 aaaatgctt gtacttacgg tagtggttat tgtggttgga gtggtgctgg tggtatcgac      720
gcatggggcc acgggaccga agtcatcgtc tcctcc                             756
```

<210> SEQ ID NO 2
<211> LENGTH: 105
<212> TYPE: PRT
<213> ORGANISM: Artificial Sequence
<220> FEATURE:
<223> OTHER INFORMATION: Synthetic peptide

<400> SEQUENCE: 2

```
Ala Leu Thr Gln Pro Ser Ser Val Ser Ala Asn Pro Gly Glu Thr Val
1               5                   10                  15

Lys Ile Thr Cys Ser Gly Ser Ser Gly Ser Tyr Tyr Gly Trp His Gln
            20                  25                  30

Gln Lys Ser Pro Gly Ser Ala Pro Val Thr Leu Ile Tyr Asp Asn Thr
        35                  40                  45

Asn Arg Pro Ser Asp Ile Pro Ser Arg Phe Phe Gly Ser Lys Ser Gly
    50                  55                  60

Ser Thr Ala Thr Leu Thr Ile Thr Gly Val Gln Ala Asp Asp Glu Ala
65                  70                  75                  80

Val Tyr Tyr Cys Gly Ser Trp Asp Ser Ser Gly Ala Gly Ile Phe
                85                  90                  95

Gly Ala Gly Thr Thr Leu Thr Val Leu
            100                 105

<210> SEQ ID NO 3
<211> LENGTH: 18
<212> TYPE: PRT
<213> ORGANISM: Artificial Sequence
<220> FEATURE:
<223> OTHER INFORMATION: Synthetic peptide

<400> SEQUENCE: 3

Gly Gln Ser Ser Arg Ser Ser Ser Gly Gly Ser Ser Gly Gly Gly
1               5                   10                  15

Gly Ser

<210> SEQ ID NO 4
<211> LENGTH: 129
<212> TYPE: PRT
<213> ORGANISM: Artificial Sequence
<220> FEATURE:
<223> OTHER INFORMATION: Synthetic peptide

<400> SEQUENCE: 4

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ala Ala Ile Ser Ser Asp Gly Ser Ser Thr Gly Tyr Gly Pro Ala Val
    50                  55                  60

Glu Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys Asn Ala Cys Thr Tyr Gly Ser Gly Tyr Cys Gly Trp Ser Gly
            100                 105                 110

Ala Gly Gly Ile Asp Ala Trp Gly His Gly Thr Glu Val Ile Val Ser
        115                 120                 125

Ser

<210> SEQ ID NO 5
<211> LENGTH: 741
<212> TYPE: DNA
<213> ORGANISM: Artificial Sequence
<220> FEATURE:
<223> OTHER INFORMATION: Synthetic primer
```

<400> SEQUENCE: 5

```
gccctgactc agccgtcctc ggcgtcagca aacccgggag aaaccgtcga gatcacctgc      60
tccgggggtt acagcggcta tggctggttc cagcagaagt ctcctggcag tgcccctgtc     120
actctgatct atgaaaacga caagagaccc tcggacatcc cttcacgatt ctccggttcc     180
aaatccggct ccacgggcac attaaccatc actggggtcc aagccgacga cgaggctgtc     240
tatttctgtg ggagtgcaga caggagtaat aatgtgggta tatttggggc cgggacaacc     300
ctgaccgtcc taggtcagtc ctctagatct tccggcggtg gtggcagctc cggtggtggc     360
ggttccgccg tgacgttgga cgagtccggg ggcggcctcc agacgcccgg aggagcgctc     420
agcctcgtct gcaaggcctc cgggttcgac ttcagcagtt acgccatgaa ctgggtgcga     480
caggcgcccg gcaaggggct ggagtgggtc gctgctatta gtgacactgg tagtggcaca     540
ggatacgggg cggcggtgaa gggccgtgcc accatctcga gggacaacgg cagagcaca      600
gtgaggctgc agctgaacaa cctcagggca gaggacaccg gcatctactt ctgcgccaaa     660
gatgctggtt atgctgctgg ttggggtgct gctgggagca tcgacgcatg gggccacggg     720
accgaagtca tcgtctcctc c                                                741
```

<210> SEQ ID NO 6
<211> LENGTH: 104
<212> TYPE: PRT
<213> ORGANISM: Artificial Sequence
<220> FEATURE:
<223> OTHER INFORMATION: Synthetic peptide

<400> SEQUENCE: 6

```
Ala Leu Thr Gln Pro Ser Ser Ala Ser Ala Asn Pro Gly Glu Thr Val
1               5                   10                  15
Glu Ile Thr Cys Ser Gly Gly Tyr Ser Gly Tyr Gly Trp Phe Gln Gln
            20                  25                  30
Lys Ser Pro Gly Ser Ala Pro Val Thr Leu Ile Tyr Glu Asn Asp Lys
        35                  40                  45
Arg Pro Ser Asp Ile Pro Ser Arg Phe Ser Gly Ser Lys Ser Gly Ser
    50                  55                  60
Thr Gly Thr Leu Thr Ile Thr Gly Val Gln Ala Asp Asp Glu Ala Val
65                  70                  75                  80
Tyr Phe Cys Gly Ser Ala Asp Arg Ser Asn Asn Val Gly Ile Phe Gly
                85                  90                  95
Ala Gly Thr Thr Leu Thr Val Leu
            100
```

<210> SEQ ID NO 7
<211> LENGTH: 18
<212> TYPE: PRT
<213> ORGANISM: Artificial Sequence
<220> FEATURE:
<223> OTHER INFORMATION: Synthetic peptide

<400> SEQUENCE: 7

```
Gly Gln Ser Ser Arg Ser Ser Gly Gly Gly Gly Ser Ser Gly Gly Gly
1               5                   10                  15
Gly Ser
```

<210> SEQ ID NO 8
<211> LENGTH: 125
<212> TYPE: PRT

<213> ORGANISM: Artificial Sequence
<220> FEATURE:
<223> OTHER INFORMATION: Synthetic peptide

<400> SEQUENCE: 8

```
Ala Val Thr Leu Asp Glu Ser Gly Gly Gly Leu Gln Thr Pro Gly Gly
1               5                   10                  15
Ala Leu Ser Leu Val Cys Lys Ala Ser Gly Phe Asp Phe Ser Ser Tyr
            20                  25                  30
Ala Met Asn Trp Val Arg Gln Ala Pro Gly Lys Gly Leu Glu Trp Val
        35                  40                  45
Ala Ala Ile Ser Asp Thr Gly Ser Gly Thr Tyr Gly Ala Ala Val
    50                  55                  60
Lys Gly Arg Ala Thr Ile Ser Arg Asp Asn Gly Gln Ser Thr Val Arg
65                  70                  75                  80
Leu Gln Leu Asn Asn Leu Arg Ala Glu Asp Thr Gly Ile Tyr Phe Cys
                85                  90                  95
Ala Lys Asp Ala Gly Tyr Ala Ala Gly Trp Ala Ala Gly Ser Ile
            100                 105                 110
Asp Ala Trp Gly His Gly Thr Glu Val Ile Val Ser Ser
        115                 120                 125
```

<210> SEQ ID NO 9
<211> LENGTH: 738
<212> TYPE: DNA
<213> ORGANISM: Artificial Sequence
<220> FEATURE:
<223> OTHER INFORMATION: Synthetic primer

<400> SEQUENCE: 9

```
gccctgactc agccgtcctc ggtgtcagca aacctgggag gaaccgtcaa gatcacctgc      60
tccgggggta gtggcagcta cggctggttc agcagaagg cacctggcag tgccctgtc      120
actctgatct atgacaacac caacagaccc tcgaacatcc cttcacgatt ctccggttcc     180
acatctggct ccacaagcac attagccatc actggggtcc aagccgacga cgaggctgtc     240
tattactgtg ggagtgaaga catcagctat atcggtatat ttggggccgg gacaaccctg     300
accgtcctag gtcagtcctc tagatcttcc ggcggtggtg gcagctccgg tggtggcggt     360
tccgccgtga cgttggacga gtccgggggc ggcctccaga cgcccggagg agggctcagc     420
ctcgtctgca aggcctccgg cttcaccttc agcagtttct acatgttctg ggtgcgccag     480
gcgcccggca aggggctgga atacgtcgca gctattagca acactggtag tggcacagac     540
tacggggcgg cggtgcaggg ccgtgccacc atctcgaggg acaacgggca gagcacagtg     600
aggctgcagc tgaacaacct cagggctgag gacaccgcca cctactactg cgccaaagct     660
gctgctggtt gtactggttg tggtggtgct ggtagtatcg acgcatgggg ccacgggacc     720
gaagtcatcg tctcctcc                                                    738
```

<210> SEQ ID NO 10
<211> LENGTH: 103
<212> TYPE: PRT
<213> ORGANISM: Artificial Sequence
<220> FEATURE:
<223> OTHER INFORMATION: Synthetic peptide

<400> SEQUENCE: 10

```
Ala Leu Thr Gln Pro Ser Ser Val Ser Ala Asn Leu Gly Gly Thr Val
1               5                   10                  15
```

-continued

Lys Ile Thr Cys Ser Gly Gly Ser Gly Ser Tyr Gly Trp Phe Gln Gln
                20                  25                  30

Lys Ala Pro Gly Ser Ala Pro Val Thr Leu Ile Tyr Asp Asn Thr Asn
            35                  40                  45

Arg Pro Ser Asn Ile Pro Ser Arg Phe Ser Gly Ser Thr Ser Gly Ser
    50                  55                  60

Thr Ser Thr Leu Ala Ile Thr Gly Val Gln Ala Asp Asp Glu Ala Val
65                  70                  75                  80

Tyr Tyr Cys Gly Ser Glu Asp Ile Ser Tyr Ile Gly Ile Phe Gly Ala
                85                  90                  95

Gly Thr Thr Leu Thr Val Leu
            100

<210> SEQ ID NO 11
<211> LENGTH: 18
<212> TYPE: PRT
<213> ORGANISM: Artificial Sequence
<220> FEATURE:
<223> OTHER INFORMATION: Synthetic peptide

<400> SEQUENCE: 11

Gly Gln Ser Ser Arg Ser Ser Gly Gly Gly Ser Gly Gly Gly
1               5                   10                  15

Gly Ser

<210> SEQ ID NO 12
<211> LENGTH: 125
<212> TYPE: PRT
<213> ORGANISM: Artificial Sequence
<220> FEATURE:
<223> OTHER INFORMATION: Synthetic peptide

<400> SEQUENCE: 12

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Ser Ser Phe
                20                  25                  30

Tyr Met Phe Trp Val Arg Gln Ala Pro Gly Lys Gly Leu Glu Tyr Val
            35                  40                  45

Ala Ala Ile Ser Asn Thr Gly Ser Gly Thr Asp Tyr Gly Ala Ala Val
    50                  55                  60

Gln Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                85                  90                  95

Ala Lys Ala Ala Ala Gly Cys Thr Gly Cys Gly Gly Ala Gly Ser Ile
            100                 105                 110

Asp Ala Trp Gly His Gly Thr Glu Val Ile Val Ser Ser
        115                 120                 125

<210> SEQ ID NO 13
<211> LENGTH: 741
<212> TYPE: DNA
<213> ORGANISM: Artificial Sequence
<220> FEATURE:
<223> OTHER INFORMATION: Synthetic primer

<400> SEQUENCE: 13
gccctgactc agccgtcctc ggtgtcagca aacccaggag aaaccgtcaa gatcacctgc     60

| | | |
|---|---|---|
| tctgggggca gctatagcta tggctggtac cagcagaagg cacctggcag tgcccctgtc | 120 |
| actgtgatct atgacaacac caacagaccc tcgaacatcc cttcacgatt ctccggttcc | 180 |
| acatccggct ccacagccac attaaccatc actggggtcc gagccgagga cgaggctgtc | 240 |
| tattactgtg ggagtgcaga cagcagttac attggtatat ttggggccgg gacaaccctg | 300 |
| accgtcctag gtcagtcctc tagatcttcc ggcggtggtg gcagctccgg tggtggcggt | 360 |
| tccgccgtga cgttggacga gtccgggggc ggcctccaga cgcccggagg aacgctcagc | 420 |
| ctcgtctgca aggcctccgg gttcaccttc agcagcgtca acatgttctg gatgcgacag | 480 |
| gctccaggca aggggctgga gttcgttgct gctattggca atgatgctgg tgcacagac | 540 |
| tacggggcgg cggtggatgg ccgtgccacc atctcgaggg acaacgggca gagcacagtg | 600 |
| aggctgcagc tgaacaacct cagggctgag gacaccgcca cctactactg cgccaaagct | 660 |
| tctgcttgta gtacttctgg ttgtggtggt gctggtagca tcgacgcatg gggccacggg | 720 |
| accgaagtca tcgtctcctc c | 741 |

<210> SEQ ID NO 14
<211> LENGTH: 103
<212> TYPE: PRT
<213> ORGANISM: Artificial Sequence
<220> FEATURE:
<223> OTHER INFORMATION: Synthetic peptide

<400> SEQUENCE: 14

Ala Leu Thr Gln Pro Ser Ser Val Ser Ala Asn Pro Gly Glu Thr Val
1               5                   10                  15

Lys Ile Thr Cys Ser Gly Gly Ser Tyr Ser Tyr Gly Trp Tyr Gln Gln
            20                  25                  30

Lys Ala Pro Gly Ser Ala Pro Val Thr Val Ile Tyr Asp Asn Thr Asn
        35                  40                  45

Arg Pro Ser Asn Ile Pro Ser Arg Phe Ser Gly Ser Thr Ser Gly Ser
    50                  55                  60

Thr Ala Thr Leu Thr Ile Thr Gly Val Arg Ala Glu Asp Glu Ala Val
65                  70                  75                  80

Tyr Tyr Cys Gly Ser Ala Asp Ser Ser Tyr Ile Gly Ile Phe Gly Ala
                85                  90                  95

Gly Thr Thr Leu Thr Val Leu
            100

<210> SEQ ID NO 15
<211> LENGTH: 18
<212> TYPE: PRT
<213> ORGANISM: Artificial Sequence
<220> FEATURE:
<223> OTHER INFORMATION: Synthetic peptide

<400> SEQUENCE: 15

Gly Gln Ser Ser Arg Ser Ser Gly Gly Gly Gly Ser Ser Gly Gly Gly
1               5                   10                  15

Gly Ser

<210> SEQ ID NO 16
<211> LENGTH: 126
<212> TYPE: PRT
<213> ORGANISM: Artificial Sequence
<220> FEATURE:
<223> OTHER INFORMATION: Synthetic peptide

<400> SEQUENCE: 16

```
Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Thr Phe Ser Ser Val
            20                  25                  30

Asn Met Phe Trp Met Arg Gln Ala Pro Gly Lys Gly Leu Glu Phe Val
        35                  40                  45

Ala Ala Ile Gly Asn Asp Ala Gly Gly Thr Asp Tyr Gly Ala Ala Val
    50                  55                  60

Asp Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                85                  90                  95

Ala Lys Ala Ser Ala Cys Ser Thr Ser Gly Cys Gly Gly Ala Gly Ser
                100                 105                 110

Ile Asp Ala Trp Gly His Gly Thr Glu Val Ile Val Ser Ser
            115                 120                 125
```

<210> SEQ ID NO 17
<211> LENGTH: 741
<212> TYPE: DNA
<213> ORGANISM: Artificial Sequence
<220> FEATURE:
<223> OTHER INFORMATION: Synthetic primer

<400> SEQUENCE: 17

```
gccctgactc agccgtcctc ggtgtcagca aacctgggag gaaccgtcaa gatcatctgc      60
tccgggggtg gtggcagcta tggctggttc cagcagaagg cacctggcag tgccctgtc     120 actgtgatct atgacaacaa caagagaccc tcggacatcc cttcacgatt ctccggttcc    180
aaatccggct ccacggccac attaaccatc actggggtcc gagccgagga cgaggctgtc    240
tattactgtg ggagtgcaga caacacctat gttggtatat ttggggccgg gacaaccctg    300
accgtcctag gtcagtcctc tagatcttcc agcggtggtg gcagctccgg tggtggcggt    360
tccgccgtga cgttggacga gtccgggggc ggcctccaga cgcccggagg aacgctcagc    420
ctcgtctgca aggcctccgg gttcaccttc agcagcgtca catgttctg gatgcgacag     480 gctccaggca aggggctggg gttcgttgct gctattggca atgatgctgg tggcacagac    540 tacgggcgg cggtggatgg ccgtgccacc atctcgaggg acaacgggca gagcacagtg     600
aggctgcagc tgaacaacct cagggctgag gacaccgcca cctactactg cgccaaagct    660
tctgcttgta gtacctctgg ttgtggtggt gctggtagca tcgacgcatg gggccacggg    720
accgaagtca tcgtctcctc c                                              741
```

<210> SEQ ID NO 18
<211> LENGTH: 103
<212> TYPE: PRT
<213> ORGANISM: Artificial Sequence
<220> FEATURE:
<223> OTHER INFORMATION: Synthetic peptide

<400> SEQUENCE: 18

```
Ala Leu Thr Gln Pro Ser Ser Val Ser Ala Asn Leu Gly Gly Thr Val
1               5                   10                  15

Lys Ile Ile Cys Ser Gly Gly Gly Ser Tyr Gly Trp Phe Gln Gln
            20                  25                  30

Lys Ala Pro Gly Ser Ala Pro Val Thr Val Ile Tyr Asp Asn Asn Lys
        35                  40                  45
```

Arg Pro Ser Asp Ile Pro Ser Arg Phe Ser Gly Ser Lys Ser Gly Ser
        50                  55                  60

Thr Ala Thr Leu Thr Ile Thr Gly Val Arg Ala Glu Asp Glu Ala Val
65                  70                  75                  80

Tyr Tyr Cys Gly Ser Ala Asp Asn Thr Tyr Val Gly Ile Phe Gly Ala
                85                  90                  95

Gly Thr Thr Leu Thr Val Leu
            100

<210> SEQ ID NO 19
<211> LENGTH: 18
<212> TYPE: PRT
<213> ORGANISM: Artificial Sequence
<220> FEATURE:
<223> OTHER INFORMATION: Synthetic peptide

<400> SEQUENCE: 19

Gly Gln Ser Ser Arg Ser Ser Ser Gly Gly Ser Ser Gly Gly Gly
1               5                   10                  15

Gly Ser

<210> SEQ ID NO 20
<211> LENGTH: 126
<212> TYPE: PRT
<213> ORGANISM: Artificial Sequence
<220> FEATURE:
<223> OTHER INFORMATION: Synthetic peptide

<400> SEQUENCE: 20

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Thr Phe Ser Ser Val
                20                  25                  30

Asn Met Phe Trp Met Arg Gln Ala Pro Gly Lys Gly Leu Gly Phe Val
            35                  40                  45

Ala Ala Ile Gly Asn Asp Ala Gly Gly Thr Asp Tyr Gly Ala Ala Val
        50                  55                  60

Asp Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                85                  90                  95

Ala Lys Ala Ser Ala Cys Ser Thr Ser Gly Cys Gly Gly Ala Gly Ser
                100                 105                 110

Ile Asp Ala Trp Gly His Gly Thr Glu Val Ile Val Ser Ser
            115                 120                 125

<210> SEQ ID NO 21
<211> LENGTH: 744
<212> TYPE: DNA
<213> ORGANISM: Artificial Sequence
<220> FEATURE:
<223> OTHER INFORMATION: Synthetic primer

<400> SEQUENCE: 21
gccctgactc agccgtcctc ggtgtcagca aacccaggag aaaccgtcaa gatcacctgc      60
tccgggggtg gcagctatgg ttatggctgg taccagcaga aggcacctag cagtgcccct     120
gtcactgtga tttgctggga taacaagaga ccctcgaaca tccctttcacg attctccggt    180 tccacatctg gctccacagc cacattaacc atcactgggg tccaagccga ggacgaggct    240

```
gtctatttct gtgggagtgc agacagcagc ggtactgctg ctatatttgg ggccgggaca    300
aacctgaccg tcctaggtca gtcctctaga tcttccagcg gtggtggcag ctccggtggt    360
ggcggttccg ccgtgacgtt ggacgagtcc ggggcggcc tccagacgcc cggaggagcg    420
ctcagcctca tctgcaaggc ctccgggttc gacttcagca gttacgccat gaactgggtg    480
cgacaggcgc ccggcaaggg gctggagtgg gtcgcaagta ttgatgatgg tggtagtgac    540
acaacctacg gggcggcggt gaagggccgc gccaccgtct cgagggacaa cgggcagagc    600
acagtgaggc tgcagttgaa caacctcagg gctgaggaca ccggcaccta ctactgcgcc    660
aaagatgcta gtagtggtgg tgtttggagt gctgctgctg gcatcgacgc atggggccac    720
gggaccgaag tcatcgtctc ctcc                                           744
```

```
<210> SEQ ID NO 22
<211> LENGTH: 105
<212> TYPE: PRT
<213> ORGANISM: Artificial Sequence
<220> FEATURE:
<223> OTHER INFORMATION: Synthetic peptide

<400> SEQUENCE: 22

Ala Leu Thr Gln Pro Ser Ser Val Ser Ala Asn Pro Gly Glu Thr Val
1               5                   10                  15

Lys Ile Thr Cys Ser Gly Gly Gly Ser Tyr Gly Tyr Gly Trp Tyr Gln
            20                  25                  30

Gln Lys Ala Pro Ser Ser Ala Pro Val Thr Val Ile Cys Trp Asp Asn
        35                  40                  45

Lys Arg Pro Ser Asn Ile Pro Ser Arg Phe Ser Gly Ser Thr Ser Gly
    50                  55                  60

Ser Thr Ala Thr Leu Thr Ile Thr Gly Val Gln Ala Glu Asp Glu Ala
65                  70                  75                  80

Val Tyr Phe Cys Gly Ser Ala Asp Ser Ser Gly Thr Ala Ala Ile Phe
                85                  90                  95

Gly Ala Gly Thr Asn Leu Thr Val Leu
            100                 105

<210> SEQ ID NO 23
<211> LENGTH: 18
<212> TYPE: PRT
<213> ORGANISM: Artificial Sequence
<220> FEATURE:
<223> OTHER INFORMATION: Synthetic peptide

<400> SEQUENCE: 23

Gly Gln Ser Ser Arg Ser Ser Ser Gly Gly Gly Ser Ser Gly Gly Gly
1               5                   10                  15

Gly Ser

<210> SEQ ID NO 24
<211> LENGTH: 125
<212> TYPE: PRT
<213> ORGANISM: Artificial Sequence
<220> FEATURE:
<223> OTHER INFORMATION: Synthetic peptide

<400> SEQUENCE: 24

Ala Val Thr Leu Asp Glu Ser Gly Gly Gly Leu Gln Thr Pro Gly Gly
1               5                   10                  15

Ala Leu Ser Leu Ile Cys Lys Ala Ser Gly Phe Asp Phe Ser Ser Tyr
```

```
                  20                  25                  30
Ala Met Asn Trp Val Arg Gln Ala Pro Gly Lys Gly Leu Glu Trp Val
             35                  40                  45

Ala Ser Ile Asp Asp Gly Ser Asp Thr Thr Tyr Gly Ala Ala Val
         50                  55                  60

Lys Gly Arg Ala Thr Val Ser Arg Asp Asn Gly Gln Ser Thr Val Arg
 65                  70                  75                  80

Leu Gln Leu Asn Asn Leu Arg Ala Glu Asp Thr Gly Thr Tyr Tyr Cys
                 85                  90                  95

Ala Lys Asp Ala Ser Ser Gly Val Trp Ser Ala Ala Gly Ile
            100                 105                 110

Asp Ala Trp Gly His Gly Thr Glu Val Ile Val Ser Ser
            115                 120                 125

<210> SEQ ID NO 25
<211> LENGTH: 9
<212> TYPE: PRT
<213> ORGANISM: Artificial Sequence
<220> FEATURE:
<223> OTHER INFORMATION: Synthetic peptide

<400> SEQUENCE: 25

Ser Gly Ser Ser Gly Ser Tyr Tyr Gly
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic peptide

<400> SEQUENCE: 26

Asp Asn Thr Asn Arg Pro Ser
1               5

<210> SEQ ID NO 27
<211> LENGTH: 11
<212> TYPE: PRT
<213> ORGANISM: Artificial Sequence
<220> FEATURE:
<223> OTHER INFORMATION: Synthetic peptide

<400> SEQUENCE: 27

Gly Ser Trp Asp Ser Ser Ser Gly Ala Gly Ile
1               5                   10

<210> SEQ ID NO 28
<211> LENGTH: 5
<212> TYPE: PRT
<213> ORGANISM: Artificial Sequence
<220> FEATURE:
<223> OTHER INFORMATION: Synthetic peptide

<400> SEQUENCE: 28

Ser Tyr Ala Met Asn
1               5

<210> SEQ ID NO 29
<211> LENGTH: 18
<212> TYPE: PRT
<213> ORGANISM: Artificial Sequence
<220> FEATURE:
<223> OTHER INFORMATION: Synthetic peptide
```

<400> SEQUENCE: 29

Ala Ala Ile Ser Ser Asp Gly Ser Ser Thr Gly Tyr Gly Pro Ala Val
1               5                   10                  15

Glu Gly

<210> SEQ ID NO 30
<211> LENGTH: 20
<212> TYPE: PRT
<213> ORGANISM: Artificial Sequence
<220> FEATURE:
<223> OTHER INFORMATION: Synthetic peptide

<400> SEQUENCE: 30

Asn Ala Cys Thr Tyr Gly Ser Gly Tyr Cys Gly Trp Ser Gly Ala Gly
1               5                   10                  15

Gly Ile Asp Ala
            20

<210> SEQ ID NO 31
<211> LENGTH: 8
<212> TYPE: PRT
<213> ORGANISM: Artificial Sequence
<220> FEATURE:
<223> OTHER INFORMATION: Synthetic peptide

<400> SEQUENCE: 31

Ser Gly Gly Tyr Ser Gly Tyr Gly
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic peptide

<400> SEQUENCE: 32

Glu Asn Asp Lys Arg Pro Ser
1               5

<210> SEQ ID NO 33
<211> LENGTH: 11
<212> TYPE: PRT
<213> ORGANISM: Artificial Sequence
<220> FEATURE:
<223> OTHER INFORMATION: Synthetic peptide

<400> SEQUENCE: 33

Gly Ser Ala Asp Arg Ser Asn Asn Val Gly Ile
1               5                   10

<210> SEQ ID NO 34
<211> LENGTH: 5
<212> TYPE: PRT
<213> ORGANISM: Artificial Sequence
<220> FEATURE:
<223> OTHER INFORMATION: Synthetic peptide

<400> SEQUENCE: 34

Ser Tyr Ala Met Asn
1               5

<210> SEQ ID NO 35
<211> LENGTH: 17

```
<212> TYPE: PRT
<213> ORGANISM: Artificial Sequence
<220> FEATURE:
<223> OTHER INFORMATION: Synthetic peptide

<400> SEQUENCE: 35

Ala Ile Ser Asp Thr Gly Ser Gly Thr Gly Tyr Gly Ala Ala Val Lys
1               5                   10                  15
Gly

<210> SEQ ID NO 36
<211> LENGTH: 16
<212> TYPE: PRT
<213> ORGANISM: Artificial Sequence
<220> FEATURE:
<223> OTHER INFORMATION: Synthetic peptide

<400> SEQUENCE: 36

Asp Ala Gly Tyr Ala Ala Gly Trp Gly Ala Ala Gly Ser Ile Asp Ala
1               5                   10                  15

<210> SEQ ID NO 37
<211> LENGTH: 8
<212> TYPE: PRT
<213> ORGANISM: Artificial Sequence
<220> FEATURE:
<223> OTHER INFORMATION: Synthetic peptide

<400> SEQUENCE: 37

Ser Gly Gly Ser Gly Ser Tyr Gly
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic peptide

<400> SEQUENCE: 38

Asp Asn Thr Asn Arg Pro Ser
1               5

<210> SEQ ID NO 39
<211> LENGTH: 10
<212> TYPE: PRT
<213> ORGANISM: Artificial Sequence
<220> FEATURE:
<223> OTHER INFORMATION: Synthetic peptide

<400> SEQUENCE: 39

Gly Ser Glu Asp Ile Ser Tyr Ile Gly Ile
1               5                   10

<210> SEQ ID NO 40
<211> LENGTH: 5
<212> TYPE: PRT
<213> ORGANISM: Artificial Sequence
<220> FEATURE:
<223> OTHER INFORMATION: Synthetic peptide

<400> SEQUENCE: 40

Ser Phe Tyr Met Phe
1               5

<210> SEQ ID NO 41
```

```
<211> LENGTH: 17
<212> TYPE: PRT
<213> ORGANISM: Artificial Sequence
<220> FEATURE:
<223> OTHER INFORMATION: Synthetic peptide

<400> SEQUENCE: 41

Ala Ile Ser Asn Thr Gly Ser Gly Thr Asp Tyr Gly Ala Ala Val Gln
1               5                   10                  15

Gly

<210> SEQ ID NO 42
<211> LENGTH: 16
<212> TYPE: PRT
<213> ORGANISM: Artificial Sequence
<220> FEATURE:
<223> OTHER INFORMATION: Synthetic peptide

<400> SEQUENCE: 42

Ala Ala Ala Gly Cys Thr Gly Cys Gly Gly Ala Gly Ser Ile Asp Ala
1               5                   10                  15

<210> SEQ ID NO 43
<211> LENGTH: 8
<212> TYPE: PRT
<213> ORGANISM: Artificial Sequence
<220> FEATURE:
<223> OTHER INFORMATION: Synthetic peptide

<400> SEQUENCE: 43

Ser Gly Gly Ser Tyr Ser Tyr Gly
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic peptide

<400> SEQUENCE: 44

Asp Asn Thr Asn Arg Pro Ser
1               5

<210> SEQ ID NO 45
<211> LENGTH: 10
<212> TYPE: PRT
<213> ORGANISM: Artificial Sequence
<220> FEATURE:
<223> OTHER INFORMATION: Synthetic peptide

<400> SEQUENCE: 45

Gly Ser Ala Asp Ser Ser Tyr Ile Gly Ile
1               5                   10

<210> SEQ ID NO 46
<211> LENGTH: 5
<212> TYPE: PRT
<213> ORGANISM: Artificial Sequence
<220> FEATURE:
<223> OTHER INFORMATION: Synthetic peptide

<400> SEQUENCE: 46

Ser Val Asn Met Phe
1               5
```

```
<210> SEQ ID NO 47
<211> LENGTH: 17
<212> TYPE: PRT
<213> ORGANISM: Artificial Sequence
<220> FEATURE:
<223> OTHER INFORMATION: Synthetic peptide

<400> SEQUENCE: 47

Ala Ile Gly Asn Asp Ala Gly Gly Thr Asp Tyr Gly Ala Ala Val Asp
1               5                   10                  15
Gly

<210> SEQ ID NO 48
<211> LENGTH: 17
<212> TYPE: PRT
<213> ORGANISM: Artificial Sequence
<220> FEATURE:
<223> OTHER INFORMATION: Synthetic peptide

<400> SEQUENCE: 48

Ala Ser Ala Cys Ser Thr Ser Gly Cys Gly Gly Ala Gly Ser Ile Asp
1               5                   10                  15
Ala

<210> SEQ ID NO 49
<211> LENGTH: 8
<212> TYPE: PRT
<213> ORGANISM: Artificial Sequence
<220> FEATURE:
<223> OTHER INFORMATION: Synthetic peptide

<400> SEQUENCE: 49

Ser Gly Gly Gly Gly Ser Tyr Gly
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic peptide

<400> SEQUENCE: 50

Asp Asn Asn Lys Arg Pro Ser
1               5

<210> SEQ ID NO 51
<211> LENGTH: 10
<212> TYPE: PRT
<213> ORGANISM: Artificial Sequence
<220> FEATURE:
<223> OTHER INFORMATION: Synthetic peptide

<400> SEQUENCE: 51

Gly Ser Ala Asp Asn Thr Tyr Val Gly Ile
1               5                   10

<210> SEQ ID NO 52
<211> LENGTH: 5
<212> TYPE: PRT
<213> ORGANISM: Artificial Sequence
<220> FEATURE:
<223> OTHER INFORMATION: Synthetic peptide

<400> SEQUENCE: 52

Ser Val Asn Met Phe
```

```
<210> SEQ ID NO 53
<211> LENGTH: 17
<212> TYPE: PRT
<213> ORGANISM: Artificial Sequence
<220> FEATURE:
<223> OTHER INFORMATION: Synthetic peptide

<400> SEQUENCE: 53

Ala Ile Gly Asn Asp Ala Gly Gly Thr Asp Tyr Gly Ala Ala Val Asp
1               5                   10                  15
Gly

<210> SEQ ID NO 54
<211> LENGTH: 17
<212> TYPE: PRT
<213> ORGANISM: Artificial Sequence
<220> FEATURE:
<223> OTHER INFORMATION: Synthetic peptide

<400> SEQUENCE: 54

Ala Ser Ala Cys Ser Thr Ser Gly Cys Gly Gly Ala Gly Ser Ile Asp
1               5                   10                  15
Ala

<210> SEQ ID NO 55
<211> LENGTH: 9
<212> TYPE: PRT
<213> ORGANISM: Artificial Sequence
<220> FEATURE:
<223> OTHER INFORMATION: Synthetic peptide

<400> SEQUENCE: 55

Ser Gly Gly Gly Ser Tyr Gly Tyr Gly
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic peptide

<400> SEQUENCE: 56

Trp Asp Asn Lys Arg Pro Ser
1               5

<210> SEQ ID NO 57
<211> LENGTH: 11
<212> TYPE: PRT
<213> ORGANISM: Artificial Sequence
<220> FEATURE:
<223> OTHER INFORMATION: Synthetic peptide

<400> SEQUENCE: 57

Gly Ser Ala Asp Ser Ser Gly Thr Ala Ala Ile
1               5                   10

<210> SEQ ID NO 58
<211> LENGTH: 5
<212> TYPE: PRT
<213> ORGANISM: Artificial Sequence
<220> FEATURE:
<223> OTHER INFORMATION: Synthetic peptide
```

```
<400> SEQUENCE: 58

Ser Tyr Ala Met Asn
1               5

<210> SEQ ID NO 59
<211> LENGTH: 17
<212> TYPE: PRT
<213> ORGANISM: Artificial Sequence
<220> FEATURE:
<223> OTHER INFORMATION: Synthetic peptide

<400> SEQUENCE: 59

Ser Ile Asp Asp Gly Gly Ser Asp Thr Thr Tyr Gly Ala Ala Val Lys
1               5                   10                  15

Gly

<210> SEQ ID NO 60
<211> LENGTH: 16
<212> TYPE: PRT
<213> ORGANISM: Artificial Sequence
<220> FEATURE:
<223> OTHER INFORMATION: Synthetic peptide

<400> SEQUENCE: 60

Asp Ala Ser Ser Gly Gly Val Trp Ser Ala Ala Ala Gly Ile Asp Ala
1               5                   10                  15

<210> SEQ ID NO 61
<211> LENGTH: 4
<212> TYPE: PRT
<213> ORGANISM: Artificial Sequence
<220> FEATURE:
<223> OTHER INFORMATION: Synthetic peptide

<400> SEQUENCE: 61

Gly Ser Tyr Gly
1

<210> SEQ ID NO 62
<211> LENGTH: 3
<212> TYPE: PRT
<213> ORGANISM: Artificial Sequence
<220> FEATURE:
<223> OTHER INFORMATION: Synthetic peptide

<400> SEQUENCE: 62

Trp Asp Asn
1

<210> SEQ ID NO 63
<211> LENGTH: 11
<212> TYPE: PRT
<213> ORGANISM: Artificial Sequence
<220> FEATURE:
<223> OTHER INFORMATION: Synthetic peptide

<400> SEQUENCE: 63

Gly Ser Ala Asp Ser Ser Gly Thr Ala Ala Ile
1               5                   10

<210> SEQ ID NO 64
<211> LENGTH: 8
<212> TYPE: PRT
<213> ORGANISM: Artificial Sequence
<220> FEATURE:
<223> OTHER INFORMATION: Synthetic peptide
```

-continued

<400> SEQUENCE: 64

Gly Phe Asp Phe Ser Ser Tyr Ala
1               5

<210> SEQ ID NO 65
<211> LENGTH: 8
<212> TYPE: PRT
<213> ORGANISM: Artificial Sequence
<220> FEATURE:
<223> OTHER INFORMATION: Synthetic peptide

<400> SEQUENCE: 65

Ile Asp Asp Gly Gly Ser Asp Thr
1               5

<210> SEQ ID NO 66
<211> LENGTH: 18
<212> TYPE: PRT
<213> ORGANISM: Artificial Sequence
<220> FEATURE:
<223> OTHER INFORMATION: Synthetic peptide

<400> SEQUENCE: 66

Ala Lys Asp Ala Ser Ser Gly Gly Val Trp Ser Ala Ala Ala Gly Ile
1               5                   10                  15

Asp Ala

<210> SEQ ID NO 67
<211> LENGTH: 9
<212> TYPE: PRT
<213> ORGANISM: Artificial Sequence
<220> FEATURE:
<223> OTHER INFORMATION: Synthetic peptide

<400> SEQUENCE: 67

Ser Gly Gly Gly Ser Tyr Gly Tyr Gly
1               5

<210> SEQ ID NO 68
<211> LENGTH: 7
<212> TYPE: PRT
<213> ORGANISM: Artificial Sequence
<220> FEATURE:
<223> OTHER INFORMATION: Synthetic peptide

<400> SEQUENCE: 68

Trp Asp Asn Lys Arg Pro Ser
1               5

<210> SEQ ID NO 69
<211> LENGTH: 11
<212> TYPE: PRT
<213> ORGANISM: Artificial Sequence
<220> FEATURE:
<223> OTHER INFORMATION: Synthetic peptide

<400> SEQUENCE: 69

Gly Ser Ala Asp Ser Ser Gly Thr Ala Ala Ile
1               5                   10

<210> SEQ ID NO 70
<211> LENGTH: 7
<212> TYPE: PRT
<213> ORGANISM: Artificial Sequence
<220> FEATURE:

<223> OTHER INFORMATION: Synthetic peptide

<400> SEQUENCE: 70

Gly Phe Asp Phe Ser Ser Tyr
1               5

<210> SEQ ID NO 71
<211> LENGTH: 6
<212> TYPE: PRT
<213> ORGANISM: Artificial Sequence
<220> FEATURE:
<223> OTHER INFORMATION: Synthetic peptide

<400> SEQUENCE: 71

Asp Asp Gly Gly Ser Asp
1               5

<210> SEQ ID NO 72
<211> LENGTH: 16
<212> TYPE: PRT
<213> ORGANISM: Artificial Sequence
<220> FEATURE:
<223> OTHER INFORMATION: Synthetic peptide

<400> SEQUENCE: 72

Asp Ala Ser Ser Gly Gly Val Trp Ser Ala Ala Ala Gly Ile Asp Ala
1               5                   10                  15

<210> SEQ ID NO 73
<211> LENGTH: 4
<212> TYPE: PRT
<213> ORGANISM: Artificial Sequence
<220> FEATURE:
<223> OTHER INFORMATION: Synthetic peptide

<400> SEQUENCE: 73

Ser Gly Ser Tyr
1

<210> SEQ ID NO 74
<211> LENGTH: 3
<212> TYPE: PRT
<213> ORGANISM: Artificial Sequence
<220> FEATURE:
<223> OTHER INFORMATION: Synthetic peptide

<400> SEQUENCE: 74

Asp Asn Thr
1

<210> SEQ ID NO 75
<211> LENGTH: 13
<212> TYPE: PRT
<213> ORGANISM: Artificial Sequence
<220> FEATURE:
<223> OTHER INFORMATION: Synthetic peptide

<400> SEQUENCE: 75

Gly Ser Trp Asp Ser Ser Ser Gly Ala Gly Ile Phe Gly
1               5                   10

<210> SEQ ID NO 76
<211> LENGTH: 8
<212> TYPE: PRT
<213> ORGANISM: Artificial Sequence
<220> FEATURE:
<223> OTHER INFORMATION: Synthetic peptide

```
<400> SEQUENCE: 76

Gly Phe Thr Phe Ser Ser Tyr Ala
1               5

<210> SEQ ID NO 77
<211> LENGTH: 8
<212> TYPE: PRT
<213> ORGANISM: Artificial Sequence
<220> FEATURE:
<223> OTHER INFORMATION: Synthetic peptide

<400> SEQUENCE: 77

Ile Ser Ser Asp Gly Ser Ser Thr
1               5

<210> SEQ ID NO 78
<211> LENGTH: 22
<212> TYPE: PRT
<213> ORGANISM: Artificial Sequence
<220> FEATURE:
<223> OTHER INFORMATION: Synthetic peptide

<400> SEQUENCE: 78

Ala Lys Asn Ala Cys Thr Tyr Gly Ser Gly Tyr Cys Gly Trp Ser Gly
1               5                   10                  15

Ala Gly Gly Ile Asp Ala
            20

<210> SEQ ID NO 79
<211> LENGTH: 9
<212> TYPE: PRT
<213> ORGANISM: Artificial Sequence
<220> FEATURE:
<223> OTHER INFORMATION: Synthetic peptide

<400> SEQUENCE: 79

Ser Gly Ser Ser Gly Ser Tyr Tyr Gly
1               5

<210> SEQ ID NO 80
<211> LENGTH: 7
<212> TYPE: PRT
<213> ORGANISM: Artificial Sequence
<220> FEATURE:
<223> OTHER INFORMATION: Synthetic peptide

<400> SEQUENCE: 80

Asp Asn Thr Asn Arg Pro Ser
1               5

<210> SEQ ID NO 81
<211> LENGTH: 11
<212> TYPE: PRT
<213> ORGANISM: Artificial Sequence
<220> FEATURE:
<223> OTHER INFORMATION: Synthetic peptide

<400> SEQUENCE: 81

Gly Ser Trp Asp Ser Ser Ser Gly Ala Gly Ile
1               5                   10

<210> SEQ ID NO 82
<211> LENGTH: 7
<212> TYPE: PRT
<213> ORGANISM: Artificial Sequence
```

```
<220> FEATURE:
<223> OTHER INFORMATION: Synthetic peptide

<400> SEQUENCE: 82

Gly Phe Thr Phe Ser Ser Tyr
1               5

<210> SEQ ID NO 83
<211> LENGTH: 6
<212> TYPE: PRT
<213> ORGANISM: Artificial Sequence
<220> FEATURE:
<223> OTHER INFORMATION: Synthetic peptide

<400> SEQUENCE: 83

Ser Ser Asp Gly Ser Ser
1               5

<210> SEQ ID NO 84
<211> LENGTH: 20
<212> TYPE: PRT
<213> ORGANISM: Artificial Sequence
<220> FEATURE:
<223> OTHER INFORMATION: Synthetic peptide

<400> SEQUENCE: 84

Asn Ala Cys Thr Tyr Gly Ser Gly Tyr Cys Gly Trp Ser Gly Ala Gly
1               5                   10                  15

Gly Ile Asp Ala
            20

<210> SEQ ID NO 85
<211> LENGTH: 3
<212> TYPE: PRT
<213> ORGANISM: Artificial Sequence
<220> FEATURE:
<223> OTHER INFORMATION: Synthetic peptide

<400> SEQUENCE: 85

Tyr Ser Gly
1

<210> SEQ ID NO 86
<211> LENGTH: 3
<212> TYPE: PRT
<213> ORGANISM: Artificial Sequence
<220> FEATURE:
<223> OTHER INFORMATION: Synthetic peptide

<400> SEQUENCE: 86

Glu Asn Asp
1

<210> SEQ ID NO 87
<211> LENGTH: 13
<212> TYPE: PRT
<213> ORGANISM: Artificial Sequence
<220> FEATURE:
<223> OTHER INFORMATION: Synthetic peptide

<400> SEQUENCE: 87

Gly Ser Ala Asp Arg Ser Asn Asn Val Gly Ile Phe Gly
1               5                   10

<210> SEQ ID NO 88
<211> LENGTH: 10
```

```
<212> TYPE: PRT
<213> ORGANISM: Artificial Sequence
<220> FEATURE:
<223> OTHER INFORMATION: Synthetic peptide

<400> SEQUENCE: 88

Gly Phe Asp Phe Ser Ser Tyr Ala Met Asn
1               5                   10

<210> SEQ ID NO 89
<211> LENGTH: 9
<212> TYPE: PRT
<213> ORGANISM: Artificial Sequence
<220> FEATURE:
<223> OTHER INFORMATION: Synthetic peptide

<400> SEQUENCE: 89

Ala Ile Ser Asp Thr Gly Ser Gly Thr
1               5

<210> SEQ ID NO 90
<211> LENGTH: 18
<212> TYPE: PRT
<213> ORGANISM: Artificial Sequence
<220> FEATURE:
<223> OTHER INFORMATION: Synthetic peptide

<400> SEQUENCE: 90

Ala Lys Asp Ala Gly Tyr Ala Ala Gly Trp Gly Ala Ala Gly Ser Ile
1               5                   10                  15

Asp Ala

<210> SEQ ID NO 91
<211> LENGTH: 8
<212> TYPE: PRT
<213> ORGANISM: Artificial Sequence
<220> FEATURE:
<223> OTHER INFORMATION: Synthetic

<400> SEQUENCE: 91

Ser Gly Gly Tyr Ser Gly Tyr Gly
1               5

<210> SEQ ID NO 92
<211> LENGTH: 7
<212> TYPE: PRT
<213> ORGANISM: Artificial Sequence
<220> FEATURE:
<223> OTHER INFORMATION: Synthetic

<400> SEQUENCE: 92

Glu Asn Asp Lys Arg Pro Ser
1               5

<210> SEQ ID NO 93
<211> LENGTH: 11
<212> TYPE: PRT
<213> ORGANISM: Artificial Sequence
<220> FEATURE:
<223> OTHER INFORMATION: Synthetic

<400> SEQUENCE: 93

Gly Ser Ala Asp Arg Ser Asn Asn Val Gly Ile
1               5                   10

<210> SEQ ID NO 94
```

```
<211> LENGTH: 10
<212> TYPE: PRT
<213> ORGANISM: Artificial Sequence
<220> FEATURE:
<223> OTHER INFORMATION: Synthetic

<400> SEQUENCE: 94

Gly Phe Asp Phe Ser Ser Tyr Ala Met Asn
1               5                   10

<210> SEQ ID NO 95
<211> LENGTH: 8
<212> TYPE: PRT
<213> ORGANISM: Artificial Sequence
<220> FEATURE:
<223> OTHER INFORMATION: Synthetic

<400> SEQUENCE: 95

Ala Ile Ser Asp Thr Gly Ser Gly
1               5

<210> SEQ ID NO 96
<211> LENGTH: 16
<212> TYPE: PRT
<213> ORGANISM: Artificial Sequence
<220> FEATURE:
<223> OTHER INFORMATION: Synthetic

<400> SEQUENCE: 96

Asp Ala Gly Tyr Ala Ala Gly Trp Gly Ala Ala Gly Ser Ile Asp Ala
1               5                   10                  15

<210> SEQ ID NO 97
<211> LENGTH: 8
<212> TYPE: PRT
<213> ORGANISM: Artificial Sequence
<220> FEATURE:
<223> OTHER INFORMATION: Synthetic

<400> SEQUENCE: 97

Ser Gly Gly Ser Gly Ser Tyr Gly
1               5

<210> SEQ ID NO 98
<211> LENGTH: 7
<212> TYPE: PRT
<213> ORGANISM: Artificial Sequence
<220> FEATURE:
<223> OTHER INFORMATION: Synthetic

<400> SEQUENCE: 98

Asp Asn Thr Asn Arg Pro Ser
1               5

<210> SEQ ID NO 99
<211> LENGTH: 7
<212> TYPE: PRT
<213> ORGANISM: Artificial Sequence
<220> FEATURE:
<223> OTHER INFORMATION: Synthetic

<400> SEQUENCE: 99

Asp Asn Thr Asn Arg Pro Ser
1               5

<210> SEQ ID NO 100
<211> LENGTH: 8
```

```
<212> TYPE: PRT
<213> ORGANISM: Artificial Sequence
<220> FEATURE:
<223> OTHER INFORMATION: Synthetic peptide

<400> SEQUENCE: 100

Gly Phe Thr Phe Ser Ser Phe Tyr
1               5

<210> SEQ ID NO 101
<211> LENGTH: 8
<212> TYPE: PRT
<213> ORGANISM: Artificial Sequence
<220> FEATURE:
<223> OTHER INFORMATION: Synthetic peptide

<400> SEQUENCE: 101

Ile Ser Asn Thr Gly Ser Gly Thr
1               5

<210> SEQ ID NO 102
<211> LENGTH: 18
<212> TYPE: PRT
<213> ORGANISM: Artificial Sequence
<220> FEATURE:
<223> OTHER INFORMATION: Synthetic peptide

<400> SEQUENCE: 102

Ala Lys Ala Ala Ala Gly Cys Thr Gly Cys Gly Gly Ala Gly Ser Ile
1               5                   10                  15

Asp Ala

<210> SEQ ID NO 103
<211> LENGTH: 8
<212> TYPE: PRT
<213> ORGANISM: Artificial Sequence
<220> FEATURE:
<223> OTHER INFORMATION: Synthetic peptide

<400> SEQUENCE: 103

Ser Gly Gly Ser Gly Ser Tyr Gly
1               5

<210> SEQ ID NO 104
<211> LENGTH: 7
<212> TYPE: PRT
<213> ORGANISM: Artificial Sequence
<220> FEATURE:
<223> OTHER INFORMATION: Synthetic peptide

<400> SEQUENCE: 104

Asp Asn Thr Asn Arg Pro Ser
1               5

<210> SEQ ID NO 105
<211> LENGTH: 7
<212> TYPE: PRT
<213> ORGANISM: Artificial Sequence
<220> FEATURE:
<223> OTHER INFORMATION: Synthetic peptide

<400> SEQUENCE: 105

Asp Asn Thr Asn Arg Pro Ser
1               5

<210> SEQ ID NO 106
```

```
<211> LENGTH: 7
<212> TYPE: PRT
<213> ORGANISM: Artificial Sequence
<220> FEATURE:
<223> OTHER INFORMATION: Synthetic peptide

<400> SEQUENCE: 106

Gly Phe Thr Phe Ser Ser Phe
1               5

<210> SEQ ID NO 107
<211> LENGTH: 6
<212> TYPE: PRT
<213> ORGANISM: Artificial Sequence
<220> FEATURE:
<223> OTHER INFORMATION: Synthetic peptide

<400> SEQUENCE: 107

Ser Asn Thr Gly Ser Gly
1               5

<210> SEQ ID NO 108
<211> LENGTH: 16
<212> TYPE: PRT
<213> ORGANISM: Artificial Sequence
<220> FEATURE:
<223> OTHER INFORMATION: Synthetic peptide

<400> SEQUENCE: 108

Ala Ala Ala Gly Cys Thr Gly Cys Gly Gly Ala Gly Ser Ile Asp Ala
1               5                   10                  15

<210> SEQ ID NO 109
<211> LENGTH: 3
<212> TYPE: PRT
<213> ORGANISM: Artificial Sequence
<220> FEATURE:
<223> OTHER INFORMATION: Synthetic peptide

<400> SEQUENCE: 109

Ser Tyr Ser
1

<210> SEQ ID NO 110
<211> LENGTH: 3
<212> TYPE: PRT
<213> ORGANISM: Artificial Sequence
<220> FEATURE:
<223> OTHER INFORMATION: Synthetic peptide

<400> SEQUENCE: 110

Asp Asn Thr
1

<210> SEQ ID NO 111
<211> LENGTH: 10
<212> TYPE: PRT
<213> ORGANISM: Artificial Sequence
<220> FEATURE:
<223> OTHER INFORMATION: Synthetic peptide

<400> SEQUENCE: 111

Gly Ser Ala Asp Ser Ser Tyr Ile Gly Ile
1               5                   10

<210> SEQ ID NO 112
<211> LENGTH: 8
```

```
<212> TYPE: PRT
<213> ORGANISM: Artificial Sequence
<220> FEATURE:
<223> OTHER INFORMATION: Synthetic peptide

<400> SEQUENCE: 112

Gly Phe Thr Phe Ser Ser Val Asn
1               5

<210> SEQ ID NO 113
<211> LENGTH: 8
<212> TYPE: PRT
<213> ORGANISM: Artificial Sequence
<220> FEATURE:
<223> OTHER INFORMATION: Synthetic peptide

<400> SEQUENCE: 113

Ile Gly Asn Asp Ala Gly Gly Thr
1               5

<210> SEQ ID NO 114
<211> LENGTH: 19
<212> TYPE: PRT
<213> ORGANISM: Artificial Sequence
<220> FEATURE:
<223> OTHER INFORMATION: Synthetic peptide

<400> SEQUENCE: 114

Ala Lys Ala Ser Ala Cys Ser Thr Ser Gly Cys Gly Gly Ala Gly Ser
1               5                   10                  15

Ile Asp Ala

<210> SEQ ID NO 115
<211> LENGTH: 8
<212> TYPE: PRT
<213> ORGANISM: Artificial Sequence
<220> FEATURE:
<223> OTHER INFORMATION: Synthetic peptide

<400> SEQUENCE: 115

Ser Gly Gly Ser Tyr Ser Tyr Gly
1               5

<210> SEQ ID NO 116
<211> LENGTH: 7
<212> TYPE: PRT
<213> ORGANISM: Artificial Sequence
<220> FEATURE:
<223> OTHER INFORMATION: Synthetic peptide

<400> SEQUENCE: 116

Asp Asn Thr Asn Arg Pro Ser
1               5

<210> SEQ ID NO 117
<211> LENGTH: 10
<212> TYPE: PRT
<213> ORGANISM: Artificial Sequence
<220> FEATURE:
<223> OTHER INFORMATION: Synthetic peptide

<400> SEQUENCE: 117

Gly Ser Ala Asp Ser Ser Tyr Ile Gly Ile
1               5                   10

<210> SEQ ID NO 118
```

```
<211> LENGTH: 7
<212> TYPE: PRT
<213> ORGANISM: Artificial Sequence
<220> FEATURE:
<223> OTHER INFORMATION: Synthetic peptide

<400> SEQUENCE: 118

Gly Phe Thr Phe Ser Ser Val
1               5

<210> SEQ ID NO 119
<211> LENGTH: 6
<212> TYPE: PRT
<213> ORGANISM: Artificial Sequence
<220> FEATURE:
<223> OTHER INFORMATION: Synthetic peptide

<400> SEQUENCE: 119

Gly Asn Asp Ala Gly Gly
1               5

<210> SEQ ID NO 120
<211> LENGTH: 17
<212> TYPE: PRT
<213> ORGANISM: Artificial Sequence
<220> FEATURE:
<223> OTHER INFORMATION: Synthetic peptide

<400> SEQUENCE: 120

Ala Ser Ala Cys Ser Thr Ser Gly Cys Gly Gly Ala Gly Ser Ile Asp
1               5                   10                  15

Ala

<210> SEQ ID NO 121
<211> LENGTH: 3
<212> TYPE: PRT
<213> ORGANISM: Artificial Sequence
<220> FEATURE:
<223> OTHER INFORMATION: Synthetic peptide

<400> SEQUENCE: 121

Gly Gly Ser
1

<210> SEQ ID NO 122
<211> LENGTH: 3
<212> TYPE: PRT
<213> ORGANISM: Artificial Sequence
<220> FEATURE:
<223> OTHER INFORMATION: Synthetic peptide

<400> SEQUENCE: 122

Asp Asn Asn
1

<210> SEQ ID NO 123
<211> LENGTH: 10
<212> TYPE: PRT
<213> ORGANISM: Artificial Sequence
<220> FEATURE:
<223> OTHER INFORMATION: Synthetic peptide

<400> SEQUENCE: 123

Gly Ser Ala Asp Asn Thr Tyr Val Gly Ile
1               5                   10
```

```
<210> SEQ ID NO 124
<211> LENGTH: 8
<212> TYPE: PRT
<213> ORGANISM: Artificial Sequence
<220> FEATURE:
<223> OTHER INFORMATION: Synthetic peptide

<400> SEQUENCE: 124

Gly Phe Thr Phe Ser Ser Val Asn
1               5

<210> SEQ ID NO 125
<211> LENGTH: 8
<212> TYPE: PRT
<213> ORGANISM: Artificial Sequence
<220> FEATURE:
<223> OTHER INFORMATION: Synthetic peptide

<400> SEQUENCE: 125

Ile Gly Asn Asp Ala Gly Gly Thr
1               5

<210> SEQ ID NO 126
<211> LENGTH: 19
<212> TYPE: PRT
<213> ORGANISM: Artificial Sequence
<220> FEATURE:
<223> OTHER INFORMATION: Synthetic peptide

<400> SEQUENCE: 126

Ala Lys Ala Ser Ala Cys Ser Thr Ser Gly Cys Gly Gly Ala Gly Ser
1               5                   10                  15

Ile Asp Ala

<210> SEQ ID NO 127
<211> LENGTH: 8
<212> TYPE: PRT
<213> ORGANISM: Artificial Sequence
<220> FEATURE:
<223> OTHER INFORMATION: Synthetic peptide

<400> SEQUENCE: 127

Ser Gly Gly Gly Gly Ser Tyr Gly
1               5

<210> SEQ ID NO 128
<211> LENGTH: 7
<212> TYPE: PRT
<213> ORGANISM: Artificial Sequence
<220> FEATURE:
<223> OTHER INFORMATION: Synthetic peptide

<400> SEQUENCE: 128

Asp Asn Asn Lys Arg Pro Ser
1               5

<210> SEQ ID NO 129
<211> LENGTH: 10
<212> TYPE: PRT
<213> ORGANISM: Artificial Sequence
<220> FEATURE:
<223> OTHER INFORMATION: Synthetic peptide

<400> SEQUENCE: 129

Gly Ser Ala Asp Asn Thr Tyr Val Gly Ile
1               5                   10
```

```
<210> SEQ ID NO 130
<211> LENGTH: 7
<212> TYPE: PRT
<213> ORGANISM: Artificial Sequence
<220> FEATURE:
<223> OTHER INFORMATION: Synthetic peptide

<400> SEQUENCE: 130

Gly Phe Thr Phe Ser Ser Val
1               5

<210> SEQ ID NO 131
<211> LENGTH: 6
<212> TYPE: PRT
<213> ORGANISM: Artificial Sequence
<220> FEATURE:
<223> OTHER INFORMATION: Synthetic peptide

<400> SEQUENCE: 131

Gly Asn Asp Ala Gly Gly
1               5

<210> SEQ ID NO 132
<211> LENGTH: 17
<212> TYPE: PRT
<213> ORGANISM: Artificial Sequence
<220> FEATURE:
<223> OTHER INFORMATION: Synthetic peptide

<400> SEQUENCE: 132

Ala Ser Ala Cys Ser Thr Ser Gly Cys Gly Gly Ala Gly Ser Ile Asp
1               5                  10                  15

Ala
```

MONOCLONAL ANTIBODIES TO ELTD1 AND USES THEREOF

CROSS-REFERENCE TO RELATED APPLICATIONS

This application is a National Stage of International Application of PCT/US2019/059488, filed Nov. 1, 2019, which claims the benefit of U.S. Provisional Application No. 62/754,684 filed Nov. 2, 2018. The contents of each of which are incorporated by reference in their entirety.

TECHNICAL FIELD OF THE INVENTION

The present invention relates in general to the field of Antibodies against ELTD1 that can be used for treatment of multiple sclerosis, retinopathy, tissue regeneration, and the detection and treatment of cancers.

STATEMENT OF FEDERALLY FUNDED RESEARCH

Not applicable.

INCORPORATION-BY-REFERENCE OF MATERIALS FILED ON COMPACT DISC

The application includes an electronically submitted sequence listing in .txt format. The .txt format file contains a sequence listing entitled "OMRF1016US_ST25.txt" created Nov. 1, 2024 and is 43,281 bytes in size. The sequence listing contained in this .txt file is part of the specification and is hereby incorporated by reference herein in its entirety.

BACKGROUND OF THE INVENTION

Without limiting the scope of the invention, its background is described in connection with EGF, latrophilin and seven transmembrane domain-containing protein 1 (ELTD1).

ELTD1 is a latrophilin-like orphan receptor of the adhesion G protein-coupled receptor family. In humans, the ELTD1 gene encodes ELTD1. ELTD1 appears to have a role in angiogenesis, both physiological and pathological, as well as glioblastoma. However, its role in other diseases is largely unexplored.

SUMMARY OF THE INVENTION

In one embodiment, the present invention includes a method of treating a subject having or suspected of having multiple sclerosis comprising delivering to the subject an antibody or antibody fragment having binding affinity for an EGF, latrophilin and seven transmembrane domain-containing protein 1 (ELTD1). In one aspect, the antibody is a recombinant bivalent scFv Fc-fusion antibody. In another aspect, the antibody fragment is a recombinant scFv (single chain fragment variable) antibody, Fab fragment, F(ab')$_2$ fragment, or Fv fragment. In another aspect, the antibody or antibody fragment is chimeric, humanized, fully human, or bispecific. In another aspect, the antibody or antibody fragment comprises an Fc portion mutated to alter (eliminate or enhance) FcR interactions to increase half-life and/or increase or decrease effector function such as antibody-dependent cellular cytotoxicity or complement activation. In another aspect, an antibody light chain variable region and heavy chain variable region have the amino acid sequences of SEQ ID NOS: 2 and 4, 6 and 8, 10 and 12, 14 and 16, 18 and 20, or 22 and 24, respectively. In another aspect, the antibody has light chain variable regions complementarity determining regions (CDR) CDR1, CDR2, and CDR3 of SEQ ID NOS: 25, 26 and 27; 31, 32 and 33; 37, 38 and 39; 43, 44 and 45; 49, 50 and 51; 55, 56 and 57; 61, 62 and 63; 67, 68 and 69; 73, 74 and 75; 79, 80 and 81; 85, 86 and 87; 91, 92 and 93; 97, 98 and 99; 103, 104 and 105; 109, 110 and 111; 115, 116 and 117; 121, 122 and 123; or 127, 128 and 129, respectively. In another aspect, the antibody has heavy chain variable regions CDR1, CDR2, and CDR3 of SEQ ID NOS: 28, 29 and 30; 34, 35 and 36; 40, 41 and 42; 46, 47 and 48; 52, 53 and 54; 58, 59 and 60; 64, 65 and 66; 70, 71 and 72; 76, 77 and 78; 82, 83 and 84; 88, 89 and 90; 94, 95 and 96; 100, 101 and 102; 106, 107 and 108; 112, 113 and 114; 118, 119 and 120; 124, 125 and 126; or 130, 131 and 132, respectively. In another aspect, the antibody or antibody fragment is adapted for administration or genetic delivery with an RNA or DNA sequence or vector encoding the antibody or antibody fragment. In another aspect, the method further comprises providing an active agent that treats or reduces the symptoms of multiple sclerosis selected from Corticosteroids, Plasma exchange (plasmapheresis), ocrelizumab (Ocrevus), Beta interferons, Glatiramer acetate (Copaxone, Glatopa), Fingolimod (Gilenya), Dimethyl fumarate (Tecfidera), Teriflunomide (Aubagio), Siponimod (Mayzent), Ocrelizumab (Ocrevus), Natalizumab (Tysabri), Alemtuzumab (Campath, Lemtrada), Mitoxantrone, or functional derivative thereof. In another aspect, the method further comprises adding a probe to the antibody or antibody fragment for non-invasive in vivo detection of ELTD1.

In another embodiment, the present invention includes a method of treating a subject having or suspected of having a retinopathy comprising delivering to the subject an antibody or antibody fragment having binding affinity for an EGF, latrophilin and seven transmembrane domain-containing protein 1 (ELTD1). In one aspect, the antibody is a recombinant bivalent scFv Fc-fusion antibody. In another aspect, the antibody fragment is a recombinant scFv (single chain fragment variable) antibody, Fab fragment, F(ab')$_2$ fragment, or Fv fragment. In another aspect, the antibody or antibody fragment is chimeric, humanized, fully human, or bispecific. In another aspect, the antibody or antibody fragment comprises an Fc portion mutated to alter (eliminate or enhance) FcR interactions to increase half-life and/or increase or decrease effector function such as antibody-dependent cellular cytotoxicity or complement activation. In another aspect, an antibody light chain variable region and heavy chain variable region have the amino acid sequences of SEQ ID NOS: 2 and 4, 6 and 8, 10 and 12, 14 and 16, 18 and 20, or 22 and 24, respectively. In another aspect, the antibody has light chain variable regions CDR1, CDR2, and CDR3 of SEQ ID NOS: 25, 26 and 27; 31, 32 and 33; 37, 38 and 39; 43, 44 and 45; 49, 50 and 51; 55, 56 and 57; 61, 62 and 63; 67, 68 and 69; 73, 74 and 75; 79, 80 and 81; 85, 86 and 87; 91, 92 and 93; 97, 98 and 99; 103, 104 and 105; 109, 110 and 111; 115, 116 and 117; 121, 122 and 123; or 127, 128 and 129, respectively. In another aspect, the antibody has heavy chain variable regions CDR1, CDR2, and CDR3 of SEQ ID NOS: 28, 29 and 30; 34, 35 and 36; 40, 41 and 42; 46, 47 and 48; 52, 53 and 54; 58, 59 and 60; 64, 65 and 66; 70, 71 and 72; 76, 77 and 78; 82, 83 and 84; 88, 89 and 90; 94, 95 and 96; 100, 101 and 102; 106, 107 and 108; 112, 113 and 114; 118, 119 and 120; 124, 125 and 126; or 130, 131 and 132, respectively. In another aspect, the antibody or antibody fragment is adapted for administration or genetic delivery with an RNA or DNA sequence or vector encoding the antibody or antibody fragment. In another aspect, the method further comprises providing an active agent that treats or reduces the symptoms of retinopathy selected from corticosteroids, VEGF inhibitors, PKC inhibitors, or growth hormone inhibitors.

In another embodiment, the present invention includes a pharmaceutical formulation comprising a polyclonal antiserum or one or more monoclonal antibodies or antibody fragments that bind to EGF, latrophilin and seven transmembrane domain-containing protein 1 (ELTD1). In one aspect, the antibody is a recombinant bivalent scFv Fc-fusion antibody. In another aspect, at least one of the antibody fragments is a recombinant scFv (single chain fragment variable) antibody, Fab fragment, F(ab')$_2$ fragment, or Fv fragment. In another aspect, the antibody or antibody fragment is chimeric, humanized, fully human, or bispecific. In another aspect, the antibody or antibody fragment comprises an Fc portion mutated to alter (eliminate or enhance) FcR interactions to increase half-life and/or increase or decrease effector function such as antibody-dependent cellular cytotoxicity or complement activation. In another aspect, at least one of a light chain variable region and a heavy chain variable region has the amino acid sequences of SEQ ID NOS: 2 and 4, 6 and 8, 10 and 12, 14 and 16, 18 and 20, or 22 and 24, respectively. In another aspect, the antibody has light chain variable region complementarity determining regions (CDR) CDR1, CDR2, and CDR3 of SEQ ID NOS: 25, 26 and 27; 31, 32 and 33; 37, 38 and 39; 43, 44 and 45; 49, 50 and 51; 55, 56 and 57; 61, 62 and 63; 67, 68 and 69; 73, 74 and 75; 79, 80 and 81; 85, 86 and 87; 91, 92 and 93; 97, 98 and 99; 103, 104 and 105; 109, 110 and 111; 115, 116 and 117; 121, 122 and 123; or 127, 128 and 129, respectively. In another aspect, the antibody has heavy chain variable regions CDR1, CDR2, and CDR3 of SEQ ID NOS: 28, 29 and 30; 34, 35 and 36; 40, 41 and 42; 46, 47 and 48; 52, 53 and 54; 58, 59 and 60; 64, 65 and 66; 70, 71 and 72; 76, 77 and 78; 82, 83 and 84; 88, 89 and 90; 94, 95 and 96; 100, 101 and 102; 106, 107 and 108; 112, 113 and 114; 118, 119 and 120; 124, 125 and 126; or 130, 131 and 132, respectively. In another aspect, the antibody or antibody fragment is adapted for administration or genetic delivery with an RNA or DNA sequence or vector encoding the antibody or antibody fragment. In another aspect, at least one of the antibodies or antibody fragments further comprises a cell penetrating peptide and/or is an intrabody.

In another embodiment, the present invention includes a method of promoting tissue regeneration comprising contacting a cell or tissue with a polyclonal antiserum or an antibody or antibody fragment having binding affinity for ELTD1. In one aspect, the antibody is a recombinant bivalent scFv Fc-fusion antibody. In another aspect, the antibody fragment is a recombinant scFv (single chain fragment variable) antibody, Fab fragment, F(ab')2 fragment, or Fv fragment. In another aspect, the antibody or antibody fragment is chimeric, humanized, fully human, or bispecific. In another aspect, the antibody or antibody fragment comprises an Fc portion mutated to alter (eliminate or enhance) FcR interactions to increase half-life and/or increase or decrease effector function such as antibody-dependent cellular cytotoxicity or complement activation. In another aspect, the antibody light chain variable region and heavy chain variable region has the amino acid sequences of SEQ ID NOS: 2 and 4, 6 and 8, 10 and 12, 14 and 16, 18 and 20, or 22 and 24. In another aspect, the antibody has light chain variable regions CDR1, CDR2, and CDR3 of SEQ ID NOS: 25, 26 and 27; 31, 32 and 33; 37, 38 and 39; 43, 44 and 45; 49, 50 and 51; 55, 56 and 57; 61, 62 and 63; 67, 68 and 69; 73, 74 and 75; 79, 80 and 81; 85, 86 and 87; 91, 92 and 93; 97, 98 and 99; 103, 104 and 105; 109, 110 and 111; 115, 116 and 117; 121, 122 and 123; or 127, 128 and 129, respectively. In another aspect, the antibody has heavy chain variable regions CDR1, CDR2, and CDR3 of SEQ ID NOS: 28, 29 and 30; 34, 35 and 36; 40, 41 and 42; 46, 47 and 48; 52, 53 and 54; 58, 59 and 60; 64, 65 and 66; 70, 71 and 72; 76, 77 and 78; 82, 83 and 84; 88, 89 and 90; 94, 95 and 96; 100, 101 and 102; 106, 107 and 108; 112, 113 and 114; 118, 119 and 120; 124, 125 and 126; or 130, 131 and 132, respectively. In another aspect, the antibody or antibody fragment is adapted for administration or genetic delivery with an RNA or DNA sequence or vector encoding the antibody or antibody fragment. In another aspect, the cell is contacted in vitro. In another aspect, the cell is contacted in vivo. In another aspect, the cell is a heart cell, a liver cell, a muscle cell, a kidney cell, a skin cell, a lung cell, a bladder cell, an intestinal cell, a hair follicle cell, a retinal cell, a corneal cell, a stomach cell, a nerve cell, an endothelial cell, a pancreatic cell, a thyroid cell, an epidermal cell, a neuronal cell, a microglia cell, an astrocyte cell, and a breast cell. In another aspect, tissue regeneration includes at least one of nerve regeneration, vascular regeneration, or bone regeneration.

In another embodiment, the present invention includes a method of treating a subject having or suspected of having cancer comprising delivering to the subject an antibody or antibody fragment having binding affinity for ELTD1. In another aspect, the antibody is a recombinant bivalent scFv Fc-fusion antibody. In another aspect, the antibody fragment is a recombinant scFv (single chain fragment variable) antibody, Fab fragment, F(ab')2 fragment, or Fv fragment. In another aspect, the antibody or antibody fragment is chimeric, humanized, fully human, or bispecific. In another aspect, the antibody or antibody fragment comprises an Fc portion mutated to alter (eliminate or enhance) FcR interactions to increase half-life and/or increase or decrease effector function such as antibody-dependent cellular cytotoxicity or complement activation. In another aspect, the antibody light chain variable region and heavy chain variable region have the amino acid sequences of SEQ ID NOS: 2 and 4, 6 and 8, 10 and 12, 14 and 16, 18 and 20, or 22 and 24, respectively. In another aspect, the antibody has light chain variable regions CDR1, CDR2, and CDR3 of SEQ ID NOS: 25, 26 and 27; 31, 32 and 33; 37, 38 and 39; 43, 44 and 45; 49, 50 and 51; 55, 56 and 57; 61, 62 and 63; 67, 68 and 69; 73, 74 and 75; 79, 80 and 81; 85, 86 and 87; 91, 92 and 93; 97, 98 and 99; 103, 104 and 105; 109, 110 and 111; 115, 116 and 117; 121, 122 and 123; or 127, 128 and 129, respectively. In another aspect, the wherein the antibody has heavy chain variable regions CDR1, CDR2, and CDR3 of SEQ ID NOS: 28, 29 and 30; 34, 35 and 36; 40, 41 and 42; 46, 47 and 48; 52, 53 and 54; 58, 59 and 60; 64, 65 and 66; 70, 71 and 72; 76, 77 and 78; 82, 83 and 84; 88, 89 and 90; 94, 95 and 96; 100, 101 and 102; 106, 107 and 108; 112, 113 and 114; 118, 119 and 120; 124, 125 and 126; or 130, 131 and 132, respectively. In another aspect, the antibody or antibody fragment is adapted for administration or genetic delivery with an RNA or DNA sequence or vector encoding the antibody or antibody fragment. In another aspect, the subject has a metastatic colorectal cancer, first-line non-squamous non-small cell lung cancer, recurrent glioblastoma multiforme, metastatic renal cell carcinoma, persistent, recurrent, or metastatic cervical cancer, and epithelial ovarian, fallopian tube, or primary peritoneal cancer. In another aspect, the method further comprises treating the subject with a second cancer therapy, such as radiation, chemotherapy, immunotherapy, toxin therapy or surgery. In another aspect, the antibody or antibody fragment is adapted for administration by genetic delivery with an RNA or DNA sequence or vector encoding the antibody or antibody fragment. In another aspect, the antibody or antibody fragment shows reduced or no hemorrhage during administration. In another aspect, the cancer is a metastatic colorectal cancer, first-line non-squamous non-small cell lung cancer, recurrent glioblastoma multiforme, metastatic renal cell carcinoma, persistent, recurrent, or metastatic cervical cancer, and epithelial ovarian, fallopian tube, or primary peritoneal cancer.

In another embodiment, the present invention includes a monoclonal antibody or binding fragment thereof that binds specifically to ELTD1 comprising a light chain variable region and a heavy chain variable region having an amino acid sequences of SEQ ID NOS: 2 and 4, 6 and 8, 10 and 12, 14 and 16, 18 and 20, or 22 and 24, respectively. In one aspect, the antibody is a recombinant bivalent scFv Fc-fusion antibody. In another aspect, the binding fragment is a recombinant scFv (single chain fragment variable) antibody, Fab fragment, F(ab')2 fragment, or Fv fragment. In another aspect, the antibody or antibody fragment is chimeric, humanized, fully human, or bispecific. In another aspect, the antibody or antibody fragment comprises an Fc portion mutated to alter (eliminate or enhance) FcR interactions to increase half-life and/or increase or decrease effector function such as antibody-dependent cellular cytotoxicity or complement activation. In another aspect, the antibody is a scFv and is encoded by a nucleic acid of at least one of SEQ ID NOS: 1, 5, 9, 13, 17, or 21. In another aspect, the monoclonal antibody or binding fragments thereof has light chain variable regions CDR1, CDR2, and CDR3 of SEQ ID NOS: 25, 26 and 27; 31, 32 and 33; 37, 38 and 39; 43, 44 and 45; 49, 50 and 51; 55, 56 and 57; 61, 62 and 63; 67, 68 and 69; 73, 74 and 75; 79, 80 and 81; 85, 86 and 87; 91, 92 and 93; 97, 98 and 99; 103, 104 and 105; 109, 110 and 111; 115, 116 and 117; 121, 122 and 123; or 127, 128 and 129, respectively. In another aspect, the monoclonal antibody or binding fragments thereof has heavy chain variable regions CDR1, CDR2, and CDR3 of SEQ ID NOS: 28, 29 and 30; 34, 35 and 36; 40, 41 and 42; 46, 47 and 48; 52, 53 and 54; 58, 59 and 60; 64, 65 and 66; 70, 71 and 72; 76, 77 and 78; 82, 83 and 84; 88, 89 and 90; 94, 95 and 96; 100, 101 and 102; 106, 107 and 108; 112, 113 and 114; 118, 119 and 120; 124, 125 and 126; or 130, 131 and 132, respectively. In another aspect, the monoclonal antibody or binding fragment thereof has at least one of: light chain variable regions CDR1, CDR2, and CDR3 of SEQ ID NOS: 25, 26 and 27; 31, 32 and 33; 37, 38 and 39; 43, 44 and 45; 49, 50 and 51; 55, 56 and 57; 61, 62 and 63; 67, 68 and 69; 73, 74 and 75; 79, 80 and 81; 85, 86 and 87; 91, 92 and 93; 97, 98 and 99; 103, 104 and 105; 109, 110 and 111; 115, 116 and 117; 121, 122 and 123; or 127, 128 and 129, respectively; or heavy chain variable regions CDR1, CDR2, and CDR3 of SEQ ID NOS: 28, 29 and 30; 34, 35 and 36; 40, 41 and 42; 46, 47 and 48; 52, 53 and 54; 58, 59 and 60; 64, 65 and 66; 70, 71 and 72; 76, 77 and 78; 82, 83 and 84; 88, 89 and 90; 94, 95 and 96; 100, 101 and 102; 106, 107 and 108; 112, 113 and 114; 118, 119 and 120; 124, 125 and 126; or 130, 131 and 132, respectively; or both. In one aspect, the antibody or antibody fragment is adapted for administration or genetic delivery with an RNA or DNA sequence or vector encoding the antibody or antibody fragment. In another aspect, the monoclonal antibody further comprises a probe attached to the antibody or antibody fragment.

In another embodiment, the present invention includes a method of detecting ELTD1 in a subject comprising: obtaining a biological sample from the subject; and contacting the biological sample with a monoclonal antibody or binding fragment thereof that binds specifically to ELTD1, wherein the monoclonal antibody or binding fragment thereof has at least one of: light chain variable regions CDR1, CDR2, and CDR3 of SEQ ID NOS: 25, 26 and 27; 31, 32 and 33; 37, 38 and 39; 43, 44 and 45; 49, 50 and 51; 55, 56 and 57; 61, 62 and 63; 67, 68 and 69; 73, 74 and 75; 79, 80 and 81; 85, 86 and 87; 91, 92 and 93; 97, 98 and 99; 103, 104 and 105; 109, 110 and 111; 115, 116 and 117; 121, 122 and 123; or 127, 128 and 129, respectively; or heavy chain variable regions CDR1, CDR2, and CDR3 of SEQ ID NOS: 28, 29 and 30; 34, 35 and 36; 40, 41 and 42; 46, 47 and 48; 52, 53 and 54; 58, 59 and 60; 64, 65 and 66; 70, 71 and 72; 76, 77 and 78; 82, 83 and 84; 88, 89 and 90; 94, 95 and 96; 100, 101 and 102; 106, 107 and 108; 112, 113 and 114; 118, 119 and 120; 124, 125 and 126; or 130, 131 and 132, respectively; or both; and detecting the binding of the monoclonal antibody or binding fragment thereof to the sample. In one aspect, the antibody is a recombinant bivalent scFv Fc-fusion antibody.

In another embodiment, the present invention includes a dual function monoclonal antibody or antibody fragment thereof or a polyclonal serum having binding affinity for ELTD1 that downregulates both Notch1 and VEGFR2 when contacted with a target cell. In another aspect, the antibody is a recombinant bivalent scFv Fc-fusion antibody. In another aspect, the antibody fragment is a recombinant scFv (single chain fragment variable) antibody, Fab fragment, F(ab')2 fragment, or Fv fragment. In another aspect, the antibody or antibody fragment is chimeric, humanized, fully human, or bispecific. In another aspect, the antibody or antibody fragment comprises an Fc portion mutated to alter (eliminate or enhance) FcR interactions to increase half-life and/or increase or decrease effector function such as antibody-dependent cellular cytotoxicity or complement activation. In another aspect, the antibody is a scFv and is encoded by a nucleic acid of at least one of SEQ ID NOS: 1, 5, 9, 13, 17, or 21. In another aspect, the monoclonal antibody has the amino acid sequences of SEQ ID NOS:2 and 4, 6 and 8, 10 and 12, 14 and 16, 18 and 20, or 22 and 24. In another aspect, the monoclonal antibody or binding fragment thereof has light chain variable regions CDR1, CDR2, and CDR3 of SEQ ID NOS: 25, 26 and 27; 31, 32 and 33; 37, 38 and 39; 43, 44 and 45; 49, 50 and 51; 55, 56 and 57; 61, 62 and 63; 67, 68 and 69; 73, 74 and 75; 79, 80 and 81; 85, 86 and 87; 91, 92 and 93; 97, 98 and 99; 103, 104 and 105; 109, 110 and 111; 115, 116 and 117; 121, 122 and 123; or 127, 128 and 129, respectively. In another aspect, the monoclonal antibody or binding fragment thereof has heavy chain variable regions CDR1, CDR2, and CDR3 of SEQ ID NOS: 28, 29 and 30; 34, 35 and 36; 40, 41 and 42; 46, 47 and 48; 52, 53 and 54; 58, 59 and 60; 64, 65 and 66; 70, 71 and 72; 76, 77 and 78; 82, 83 and 84; 88, 89 and 90; 94, 95 and 96; 100, 101 and 102; 106, 107 and 108; 112, 113 and 114; 118, 119 and 120; 124, 125 and 126; or 130, 131 and 132, respectively. In another aspect, the monoclonal antibody or binding fragment thereof has at least one of: light chain variable regions CDR1, CDR2, and CDR3 of SEQ ID NOS: 25, 26 and 27; 31, 32 and 33; 37, 38 and 39; 43, 44 and 45; 49, 50 and 51; 55, 56 and 57; 61, 62 and 63; 67, 68 and 69; 73, 74 and 75; 79, 80 and 81; 85, 86 and 87; 91, 92 and 93; 97, 98 and 99; 103, 104 and 105; 109, 110 and 111; 115, 116 and 117; 121, 122 and 123; or 127, 128 and 129, respectively; or heavy chain variable regions CDR1, CDR2, and CDR3 of SEQ ID NOS: 28, 29 and 30; 34, 35 and 36; 40, 41 and 42; 46, 47 and 48; 52, 53 and 54; 58, 59 and 60; 64, 65 and 66; 70, 71 and 72; 76, 77 and 78; 82, 83 and 84; 88, 89 and 90;

94, 95 and 96; 100, 101 and 102; 106, 107 and 108; 112, 113 and 114; 118, 119 and 120; 124, 125 and 126; or 130, 131 and 132, respectively; or both. In another aspect, the antibody or antibody fragment is adapted for administration or genetic delivery with an RNA or DNA sequence or vector encoding the antibody or antibody fragment. In another aspect, the monoclonal antibody or antibody fragment thereof either inhibits proliferation or initiates cell death, or both, in vitro. In another aspect, when the antibody binds to a cancer cell, it decreases expression of at least one of: sodium channel protein type 5 subunit alpha, or L1 cell adhesion molecule. In another aspect, wherein when the antibody binds to a cancer cell it increases the expression at least one of: ADA, SCN5A, L1CAM, BMP2, Alkaline phosphatase (ALPL), TRPM8 in all tumors that express ELTD1. In another aspect, wherein when the antibody binds to a cancer cell it decreases the expression of SELENBP1. In another aspect, wherein when the antibody binds to a hepatocellular carcinoma: VWA1 is decreased. In another aspect, wherein when the antibody binds to a lung cancer cell and expression of least one of: SCUBE3 is decreased, PLCH1 is increased, CHRNA1 is increased, or CDH2 is increased. In another aspect, wherein when the antibody binds to a breast cancer cell: IFITM10—decreased, DCDC2—increased, CHST9—increased, and CDH2—increased. In another aspect, wherein when the antibody binds to a cancer cell, it increases expression of: CD74. In another aspect, wherein when the antibody binds to a retinal cell, it decreases expression of at least one of: Adenosine deaminase or apelin. In another aspect, wherein when the antibody binds to a retinal cell, it increases expression of: bone gamma-carboxyglutamate protein, matrilin 2, or von Willebrand factor A domain containing 1. In another aspect, wherein when the antibody is provided to a subject with multiple sclerosis, it decreases expression of at least one of: sodium channel protein type 5 subunit alpha, Adenosine deaminase, apelin, spinster homolog 2, or bone morphogenetic protein 2. In another aspect, wherein when the antibody is provided to a subject with multiple sclerosis, it increases expression of at least one of: CD74 or IKAROS family zinc finger 1 (Ikaros). In another aspect, wherein when the antibody is provided to a subject at a site in need of tissue regeneration, it increases expression of at least one of: bone gamma-carboxyglutamate (gla) protein, matrilin 2, or von Willebrand factor A domain containing 1. In another aspect, wherein the antibody is provided in an amount sufficient to treat a cancer selected from metastatic colorectal cancer, first-line non-squamous non-small cell lung cancer, recurrent glioblastoma multiforme, metastatic renal cell carcinoma, persistent, recurrent, or metastatic cervical cancer, and epithelial ovarian, fallopian tube, or primary peritoneal cancer.

In another embodiment, the present invention includes a method of treating a disease or condition with an anti-EGF, latrophilin and seven transmembrane domain-containing protein 1 (ELTD1) antibody or fragment thereof in a subject comprising: identifying a subject in need of treatment for the disease or condition; and providing with an effective amount of the antibody or binding fragment thereof that binds specifically to ELTD1 sufficient to reduce the symptoms from or treat the disease or condition, wherein the disease or condition is selected from multiple sclerosis, retinopathy, cancer, or tissue regeneration. In one aspect, the antibody is a polyclonal or monoclonal antibody, or a fragment thereof. In another aspect, the antibody is a recombinant bivalent scFv Fc-fusion antibody. In another aspect, the monoclonal antibody or binding fragment thereof is a recombinant scFv (single chain fragment variable) antibody, Fab fragment, F(ab')2 fragment, or Fv fragment. In another aspect, the monoclonal antibody or antibody fragment is chimeric, humanized, fully human, or bispecific. In another aspect, the antibody or antibody fragment comprises an Fc portion mutated to alter (eliminate or enhance) FcR interactions to increase half-life and/or increase or decrease effector function such as antibody-dependent cellular cytotoxicity or complement activation. In another aspect, the antibody is a scFv and is encoded by a nucleic acid of at least one of SEQ ID NOS: 1, 5, 9, 13, 17, or 21. In another aspect, the monoclonal antibody has the amino acid sequences of SEQ ID NOS:2 and 4, 6 and 8, 10 and 12, 14 and 16, 18 and 20, or 22 and 24. In another aspect, the monoclonal antibody or binding fragment thereof has light chain variable regions CDR1, CDR2, and CDR3 of SEQ ID NOS: 25, 26 and 27; 31, 32 and 33; 37, 38 and 39; 43, 44 and 45; 49, 50 and 51; 55, 56 and 57; 61, 62 and 63; 67, 68 and 69; 73, 74 and 75; 79, 80 and 81; 85, 86 and 87; 91, 92 and 93; 97, 98 and 99; 103, 104 and 105; 109, 110 and 111; 115, 116 and 117; 121, 122 and 123; or 127, 128 and 129, respectively. In another aspect, the monoclonal antibody or binding fragment thereof has heavy chain variable regions CDR1, CDR2, and CDR3 of SEQ ID NOS: 28, 29 and 30; 34, 35 and 36; 40, 41 and 42; 46, 47 and 48; 52, 53 and 54; 58, 59 and 60; 64, 65 and 66; 70, 71 and 72; 76, 77 and 78; 82, 83 and 84; 88, 89 and 90; 94, 95 and 96; 100, 101 and 102; 106, 107 and 108; 112, 113 and 114; 118, 119 and 120; 124, 125 and 126; or 130, 131 and 132, respectively. In another aspect, the monoclonal antibody or binding fragment thereof has at least one of: light chain variable regions CDR1, CDR2, and CDR3 of SEQ ID NOS: 25, 26 and 27; 31, 32 and 33; 37, 38 and 39; 43, 44 and 45; 49, 50 and 51; 55, 56 and 57; 61, 62 and 63; 67, 68 and 69; 73, 74 and 75; 79, 80 and 81; 85, 86 and 87; 91, 92 and 93; 97, 98 and 99; 103, 104 and 105; 109, 110 and 111; 115, 116 and 117; 121, 122 and 123; or 127, 128 and 129, respectively; or heavy chain variable regions CDR1, CDR2, and CDR3 of SEQ ID NOS: 28, 29 and 30; 34, 35 and 36; 40, 41 and 42; 46, 47 and 48; 52, 53 and 54; 58, 59 and 60; 64, 65 and 66; 70, 71 and 72; 76, 77 and 78; 82, 83 and 84; 88, 89 and 90; 94, 95 and 96; 100, 101 and 102; 106, 107 and 108; 112, 113 and 114; 118, 119 and 120; 124, 125 and 126; or 130, 131 and 132, respectively; or both. In another aspect, the antibody or antibody fragment is adapted for administration or genetic delivery with an RNA or DNA sequence or vector encoding the antibody or antibody fragment. In another aspect, wherein when the antibody binds it downregulates nestin. In another aspect, the dual function monoclonal antibody further comprises a probe. In another aspect, the dual function monoclonal antibody further comprises a probe detectable via MRI. In another aspect, when the antibody binds to a cancer cell, it decreases expression of at least one of: sodium channel protein type 5 subunit alpha, or L1 cell adhesion molecule. In another aspect, when the antibody binds to a cancer cell, it increases expression of: CD74. In another aspect, when the antibody binds to a retinal cell, it decreases expression of at least one of: Adenosine deaminase or apelin. In another aspect, when the antibody binds to a retinal cell, it increases expression of: bone gamma-carboxyglutamate protein, matrilin 2, or von Willebrand factor A domain containing 1. In another aspect, when the antibody is provided to a subject with multiple sclerosis, it decreases expression of at least one of: sodium channel protein type 5 subunit alpha, Adenosine deaminase, apelin, spinster homolog 2, or bone morphogenetic protein 2. In another aspect, when the antibody is provided to a subject with multiple sclerosis, it increases expression of at least one of: CD74 or IKAROS family zinc finger 1 (Ikaros). In another aspect, when the antibody is provided to a subject at a site in need of tissue regeneration, it increases expression of at least one of: bone gamma-carboxyglutamate (gla) protein, matrilin 2, or von Willebrand factor A domain containing 1. In another aspect, when the antibody down-regulates nestin. In another aspect, the antibody further comprises a probe. In another aspect, the antibody further comprises a probe detectable via MRI.

In another embodiment, the present invention includes a method of diagnosing a disease or condition in a subject with an anti-EGF, latrophilin and seven transmembrane domain-containing protein 1 (ELTD1) antibody or fragment thereof comprising: identifying a subject in need of treatment for the disease or condition; obtaining a biological sample from the subject; and contacting the sample with an anti-EGF, latrophilin and seven transmembrane domain-containing protein 1 (ELTD1) antibody or binding fragment thereof that comprises a detectable marker, wherein the disease or condition is selected from multiple sclerosis, retinopathy, cancer, or tissue in need of regeneration.

BRIEF DESCRIPTION OF THE DRAWINGS

For a more complete understanding of the features and advantages of the present invention, reference is now made to the detailed description of the invention along with the accompanying figures.

(FIG. 1A) Percent survival curve for all treatment groups. Anti-ELTD1 polyclonal antibody (pAb) and monoclonal antibody (mAb) treatments were able to significantly increase the overall survival post tumor detection as compared to untreated (UT) controls. (FIG. 1B) Tumor volumes (TV) of each treatment group 9 days post-tumor detection. Anti-ELTD1 pAb and mAb treatment significantly decreased TV compared to UT (*p=0.0384, **p=0.0067). Representative morphological MR-images for UT control (FIG. 1C), anti-ELTD1 pAb treatment FIG. 1 (D), and anti-ELTD1 mAb treatment (FIG. 1E) 9 days post tumor-detection with the tumor outlined in yellow.

(FIG. 2G) Quantitative analysis of tumor relative cerebral blood flow (rCBF) differences. The rCBF perfusion levels were significantly increased with both anti-ELTD1 treatments with the anti-ELTD1 mAb significantly better than the pAb. The mAb treatment was also able to normalize the perfusion levels (*p=0.0001 UT vs pAb, **p<0.0001 UT vs mAb).

(FIG. 3D) MVD analysis for all of the treatment groups. The pAb and mAb treatments were able to significantly decrease MVD (**p<0.0001 for both). There was also a significant decrease in MVD for the mAb relative to the pAb. (p<0.01)

(FIG. 4A) Molecular probe construct. Gd-DTPA signal was used to detect the probe via MR-imaging while the biotin tag allowed for localization in the tumor tissue post-termination. (FIG. 4B) Percent relative expression of the molecular probes indicates a change in either T1 Relaxation or SI due to the presence of the Gd-DTPA component. The mAb attached probe had significantly higher signal intensity and T1 relaxation time than the IgG control (T1: *p=0.0307 (IgG vs pAb ELTD1 probe), *p=0.0002 (IgG vs mAb ELTD1 probe); SI: p=0.008 (IgG vs mAb ELTD1 probe)). (FIG. 4C, FIG. 4D) Localization and clustering of anti-ELTD1 monoclonal-attached molecular probes (FIG. 4C) and non-specific IgG-attached molecular probe (FIG. 4D). (FIG. 4E) Kinetics of the antibody-attached probes: non-specific IgG control, pAb, and mAb against ELTD1. (FIG. 4F-H) Representative images (20×) stained with SA-HRP to localize the non-specific IgG-attached probes (FIG. 4F), anti-ELTD1 pAb-attached probe (FIG. 4G), and anti-ELTD1 mAb-attached probe (FIG. 4H). The brown staining seen in the pAb and mAb attached probes are the localized probes.

(FIG. 5A-D) Representative images (20×) of IHC stained tumors with anti-Notch1 in untreated animals (FIG. 5A), anti-ELTD1 pAb-treated animals (FIG. 5B), anti-ELTD1 mAb-treated animals (FIG. 5C), and contralateral control stained tissues (FIG. 5D). (FIG. 5E) Quantitative positivity Notch staining of the samples. Anti-ELTD1 mAb-treated mice significantly lowered Notch levels when compared to both untreated and anti-ELTD1 pAb-treated animals. There was no significant difference between untreated vs pAb-treated animals, and between mAb-treated animals and contralateral (healthy control) tissues. Contralateral (Cont) tissue Notch levels were significantly lower than untreated and pAb-treated animals (*p=0.0357 (mAb vs. pAb), p=0.0015 (Cont vs pAb), *p=0.0006 (UT vs. mAb), ****p<0.0001 (UT vs. Cont)).

(FIG. 6B) Gene-gene correlations for the genes repressed after anti-ELT1 mAb treatment of mice with GBM. Red=positively correlated, green=negatively correlated. Using literature analysis software to categorize the groups of genes in terms of their published commonalities, they roughly fall into 4 categories (developmental genes, nestin-related, cell proliferation/angiogenesis and astrocyte/microglia inflammation).

(FIG. 7A) Antibody treatment against ELTD1, both mAb (Monoclonal) (p=0.0058) and an scFv fragment (Fragment) (*p=0.0001), significantly increased the tumor percent survival compared to UT control animals as shown in the percent survival curve. (FIG. 7B) Tumor volumes in mice with GBM were also found to be significantly lower with anti-ELTD1 mAb (*p=0.0009) and scFv fragment (*p=0.017) treatment compared to untreated animals. Also shown by the representative morphological tumor images of untreated (FIG. 7C), anti-ELTD1 mAb-treated (FIG. 7D), and anti-ELTD1 scFv fragment (FIG. 7E) treated mice.

(FIG. 8A) The anti-ELTD1 mAb and scFv fragment treatments were significantly more effective in minimizing the decrease in the rCBF (****$p<0.0001$) compared to untreated mice. Representative morphological image and perfusion maps for untreated (FIGS. 8B, 8C), anti-ELTD1 mAb-treated (FIGS. 8D, 8E), and anti-ELTD1 scFv fragment-treated (FIGS. 8F, 8G) animals are shown.

(FIG. 9D) Both mAb and scFv fragment treatment against ELTD1 significantly decreased microvessel densities within the tumor region (****$p<0.0001$).

(FIG. 11A) Construct of the molecular targeting probe attached with either non-specific IgG, anti-ELTD1 mAb, or anti-ELTD1 scFv fragment. Binding of the (FIG. 11C) mAb attached probe over 90 minutes, and the (FIG. 11D) scFv fragment attached probe over 180 minutes. (FIG. 11B) Signal intensity was significantly increased by the monoclonal and fragment anti-ELTD1 attached probe ($p=0.0038$, *$p=0.0007$).

FIGS. 12A to 12 D show that the anti-ELTD1 scFv fragment attached molecular probe was successful in reaching and targeting diffuse tumor regions not seen through magnetic resonance imaging (MRI). (A,B) Top voxel: Bulk tumor (validated by H&E; A) had traces of the anti-ELTD1 scFv fragment attached-molecular probe as shown through SA-HRP (B). (C,D) Bottom voxel: The anti-ELTD1 scFv fragment attached-molecular probe was successful in reaching diffuse tumor regions, as shown through H&E (C) and SA-HRP (D) images.

(FIG. 19B) Immunohistochemistry staining for ELTD1 indicates high levels in endothelial cells of an EAE mouse.

DETAILED DESCRIPTION OF THE INVENTION

Figure 1A:
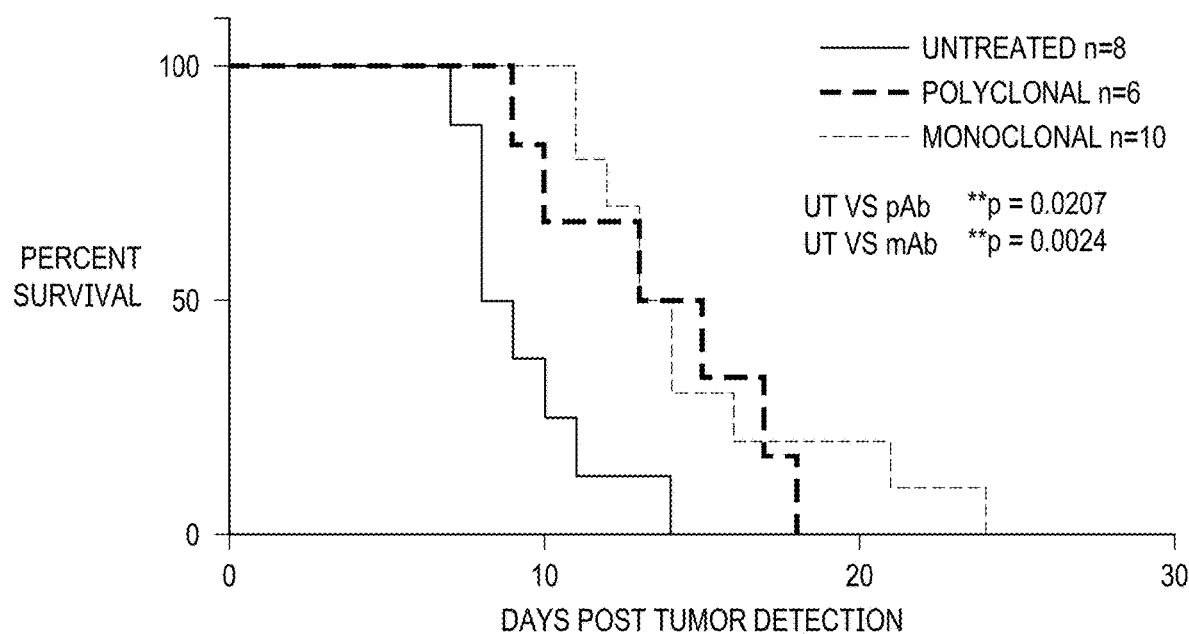
FIGS. 1A to 1E show monoclonal anti-ELTD1 treatment is more effective than polyclonal anti-ELTD1 treatment in increasing animal survival and decreasing tumor volumes (TV) in mice with glioblastoma (GBM).

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but include the general class of which a specific example may be used for illustration. The terminology herein is used to describe specific embodiments of the invention, but their usage does not limit the invention, except as outlined in the claims.

As discussed above, ELTD1 is known to be involved in angiogenesis and is linked to glioblastoma. Little else is known about its role in biology and disease. Here, the inventors have shown that ELTD1 is useful for diagnosis and treatment of other diseases including multiple sclerosis and retinopathy, and may, more generally, be important in tissue regeneration. The inventors used the antibodies taught herein against ELTD1.

As used herein, the terms "antibody" or "antibody peptide(s)" refer to an intact antibody, or a binding fragment thereof that competes with the intact antibody for specific binding. Binding fragments are produced by recombinant DNA techniques, or by enzymatic or chemical cleavage of intact antibodies. Binding fragments include Fab, Fab', F(ab')$_2$, Fv, and single-chain variable fragment (scFv) antibodies. An antibody other than a "bispecific" or "bifunctional" antibody is understood to have each of its binding sites identical. An antibody substantially inhibits adhesion of a receptor to a counter receptor when an excess of antibody reduces the quantity of receptor bound to counter receptor by at least about 20%, 40%, 60% or 80%, and more usually greater than about 85% (as measured in an in vitro competitive binding assay).

As used herein, the term "antibody" is used in the broadest sense, and specifically covers monoclonal antibodies (including full length antibodies or other bivalent, Fc-region containing antibodies such as bivalent scFv Fc-fusion antibodies), polyclonal antibodies, multispecific antibodies (e.g., bispecific antibodies), and antibody fragments (e.g., Fab, Fab', F(ab')$_2$, Fv, scFv) so long as they exhibit the desired biological activity. Antibodies (Abs) and immunoglobulins (Igs) are glycoproteins having the same structural characteristics. While antibodies exhibit binding specificity to a specific antigen, immunoglobulins include both antibodies and other antibody-like molecules that lack antigen specificity. Polypeptides of the latter kind are, for example, produced at low levels by the lymph system and at increased levels by myelomas. The present invention includes monoclonal antibodies (and binding fragments thereof) that are completely recombinant, in other words, where the complementarity determining regions (CDRs) are genetically spliced into a human antibody backbone, often referred to as veneering an antibody. Thus, in certain aspects the monoclonal antibody is a fully synthesized antibody. In certain embodiments, the monoclonal antibodies (and binding fragments thereof) can be made in bacterial or eukaryotic cells, including plant cells.

As used herein, the term "antibody fragment" refers to a portion of a full-length antibody, generally the antigen binding or variable region and include Fab, Fab', F(ab')$_2$, Fv and scFv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments which are capable of cross-linking antigen, and a residual other fragment (which is termed pFc'). As used herein, "functional fragment" with respect to antibodies, refers to Fv, F(ab) and F(ab')$_2$ fragments.

As used herein, the "Fv" fragment is the minimum antibody fragment that contains a complete antigen recognition and binding site. This region consists of a dimer of one heavy and one light chain variable domain in a tight, non-covalent association ($V_H$—$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The Fab fragment, also designated as F(ab), also contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. Fab'-SH is the designation herein for Fab' in which the cysteine residue(s) of the constant domains have a free thiol group. F(ab') fragments are produced by cleavage of the disulfide bond at the hinge cysteines of the F(ab')$_2$ pepsin digestion product. Additional chemical couplings of antibody fragments are known to those of ordinary skill in the art.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond. While the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., J. Mol. Biol. 186, 651-66, 1985); Novotny and Haber, Proc. Natl. Acad. Sci. USA 82 4592-4596 (1985), relevant portions incorporated herein by reference.

As used herein, an "isolated" antibody is one that has been identified and separated and/or recovered from a component of the environment in which it was produced. Contaminant components of its production environment are materials, which would interfere with diagnostic or therapeutic uses for the antibody, and may include enzymes, hormones, and other proteinaceous or nonproteinaceous solutes. In certain embodiments, the antibody will be purified as measurable by at least three different methods: 1) to greater than 50% by weight of antibody as determined by the Lowry method, such as more than 75% by weight, or more than 85% by weight, or more than 95% by weight, or more than 99% by weight; 2) to a degree sufficient to obtain at least 10 residues of N-terminal or internal amino acid sequence by use of a spinning cup sequentator, such as at least 15 residues of sequence; or 3) to homogeneity by SDS-PAGE under reducing or non-reducing conditions using Coomasie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, the term "antibody mutant" refers to an amino acid sequence variant of an antibody wherein one or more of the amino acid residues have been modified. Such mutants necessarily have less than 100% sequence identity or similarity with the amino acid sequence having at least 75% amino acid sequence identity or similarity with the amino acid sequence of either the heavy or light chain variable domain of the antibody, such as at least 80%, or at least 85%, or at least 90%, or at least 95, 96, 97, 98, or 99%.

As used herein, the term "variable" in the context of variable domain of antibodies, refers to the fact that certain portions of the variable domains differ extensively in sequence among antibodies and are used in the binding and specificity of each particular antibody for its particular antigen. However, the variability is not evenly distributed through the variable domains of antibodies. It is concentrated in three segments called complementarity determining regions (CDRs) also known as hypervariable regions both in the light chain and the heavy chain variable domains. There are at least two techniques for determining CDRs: (1) an approach based on cross-species sequence variability (i.e., Kabat et al., Sequences of Proteins of Immunological Interest (National Institute of Health, Bethesda, Md. 1987); and (2) an approach based on crystallographic studies of antigen-antibody complexes (Chothia, C. et al. (1989), Nature 342: 877), or both, that is Chothia plus Kabat. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat et al.) The constant domains are not involved directly in binding an antibody to an antigen, but exhibit various effector function, such as participation of the antibody in antibody-dependent cellular toxicity.

The light chains of antibodies (immunoglobulin) from any vertebrate species can be assigned to one of two clearly distinct types, called kappa and lambda, based on the amino sequences of their constant domain.

Depending on the amino acid sequences of the constant domain of their heavy chains, "immunoglobulins" can be assigned to different classes. There are at least five (5) major classes of immunoglobulins: IgA, IgD, IgE, IgG and IgM, and several of these may be further divided into subclasses (isotypes), e.g., IgG-1, IgG-2, IgG-3 and IgG4; IgA-1 and IgA-2. The subunit structures and three-dimensional configurations of different classes of immunoglobulins are well known.

As used herein, the term "monoclonal antibody" refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations, which typically include different antibodies directed against different determinants (epitopes), each monoclonal antibody is directed against a single determinant on the antigen. In additional to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the presently disclosed and claimed invention may be made by the hybridoma method first described by Kohler and Milstein, Nature 256, 495 (1975), relevant portions incorporated herein by reference.

All monoclonal antibodies utilized in accordance with the presently disclosed and claimed invention will be either (1) the result of a deliberate immunization protocol, as described in more detail herein below; or (2) the result of an immune response that results in the production of antibodies naturally in the course of a disease or cancer.

The uses of the monoclonal antibodies of the presently disclosed and claimed invention may require administration of such or similar monoclonal antibody to a subject, such as a human. However, when the monoclonal antibodies are produced in a non-human animal, such as a rodent or chicken, administration of such antibodies to a human patient will normally elicit an immune response, wherein the immune response is directed towards the antibodies themselves. Such reactions limit the duration and effectiveness of such a therapy. In order to overcome such problem, the monoclonal antibodies of the presently disclosed and claimed invention can be "humanized", that is, the antibodies are engineered such that antigenic portions thereof are removed and like portions of a human antibody are substituted therefore, while the antibodies' affinity for specific ELTD1 is retained. This engineering may only involve a few amino acids, or may include entire framework regions of the antibody, leaving only the complementarity determining regions of the antibody intact. Several methods of humanizing antibodies are known in the art and are disclosed in U.S. Pat. No. 6,180,370, issued to Queen et al on Jan. 30, 2001; U.S. Pat. No. 6,054,927, issued to Brickell on Apr. 25, 2000; U.S. Pat. No. 5,869,619, issued to Studnicka on Feb. 9, 1999; U.S. Pat. No. 5,861,155, issued to Lin on Jan. 19, 1999; U.S. Pat. No. 5,712,120, issued to Rodriquez et al on Jan. 27, 1998; and U.S. Pat. No. 4,816,567, issued to Cabilly et al on Mar. 28, 1989, relevant portions incorporated herein by reference.

Humanized forms of antibodies are chimeric immunoglobulins, immunoglobulin chains or fragments thereof (such as Fab, Fab', F(ab')$_2$, Fv, scFv or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., 1986; Riechmann et al., 1988; Verhoeyen et al., 1988), by substituting nonhuman (i.e. rodent, chicken) CDRs or CDR sequences for the corresponding sequences of a human antibody. (See also U.S. Pat. No. 5,225,539.) In some instances, $F_v$ framework residues of the human immunoglobulin are replaced by corresponding non-human residues from the donor antibody. Humanized antibodies can also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin.

The presently disclosed and claimed invention further includes the use of fully human monoclonal antibodies against ELTD1. Fully human antibodies essentially relate to antibody molecules in which the entire sequence of both the light chain and the heavy chain, including the CDRs, arise from human genes. Such antibodies are termed "human antibodies" or "fully human antibodies" herein. Human monoclonal antibodies can be prepared by the trioma technique; the human B-cell hybridoma technique (see Kozbor, et al., Hybridoma, 2:7 (1983)) and the EBV hybridoma technique to produce human monoclonal antibodies (see Cole, et al., PNAS 82:859 (1985)). Human monoclonal antibodies may be utilized in the practice of the presently disclosed and claimed invention and may be produced by using human hybridomas (see Cote, et al., PNAS 80:2026 (1983)) or by transforming human B-cells with Epstein Barr Virus in vitro (see Cole, et al., 1985), relevant portions incorporated herein by reference.

In addition, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example but not by way of limitation, in U.S. Pat. Nos. 5,545,807; 5,545,806; 5,569,825; 5,625,126; 5,633,425; 5,661,016, and in Marks et al., J Biol. Chem. 267:16007, (1992); Lonberg et al., Nature, 368:856 (1994); Morrison, 1994; Fishwild et al., Nature Biotechnol. 14:845 (1996); Neuberger, Nat. Biotechnol. 14:826 (1996); and Lonberg and Huszar, Int Rev Immunol. 13:65 (1995), relevant portions incorporated herein by reference.

A method for producing an antibody of interest, such as a human antibody, is disclosed in U.S. Pat. No. 5,916,771, issued to Hori et al. on Jun. 29, 1999, and incorporated herein by reference. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

As used herein, the term "treatment" refers to both therapeutic treatment and prophylactic or preventative measures. Those in need of treatment include those already with the disorder as well as those in which the disorder is to be prevented.

As used herein, the term "disorder" refers to any condition that would benefit from treatment with the polypeptide. This includes chronic and acute disorders or diseases including those infectious or pathological conditions that predispose the mammal to the disorder in question.

An antibody or antibody fragment can be generated with an engineered sequence or glycosylation state to confer preferred levels of activity in antibody dependent cellular cytotoxicity (ADCC), antibody-dependent cellular phagocytosis (ADCP), antibody-dependent neutrophil phagocytosis (ADNP), or antibody-dependent complement deposition (ADCD) functions as measured by bead-based or cell-based assays or in vivo studies in animal models.

Alternatively or additionally, it may be useful to combine amino acid modifications with one or more further amino acid modifications that alter complement component C1q binding and/or the complement dependent cytotoxicity (CDC) function of the Fc region of an IL-23p19 binding molecule. The binding polypeptide of particular interest may be one that binds to C1q and displays complement dependent cytotoxicity. Polypeptides with pre-existing C1q binding activity, optionally further having the ability to mediate CDC may be modified such that one or both of these activities are enhanced. Amino acid modifications that alter C1q and/or modify its complement dependent cytotoxicity function are described, for example, in WO/0042072, which is hereby incorporated by reference.

An Fc region of an antibody can be designed to alter the effector function, e.g., by modifying C1q binding and/or FcγR binding and thereby changing complement dependent cytotoxicity (CDC) activity and/or antibody-dependent cell-mediated cytotoxicity (ADCC) activity. These "effector functions" are responsible for activating or diminishing a biological activity (e.g., in a subject). Examples of effector functions include, but are not limited to: C1q binding; CDC; Fc receptor binding; ADCC; phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of an antibody with improved C1q binding and improved FcγRIII binding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

A single chain variable fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen-binding domain as a single peptide. Alternatively, scFv can be created directly from subcloned heavy and light chains derived from a hybridoma or B cell. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alanine, serine and glycine. However, other residues can function as well. Phage display can be used to rapidly select tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) is displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the VH C terminus and an abundance of arginines and prolines at other positions as the only common features of the selected tethers. In certain embodiments, the antibody fragments are further modified to increase its serum half-life by using modified Fc regions or mutations to the various constant regions, as are known in the art.

Multiple Sclerosis. Multiple Sclerosis (MS) is one of the most common diseases of the central nervous system (brain and spinal cord). It is an inflammatory condition associated with demyelination, or loss of the myelin sheath. Myelin, a fatty material that insulates nerves, acts as insulator in allowing nerves to transmit impulses from one point to another. In MS, the loss of myelin is accompanied by a disruption in the ability of the nerves to conduct electrical impulses to and from the brain and this produces the various symptoms of MS, such as impairments in vision, muscle coordination, strength, sensation, speech and swallowing, bladder control, sexuality and cognitive function. The plaques or lesions where myelin is lost appear as hardened, scar-like areas. These scars appear at different times and in different areas of the brain and spinal cord, hence the term "multiple" sclerosis, literally meaning many scars.

Currently, there is no single laboratory test, symptom, or physical finding that provides a conclusive diagnosis of MS. To complicate matters, symptoms of MS can easily be confused with a wide variety of other diseases such as acute disseminated encephalomyelitis, Lyme disease, HIV-associated myelopathy, HTLV-I-associated myelopathy, neurosyphilis, progressive multifocal leukoencephalopathy, systemic lupus erythematosus, polyarteritis nodosa, Sjogren's syndrome, Behcet's disease, sarcoidosis, paraneoplastic syndromes, subacute combined degeneration of cord, subacute myelo-optic neuropathy, adrenomyeloneuropathy, spinocerebellar syndromes, hereditary spastic paraparesis/primary lateral sclerosis, strokes, tumors, arteriovenous malformations, arachnoid cysts, Arnold-Chiari malformations, and cervical spondylosis. Consequently, the diagnosis of MS must be made by a process that demonstrates findings that are consistent with MS, and also rules out other causes.

Retinopathy. Retinopathy is any damage to the retina of the eyes, which may cause vision impairment. Retinopathy often refers to retinal vascular disease, or damage to the retina caused by abnormal blood flow. Age-related macular degeneration is technically included under the umbrella term retinopathy but is often discussed as a separate entity. Retinopathy, or retinal vascular disease, can be broadly categorized into proliferative and non-proliferative types. Frequently, retinopathy is an ocular manifestation of systemic disease as seen in diabetes or hypertension. Diabetes is the most common cause of retinopathy in the U.S. as of 2008. Diabetic retinopathy is the leading cause of blindness in working-aged people. It accounts for about 5% of blindness worldwide and is designated a priority eye disease by the World Health Organization.

Many people often do not have symptoms until very late in their disease course. Patients often become symptomatic when there is irreversible damage. Symptoms are usually not painful and can include: vitreous hemorrhage, "floaters," or small objects that drift through the field of vision, decreased visual acuity, and "curtain falling" over eyes.

The development of retinopathy can be broken down into proliferative and non-proliferative types. Both types cause disease by altering the normal blood flow to the retina through different mechanisms. The retina is supplied by small vessel branches from the central retinal artery. Proliferative retinopathy refers to damaged caused by abnormal blood vessel growth. Normally, angiogenesis is a natural part of tissue growth and formation. When there is an unusually high or fast rate of angiogenesis, there is an overgrowth of blood vessels called neovascularization. In the non-proliferative type, abnormal blood flow to the retina occurs due to direct damage or compromise of the blood vessels themselves. Many causes of retinopathy may cause both proliferative and non-proliferative types, though some causes are more associated one type.

Tissue Regeneration. Regeneration in humans is the regrowth of lost tissues or organs in response to injury. This is in contrast to wound healing, which involves closing up the injury site with a scar. Some tissues such as skin and large organs including the liver regrow quite readily, while others have been thought to have little or no capacity for regeneration. However ongoing research, particularly in the heart and lungs, suggests that there is hope for a variety of tissues and organs to eventually become regeneration-capable.

There are two type of tissue regeneration—natural regeneration and induced regeneration. The former involves tissues that exhibit a natural ability to regenerate without outside intervention, such as heart, endometrium, fingers (fingertip), kidney, liver and toes. The latter involves external influence to produce or accentuate regeneration, such as de-differentiating injury site cells, transplanting stem cells, implanting lab-grown tissues, and implanting bioartificial tissues.

Cancer. Cancer is a group of diseases involving abnormal cell growth with the potential to invade or spread to other parts of the body. These contrast with benign tumors, which do not spread to other parts of the body. Possible signs and symptoms include a lump, abnormal bleeding, prolonged cough, unexplained weight loss and a change in bowel movements. While these symptoms may indicate cancer, they may have other causes. Over 100 types of cancers affect humans.

Antibodies against non-ELTD1 angiogenic targets have been approved for use in humans for the treatment of various cancers including metastatic colorectal cancer, first-line non-squamous non-small cell lung cancer, recurrent glioblastoma multiforme, metastatic renal cell carcinoma, persistent, recurrent, or metastatic cervical cancer, and epithelial ovarian, fallopian tube, or primary peritoneal cancer.

By way of explanation, the antibodies, fragments, and scFv antibodies taught herein can be used for cancer therapy by blocking tumor angiogenesis. The antibodies of the present invention (polyclonal, monoclonal, and binding fragments thereof) inhibit angiogenesis by reducing neovascularization in a tumor (or cancer) to a level that is at least 10% lower than a level of angiogenesis in a corresponding control tissue, and in some cases at least 15%, 20%, 25%, 30%, 35%, 40%, 45%, 50%, 55%, 60%, 65%, 70%, 75%, 80%, 85%, 90%, 95%, or 99% lower than the level of angiogenesis in an equivalent control tissue. A reduced level of angiogenesis does not mean an absolute absence of angiogenesis, rather a reduction is the extent or level of neovascularization is sufficient. Angiogenesis can be determined using methods known to the skilled artisan, including, e.g., in vitro and in vivo model, including counting the number of blood vessels and/or the number of blood vessel branch points, as discussed herein and in the examples. Therefore, the novel anti-ELTD1 humanized antibody with enhanced therapeutic efficacy will benefit cancer patients.

Cancer can spread from its original site by local spread, lymphatic spread to regional lymph nodes or by hematogenous spread via the blood to distant sites, known as metastasis. When cancer spreads by a hematogenous route, it usually spreads all over the body. However, cancer 'seeds' grow in certain selected site only ('soil') as hypothesized in the soil and seed hypothesis of cancer metastasis. The symptoms of metastatic cancers depend on the tumor location and can include enlarged lymph nodes (which can be felt or sometimes seen under the skin and are typically hard), enlarged liver or enlarged spleen, which can be felt in the abdomen, pain or fracture of affected bones and neurological symptoms.

Many treatment options for cancer exist. The primary ones include surgery, chemotherapy, radiation therapy, hormonal therapy, targeted therapy and palliative care. Which treatments are used depends on the type, location and grade of the cancer as well as the patient's health and preference. The treatment intent may or may not be curative.

The therapeutic methods of the disclosure (which include prophylactic treatment) in general include administration of a therapeutically effective amount of the compositions described herein to a subject in need thereof, including a mammal, particularly a human. Such treatment will be suitably administered to subjects, particularly humans, suffering from, having, susceptible to, or at risk for cancer, or having a symptom thereof. Determination of those subjects "at risk" can be made by any objective or subjective determination by a diagnostic test or opinion of a subject or health care provider (e.g., genetic test, enzyme or protein marker, marker (as defined herein), family history, and the like).

The cancer may be a carcinoma, sarcoma, lymphoma, leukemia, melanoma, mesothelioma, multiple myeloma, or seminoma. In some embodiments, the cancer is of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the cancer is leukemia, non-small cell lung cancer, colon cancer, CNS cancer, melanoma, ovarian cancer, renal cancer, breast cancer, or prostate cancer.

In one embodiment, the disclosure provides a method of monitoring treatment progress. The method includes the step of determining a level of changes in hematological parameters and/or cancer stem cell (CSC) analysis with cell surface proteins as diagnostic markers (which can include, for example, but are not limited to CD34, CD38, CD90, and CD117) or diagnostic measurement (e.g., screen, assay) in a subject suffering from or susceptible to a disorder or symptoms thereof associated with cancer (e.g., leukemia) in which the subject has been administered a therapeutic amount of a composition as described herein. The level of marker determined in the method can be compared to known levels of marker in either healthy normal controls or in other afflicted patients to establish the subject's disease status. In preferred embodiments, a second level of marker in the subject is determined at a time point later than the determination of the first level, and the two levels are compared to monitor the course of disease or the efficacy of the therapy. In certain embodiments, a pre-treatment level of marker in the subject is determined prior to beginning treatment according to the methods described herein; this pre-treatment level of marker can then be compared to the level of marker in the subject after the treatment commences, to determine the efficacy of the treatment.

To treat cancers using the methods and compositions of the present disclosure, one would generally contact a tumor cell or subject with a compound and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the compound and the other includes the other agent.

Alternatively, the antibody may precede or follow the other treatment by intervals ranging from minutes to weeks. One would generally ensure that a significant period of time did not expire between each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

Antibody Conjugates. Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are often used as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

Example 1

First, extracellular domain of mouse ELTD1 gene encoding residues from Glu20 to Leu455 (574 aa) was successfully amplified by reverse transcription polymerase chain reaction (RT-PCR) using the RNA from a bEnd3 (mouse brain endothelial polyoma middle T antigen transformed cell). The extracellular domain of human ELTD1 gene was amplified by RT-PCR using the RNA prepared from HUVECs. The sequence of these two genes was checked by Sanger sequencing. The inventors have successfully cloned these two genes into a mammalian expression vector to express the mouse recombinant protein of the ELTD1 fragment, Glu20-Leu455 (574 aa) (Favara et al., "A review of ELTD1, a pro-angiogenic adhesion GPCR", Biochem Soc Trans (2014) 42 (6): 1658-1664) and human ELTD1 fragment fused with $C_K$ (human immunoglobulin κ light chain constant domain). After transfection to a Human Embryonic Kidney (HEK) 293F over-expression system, the recombinant proteins were purified by affinity chromatography using the KappaSelect resin (GE Healthcare).

The proteins were immunized into chickens. Afterward chicken scFv (single chain Fv) library was generated using the immunized chicken as described. Then antibodies specific to extracellular domain of mouse ELTD1 were selected not only from the chicken scFv library but also human naive and synthetic libraries (Barbas, C. F., 2001). mRNA was prepared from B cells and the antibody was constructed from a library obtained from two chickens from each group of the selected clones.

Targeting ELTD1 with a monoclonal antibody affects several genes that are associated with either multiple sclerosis (MS), retinopathy or tissue regeneration. RNA-seq data was initially obtained from a human glioblastoma (GBM) xenograft nude mouse model, either from tumor tissues that were untreated or treated with a monoclonal antibody against the extracellular domain for ELTD1.

The antibody binding procedure was as follows: Ag coating on a microtiter plate nM N-hCk-control 0.5 µg/ml N-hCk-Control (25 kDa) 15 nM N-hCk-mELTD 1: 1 µg/ml N-hCk-mouse ELTD 1 (60 kDa) 15 nM N-hCk-hELTD 1: 1 µg/ml N-hCk-human ELTD1 (65 kDa) Blocking w/3% BSA in PBS Ab dilution: 100 nM-0.001 nM, 1/10 serial dilution, 6 points 2nd Ab: a-rabbit Fc-HRP Substrate: ABTS Reading @405 nm.

The N17 clone was selected to generate the monoclonal antibody against human ELTD1 ECD recombinant protein (FIG. 3). The N17 clone binds to both human and mouse ELTD1, but the affinity is higher toward human ELTD 1 (FIG. 4).

Preparation of recombinant extracellular domain of ELTD1 human Ckappa fusion protein. To construct extracellular domain of human ELTD1 and mouse ELTD1 expression vectors, genes encoding the human ELTD1 (Glu20-Leu406) and mouse ELTD1 (Glu20-Leu455) were chemically synthesized (Genscript, Picataway, N.J., USA). The genes were subcloned into the modified pCEP4 vector encoding $C_{kappa}$ domain (human immunoglobulin kappa light chain constant domain) at the 5' region as reported previously [Lee Y, Kim H, Chung J. An antibody reactive to the Gly63-Lys68 epitope of NT-proBNP exhibits O-glycosylation-independent binding. Exp Mol Med. 2014; 46:e114].

The expression vectors encoding extracellular domain of human ELTD1 and mouse ELTD1 were transfected into HEK293F cells (Invitrogen, Carlsbad, CA, USA) using 25-kDa linear polyethyleneimine (Polyscience, Warrington, PA, USA), as reported previously [Boussif O, Lezoualc'h F, Zanta M A, Mergny M D, Scherman D, Demeneix B, et al. A versatile vector for gene and oligonucleotide transfer into cells in culture and in vivo: polyethylenimine. Proc Natl Acad Sci USA. 1995; 92(16):7297-301]. Human and mouse ELTD1 $C_{kappa}$ fusion proteins were purified from the culture supernatants by affinity chromatography using KappaSelect resin (GE Healthcare) according to the manufacturer's instructions.

Generation of anti-ELDT1 antibody. White leghorn chickens were immunized with human ELTD1 $C_{kappa}$ fusion proteins. And a phage-displayed chicken single-chain variable fragment (scFv) library was constructed using total RNA isolated from the bone marrow, spleen, and bursa of Fabricius of immunized chickens, as described previously [Andris-Widhopf J, Rader C, Steinberger P, Fuller R, Barbas C F, 3rd. Methods for the generation of chicken monoclonal antibody fragments by phage display. J Immunol Methods. 2000; 242(1-2):159-81]. Positive clones were enriched by biopanning and screened in a phage enzyme immunoassay, as described previously [Barbas, C. F. 2001. Phage Display: A Laboratory Manual. Cold Spring Harbor Laboratory Press, Cold Spring Harbor, NY]. The phage clones showing cross reactivity against human and mouse ELTD1 were selected and their nucleotide sequences were determined by sanger sequencing.

The gene of selected scFv clone was subcloned into a modified mammalian expression vector encoding the hinge region of human IgG1 and the CH2-CH3 domains of rabbit IgG at the 3' region as reported previously [Han J, Lee J H, Park S, Yoon S, Yoon A, Hwang D B, et al. A phosphorylation pattern-recognizing antibody specifically reacts to RNA polymerase II bound to exons. Exp Mol Med. 2016; 48(11):e271]. The expression vectors encoding anti-ELTD1 bivalent scFv Fc-fusion, which has two scFv molecules that are dimerized through disulfide bonding, was transfected into HEK293F cells (Invitrogen) as described above. The bivalent scFv Fc-fusion protein was purified from the culture supernatants of transiently transfected HEK293F cells using protein A Sepharose column (Repligen, Waltham, MA, USA) according to the manufacturer's instructions. In one example, the monoclonal antibody is a bivalent scFv Fc-fusion antibody, which scFvs can be the same or different.

Enzyme immunoassay. The wells of a 96-well microtiter plate (Corning Inc., Corning, NY, USA) were coated with human ELTD1 or mouse ELTD1 $C_{kappa}$ fusion protein in coating buffer (0.1M $NaHCO_3$, pH 8.6) and then blocked with 3% (w/v) BSA in phosphate-buffered saline (PBS). After incubation with serially 10-fold diluted anti-ELTD1 scFv-rFc fusion protein (0.01-100 nM), horseradish peroxidase (HRP)-conjugated goat anti-rabbit IgG (Fc specific) (Jackson Immuno Research, Inc., West Grove, PA, USA) were added to each well. After washing with 0.05% (v/v) Tween 20 in PBS (PBST), ABTS HRP substrate solution (Thermo Scientific Pierce, Rockford, IL, USA) was added and the absorbance was measured at 405 nm with a Multiskan Ascent microplate reader (LabSystems, Helsinki, Finland).

The following sequences include the nucleic acid and amino acid sequences for the various light and heavy chains of the monoclonal antibodies, in these specific cases made into scFvs. Further, the Complementarity Determining Regions (CDRs) were determined using the software available from IMGT.org using Kabat rules. The tables that follow include alternative CDR sequences comparing Kabat, Clothia, and IMGT rules, all of which can be used with the present invention to modify an antibody backbone (e.g., a human antibody) with the CDRs disclosed herein.

Anti-ELTD1 scFv N5, Nucleotide sequence, SEQ ID NO: 1, a variable light chain sequence, a linker in bold, and variable heavy chain sequence underlined.

GCCCTGACTCAGCCGTCCTCGGTGTCAGCAAACCCGGGAGAAACCGTCA

AGATCACCTGCTCCGGGAGTAGTGGCAGCTACTATGGCTGGCACCAGCA

GAAGTCTCCTGGCAGTGCCCCTGTCACTCTGATCTATGACAACACCAAC

AGACCCTCGGACATCCCTTCACGATTCTTCGGTTCCAAATCCGGTTCCA

CAGCCACATTAACCATCACTGGGGTCCAAGCCGACGACGAGGCTGTCTA

TTACTGTGGGAGCTGGGACAGCAGCAGTGGTGCTGGTATATTTGGGGCC

GGGACAACCCTGACCGTCCTAGGTCAGTCCTCTAGATCTTCCAGCGGTG

GTGGCAGCTCCGGTGGTGGCGGTTCCGCCGTGACGTTGGACGAGTCCGG

GGGCGGCCTCCAGACGCCCGGAGGAGCGCTCAGCCTCGTCTGCAAGGCC

TCCGGGTTCACCTTCAGCAGTTACGCCATGAACTGGGTGCGACAGGCGC

CCGGCAAGGGGCTGGAGTGGGTCGCAGCTATTAGCAGTGATGGTAGTAG

CACAGGATATGGGCCGGCGGTGGAGGGCCGTGCCACCATCTCGAGGGAC

AACGGGCAGAGCACAGTGAGGCTGCAGCTGAACAACCTCAGGGCTGAGG

ACACCGGCACCTACTACTGCGCCAAAAATGCTTGTACTTACGGTAGTGG

TTATTGTGGTTGGAGTGGTGCTGGTGGTATCGACGCATGGGGCCACGGG

ACCGAAGTCATCGTCTCCTCC

Anti-ELTD1 scFv N5, Amino acid sequence, SEQ ID NOS: 2, 3, and 4 including a variable light chain sequence, a linker in bold, and a variable heavy chain sequence italics, respectively. CDR1, CDR2, and CDR3 are double underlined and are listed in order from the amino to the carboxy terminus.

ALTQPSSVSANPGETVKITC<u>SGSSGSYYG</u>WHQQKSPGSAPVTLIY<u>DNTNRPS</u>DIPSRFFGSKS
GSTATLTITGVQADDEAVYYC<u>GSWDSSSGAGI</u>FGAGTTLTVL (variable light chain CDRS 1,
2 and 3 are

SEQ ID NO: 25

<u>SGSSGSYYG</u>,

SEQ ID NO: 26

<u>DNTNRPS</u>,

SEQ ID NO: 27

<u>GSWDSSSGAGI</u>, respectively)

GQSSRSSSGGGSSGGGGS

AVTLDESGGGLQTPGGALSLVCKASGFTFS<u>SYAMN</u>WVRQAPGKGLEWVA<u>AISSDGSSTGY
GPAVEG</u>RATISRDNGQSTVRLQLNNLRAEDTGTYYCAK<u>NACTYGSGYCGWSGAGGIDA</u>WGHGTE
VIVSS (variable heavy chain CDRS 1, 2 and 3 are

SEQ ID NO: 28

<u>SYAMN</u>,

SEQ ID NO: 29

<u>AAISSDGSSTGYGPAVEG</u>,

SEQ ID NO: 30

<u>NACTYGSGYCGWSGAGGIDA</u> respectively)

Anti-ELTD1 scFv N7, Nucleotide sequence, SEQ ID NO:5, a variable light chain sequence, a linker in bold, and variable heavy chain sequence underlined.

GCCCTGACTCAGCCGTCCTCGGCGTCAGCAAACCCGGGAGAAACCGTCG

AGATCACCTGCTCCGGGGGTTACAGCGGCTATGGCTGGTTCCAGCAGAA

GTCTCCTGGCAGTGCCCCTGTCACTCTGATCTATGAAAACGACAAGAGA

CCCTCGGACATCCCTTCACGATTCTCCGGTTCCAAATCCGGCTCCACGG

GCACATTAACCATCACTGGGGTCCAAGCCGACGACGAGGCTGTCTATTT

CTGTGGGAGTGCAGACAGGAGTAATAATGTGGGTATATTTGGGGCCGGG

ACAACCCTGACCGTCCTA**GGTCAGTCCTCTAGATCTTCCGGCGGTGGTG
GCAGCTCCGGTGGTGGCGGTTCC**<u>GCCGTGACGTTGGACGAGTCCGGGGG</u>

-continued
<u>CGGCCTCCAGACGCCCGGAGGAGCGCTCAGCCTCGTCTGCAAGGCCTCC

GGGTTCGACTTCAGCAGTTACGCCATGAACTGGGTGCGACAGGCGCCCG

GCAAGGGGCTGGAGTGGGTCGCTGCTATTAGTGACACTGGTAGTGGCAC

AGGATACGGGGCGGCGGTGAAGGGCCGTGCCACCATCTCGAGGGACAAC

GGGCAGAGCACAGTGAGGCTGCAGCTGAACAACCTCAGGGCAGAGGACA

CCGGCATCTACTTCTGCGCCAAAGATGCTGGTTATGCTGCTGGTTGGGG

TGCTGCTGGGAGCATCGACGCATGGGCCACGGGACCGAAGTCATCGTC

TCCTCC</u>

Anti-ELTD1 scFv N7, Amino acid sequence, SEQ ID NOS:6, 7, 8, including a variable light chain sequence, a linker in bold, and a variable heavy chain sequence italics, respectively. CDR1, CDR2, and CDR3 are double underlined.

ALTQPSSASANPGETVEITC<u>SGGYSGYG</u>WFQQKSPGSAPVTLIY<u>ENDKRPS</u>DIPSRFSGSKSGS
TGTLTITGVQADDEAVYFC<u>GSADRSNNVGI</u>FGAGTTLTVL (variable light chain CDRS 1,
2 and 3 are:

SEQ ID NO: 31

<u>SGGYSGYG</u>,

SEQ ID NO: 32

<u>ENDKRPS</u>,

SEQ ID NO: 33

<u>GSADRSNNVGI</u>, respectively)

GQSSRSSGGGGSSGGGGS

*AVTLDESGGGLQTPGGALSLVCKASGFDFS<u>SYAMN</u>WVRQAPGKGLEWVA<u>AISDTGSGTGYAAV
KG</u>RATISRDNGQSTVRLQLNNLRAEDTGIYFCAK<u>DAGYAAGWGAAGSIDA</u>WGHGTEVIVSS* (variable
heavy chain CDRS 1, 2 and 3 are:

SEQ ID NO: 34

<u>SYAMN</u>,

SEQ ID NO: 35

<u>AISDTGSGTGYGAAVKG</u>,

SEQ ID NO: 36

<u>DAGYAAGWGAAGSIDA</u>, respectively)

Anti-ELTD1 scFv N11, Nucleotide sequence, SEQ ID NO:9, a variable light chain sequence, a linker in bold, and variable heavy chain sequence underlined.

GCCCTGACTCAGCCGTCCTCGGTGTCAGCAAACCTGGGAGGAACCGTCA
AGATCACCTGCTCCGGGGGTAGTGGCAGCTACGGCTGGTTCCAGCAGAA
GGCACCTGGCAGTGCCCCTGTCACTCTGATCTATGACAACACCAACAGA
CCCTCGAACATCCCTTCACGATTCTCCGGTTCCACATCTGGCTCCACAA
GCACATTAGCCATCACTGGGGTCCAAGCCGACGACGAGGCTGTCTATTA
CTGTGGGAGTGAAGACATCAGCTATATCGGTATATTTGGGGCCGGGACA
ACCCTGACCGTCCTAGGTCAGTCCTCTAGATCTTCCGGCGGTGGTGGCA
GCTCCGGTGGTGGCGGTTCCGCCGTGACGTTGGACGAGTCCGGGGGCGG
CCTCCAGACGCCCGGAGGAGGGCTCAGCCTCGTCTGCAAGGCCTCCGGC
TTCACCTTCAGCAGTTTCTACATGTTCTGGGTGCGCCAGGCGCCCGGCA
AGGGGCTGGAATACGTCGCAGCTATTAGCAACACTGGTAGTGGCACAGA
CTACGGGGCGGCGGTGCAGGGCCGTGCCACCATCTCGAGGGACAACGGG
CAGAGCACAGTGAGGCTGCAGCTGAACAACCTCAGGGCTGAGGACACCG
CCACCTACTACTGCGCCAAAGCTGCTGCTGGTTGTACTGGTTGTGGTGG
TGCTGGTAGTATCGACGCATGGGGCCACGGGACCGAAGTCATCGTCTCC
TCC

Anti-ELTD1 scFv N15, Nucleotide sequence, SEQ ID NO: 13, a variable light chain sequence, a linker in bold and variable heavy chain sequence underlined.

GCCCTGACTCAGCCGTCCTCGGTGTCAGCAAACCCAGGAGAAACCGTCA
AGATCACCTGCTCTGGGGGCAGCTATAGCTATGGCTGGTACCAGCAGAA
GGCACCTGGCAGTGCCCCTGTCACTGTGATCTATGACAACACCAACAGA
CCCTCGAACATCCCTTCACGATTCTCCGGTTCCACATCCGGCTCCACAG
CCACATTAACCATCACTGGGGTCCGAGCCGAGGACGAGGCTGTCTATTA
CTGTGGGAGTGCAGACAGCAGTTACATTGGTATATTTGGGGCCGGGACA
ACCCTGACCGTCCTAGGTCAGTCCTCTAGATCTTCCGGCGGTGGTGGCA
GCTCCGGTGGTGGCGGTTCCGCCGTGACGTTGGACGAGTCCGGGGGCGG
CCTCCAGACGCCCGGAGGAACGCTCAGCCTCGTCTGCAAGGCCTCCGGG
TTCACCTTCAGCAGCGTCAACATGTTCTGGATGCGACAGGCTCCAGGCA
AGGGGCTGGAGTTCGTTGCTGCTATTGGCAATGATGCTGGTGGCACAGA
CTACGGGGCGGCGGTGGATGGCCGTGCCACCATCTCGAGGGACAACGGG
CAGAGCACAGTGAGGCTGCAGCTGAACAACCTCAGGGCTGAGGACACCG
CCACCTACTACTGCGCCAAAGCTTCTGCTTGTAGTACTTCTGGTTGTGG
TGGTGCTGGTAGCATCGACGCATGGGGCCACGGGACCGAAGTCATCGTC
TCCTCC

Anti-ELTD1 scFv N11, Amino acid sequence, SEQ ID NOS:10, 11, 12, a variable light chain sequence, a linker in bold, and a variable heavy chain sequence italics, respectively. CDR1, CDR2, and CDR3 are double underlined.

Anti-ELTD1 scFv N15, Amino acid sequence, SEQ ID NOS:14, 15, 16, a variable light chain sequence, a linker in bold, and a variable heavy chain sequence italics, respectively. CDR1, CDR2, and CDR3 are double underlined.

ALTQPSSVSANLGGTVKITC<u>SGGSGSYG</u>WFQQKAPGSAPVTLIY<u>DNTNRPS</u>NIPSRFSGSTSG
STSTLAITGVQADDEAVYYC<u>GSEDISYIGI</u>FGAGTTLTVL (variable light chain CDRS 1,
2 and 3 are:

<u>SGGSGSYG</u>,                                                    SEQ ID NO: 37

<u>DNTNRPS</u>,                                                     SEQ ID NO: 38

SEQ ID NO: 39
<u>GSEDISYIGI</u>, respectively)

GQSSRSSGGGGSSGGGGS

*AVTLDESGGGLQTPGGGLSLVCKASGFTFS<u>SFYMF</u>WVRQAPGKGLEYVA<u>AISNTGSGTDYGAAVQ</u>*
*<u>G</u>RATISRDNGQSTVRLQLNNLRAEDTATYYCAK<u>AAAGCTGCGGAGSIDA</u>WGHGTEVIVSS* (variable heavy
chain CDRS 1, 2 and 3 are:

SEQ ID NO: 40
<u>SFYMF</u>,

SEQ ID NO: 41
<u>AISNTGSGTDYGAAVQG</u>,

SEQ ID NO: 42
<u>AAAGCTGCGGAGSIDA</u>, respectively)

ALTQPSSVSANPGETVKITC<u>SGGSYSYG</u>WYQQKAPGSAPVTVIY<u>DNTNRPS</u>NIPSRFSGSTSG
STATLTITGVRAEDEAVYYC<u>GSADSSYIGI</u>FGAGTTLTVL (variable light chain CDRS 1,
2 and 3 are:

SEQ ID NO: 43

<u>SGGSYSYG</u>,

SEQ ID NO: 44

<u>DNTNRPS</u>,

SEQ ID NO: 45

<u>GSADSSYIGI</u>, respectively)

GQSSRSSGGGGSSGGGGS

*AVTLDESGGGLQTPGGTLSLVCKASGFTFS<u>SVNMF</u>WMRQAPGKGLEFVA<u>AIGNDAGGTDYGAAV
DG</u>RATISRDNGQSTVRLQLNNLRAEDTATYYCAK<u>ASACSTSGCGGAGSIDA</u>WGHGTEVIVSS* (variable
heavy chain CDRS 1, 2 and 3 are:

SEQ ID NO: 46

<u>SVNMF</u>,

SEQ ID NO: 47

<u>AIGNDAGGTDYGAAVDG</u>,

SEQ ID NO: 48

<u>ASACSTSGCGGAGSIDA</u>, respectively)

Anti-ELTD1 scFv N16, Nucleotide sequence, SEQ ID NO:17, a variable light chain sequence, a linker in bold, and variable heavy chain sequence underlined.

GCCCTGACTCAGCCGTCCTCGGTGTCAGCAAACCTGGGAGGAACCGTCA

AGATCATCTGCTCCGGGGGTGGTGGCAGCTATGGCTGGTTCCAGCAGAA

GGCACCTGGCAGTGCCCCTGTCACTGTGATCTATGACAACAACAAGAGA

CCCTCGGACATCCCTTCACGATTCTCCGGTTCCAAATCCGGCTCCACGG

CCACATTAACCATCACTGGGGTCCGAGCCGAGGACGAGGCTGTCTATTA

CTGTGGGAGTGCAGACAACACCTATGTTGGTATATTTGGGGCCGGGACA

ACCCTGACCGTCCTA**GGTCAGTCCTCTAGATCTTCCAGCGGTGGTGGCA
GCTCCGGTGGTGGCGGTTCC**<u>GCCGTGACGTTGGACGAGTCCGGGGGCGG</u>

<u>CCTCCAGACGCCCGGAGGAACGCTCAGCCTCGTCTGCAAGGCCTCCGGG</u>

<u>TTCACCTTCAGCAGCGTCAACATGTTCTGGATGCGACAGGCTCCAGGCA</u>

<u>AGGGGCTGGGGTTCGTTGCTGCTATTGGCAATGATGCTGGTGGCACAGA</u>

<u>CTACGGGGCGGCGGTGGATGGCCGTGCCACCATCTCGAGGGACAACGGG</u>

<u>CAGAGCACAGTGAGGCTGCAGCTGAACAACCTCAGGGCTGAGGACACCG</u>

<u>CCACCTACTACTGCGCCAAAGCTTCTGCTTGTAGTACCTCTGGTTGTGG</u>

<u>TGGTGCTGGTAGCATCGACGCATGGGCCACGGGACCGAAGTCATCGTC</u>

<u>TCCTCC</u>

Anti-ELTD1 scFv N16, Amino acid sequence, SEQ ID NOS:18, 19, 20, a variable light chain sequence, a linker in bold, and a variable heavy chain sequence italics, respectively. CDR1, CDR2, and CDR3 are double underlined.

ALTQPSSVSANLGGTVKIIC<u>SGGGGSYG</u>WFQQKAPGSAPVTVIY<u>DNNKRPS</u>DIPSRFSGSKSG
STATLTITGVRAEDEAVYYC<u>GSADNTYVGI</u>FGAGTTLTVL (variable light chain CDRS 1,
2 and 3 are:

SEQ ID NO: 49

<u>SGGGGSYG</u>,

SEQ ID NO: 50

<u>DNNKRPS</u>,

SEQ ID NO: 51

<u>GSADNTYVGI</u>, respectively)

GQSSRSSGGGSSGGGGS

*AVTLDESGGGLQTPGGTLSLVCKASGFTFS<u>SVNMF</u>WMRQAPGKGLGFVA<u>AIGNDAGGTDYGAAV
DG</u>RATISRDNGQSTVRLQLNNLRAEDTATYYCAK<u>ASACSTSGCGGAGSIDA</u>WGHGTEVIVSS* (variable
heavy chain CDRS 1, 2 and 3 are:

SEQ ID NO: 52

<u>SVNMF</u>,

SEQ ID NO: 53

<u>AIGNDAGGTDYGAAVDG</u>,

SEQ ID NO: 54

<u>ASACSTSGCGGAGSIDA</u>, respectively)

Anti-ELTD1 scFv N17, Nucleotide sequence, SEQ ID NO:21, a variable light chain sequence, a linker in bold, and variable heavy chain sequence underlined.

GCCCTGACTCAGCCGTCCTCGGTGTCAGCAAACCCAGGAGAAACCGTCA
AGATCACCTGCTCCGGGGGTGGCAGCTATGGTTATGGCTGGTACCAGCA
GAAGGCACCTAGCAGTGCCCCTGTCACTGTGATTTGCTGGGATAACAAG
AGACCCTCGAACATCCCTTCACGATTCTCCGGTTCCACATCTGGCTCCA
CAGCCACATTAACCATCACTGGGGTCCAAGCCGAGGACGAGGCTGTCTA
TTTCTGTGGGAGTGCAGACAGCAGCGGTACTGCTGCTATATTTGGGCC
GGGACAAACCTGACCGTCCTA**GGTCAGTCCTCTAGATCTTCCAGCGGTG
GTGGCAGCTCCGGTGGTGGCGGTTCC**GCCGTGACGTTGGACGAGTCCGG

-continued
GGGCGGCCTCCAGACGCCCGGAGGAGCGCTCAGCCTCATCTGCAAGGCC
TCCGGGTTCGACTTCAGCAGTTACGCCATGAACTGGGTGCGACAGGCGC
CCGGCAAGGGGCTGGAGTGGGTCGCAAGTATTGATGATGGTGGTAGTGA
CACAACCTACGGGGCGGCGGTGAAGGGCCGCGCCACCGTCTCGAGGGAC
AACGGGCAGAGCACAGTGAGGCTGCAGTTGAACAACCTCAGGGCTGAGG
ACACCGGCACCTACTACTGCGCCAAAGATGCTAGTAGTGGTGGTGTTTG
GAGTGCTGCTGCTGGCATCGACGCATGGGGCCACGGGACCGAAGTCATC
GTCTCCTCC Anti-ELTD1 scFv N17, Amino acid sequence, SEQ ID NOS:22, 23, 24, a variable light chain sequence, a linker in bold, and a variable heavy chain sequence italics, respectively. CDR1, CDR2, and CDR3 are double underlined.

ALTQPSSVSANPGETVKITC<u>SGGGSYGYG</u>WYQQKAPSSAPVTVIC<u>WDNKRPS</u>NIPSRFSGSTS
GSTATLTITGVQAEDEAVYFC<u>GSADSSGTAAI</u>FGAGTNLTVL (variable light chain CDRS 1,
2 and 3 are:

SEQ ID NO: 55
<u>SGGGSYGYG</u>,

SEQ ID NO: 56
<u>WDNKRPS</u>,

SEQ ID NO: 57
<u>GSADSSGTAAI</u>, respectively)

GQSSRSSSGGGSSGGGGS

*AVTLDESGGGLQTPGGALSLICKASGFDFS<u>SYAMN</u>WVRQAPGKGLEWVA<u>SIDDGGSDTTYGAAV</u>*
*<u>KGRATVSRDNGQSTVRLQLNNLRAEDTGTYYCAK<u>DASSGGVWSAAAGIDA</u>WGHGTEVIVSS* (variable
heavy chain CDRS 1, 2 and 3 are:

SEQ ID NO: 58
<u>SYAMN</u>,

SEQ ID NO: 59
<u>SIDDGGSDTTYGAAVKG</u>,

SEQ ID NO: 60
<u>DASSGGVWSAAAGIDA</u>, respectively).

| Anti-ELTD1 N5 AA sequence | | | | | | | | | | | | | | | | |
|---|---|---|---|---|---|---|---|---|---|---|---|---|---|---|---|---|
| Residue | L21 | L22 | L23 | L24 | L25 | L26 | L27 | L28 | L29 | SEQ ID NO | L46 | L47 | L48 | L49 | L50 | L51 | L52 |
| N5-VL_Kabat | S | G | S | S | G | S | Y | Y | G | 25 | D | N | T | N | R | P | S |
| N6-VL_IMGT | | | | S | G | S | Y | | | 73 | D | N | T | | | | |
| N7-VL_Chothia | S | G | S | S | G | S | Y | Y | G | 79 | D | N | T | N | R | P | S |
| | | | | CDR-L1 | | | | | | | | | | CDR-L2 | | | |

| Residue | H26 | H27 | H28 | H29 | H30 | H31 | H32 | H33 | H34 | H35 | SEQ ID NO | H49 | H50 | H51 | H52 | H53 | H54 |
|---|---|---|---|---|---|---|---|---|---|---|---|---|---|---|---|---|---|
| N5-VH_Kabat | | | | | | S | Y | A | M | N | 28 | A | A | I | S | S | D |
| N5-VH_IMGT | G | F | T | F | S | S | Y | A | | | 76 | | | I | S | S | D |
| N5-VH_Chothia | G | F | T | F | S | S | Y | | | | 82 | | | | S | S | D |
| | | | | CDR-H1 | | | | | | | | | | CDR-H2 | | | |

| Residue | H97 | H98 | H99 | H100 | H101 | H102 | H103 | H104 | H105 | H106 | H107 | H108 | H109 | H110 | H111 | H112 | H113 |
|---|---|---|---|---|---|---|---|---|---|---|---|---|---|---|---|---|---|
| N5-VH_Kabat | | | N | A | C | T | Y | G | S | G | Y | C | G | W | S | G | A |
| N5-VH_IMGT | A | K | N | A | C | T | Y | G | S | G | Y | C | G | W | S | G | A |

| | | | | | | | | | | | | | | |
|---|---|---|---|---|---|---|---|---|---|---|---|---|---|---|
| N5-VH_Chothia | | N | A | C | T | Y | G | S | G | Y | C | G | W | S | G | A |
| | | | | | | | CDR-H3 | | | | | | | | |

Anti-ELTD1 N5 AA sequence

| Residue | SEQ ID NO | L85 | L86 | L87 | L88 | L89 | L90 | L91 | L92 | L93 | L94 | L95 | L96 | L97 | SEQ ID NO |
|---|---|---|---|---|---|---|---|---|---|---|---|---|---|---|---|
| N5-VL_Kabat | 26 | G | S | W | D | S | S | S | G | A | G | I | | | 27 |
| N6-VL_IMGT | 74 | G | S | W | D | S | S | S | G | A | G | I | F | G | 75 |
| N7-VL_Chothia | 80 | G | S | W | D | S | S | S | G | A | G | I | | | 81 |
| | CDR-L2 | | | | | | | | CDR-L3 | | | | | | |

| Residue | H55 | H56 | H57 | H58 | H59 | H60 | H61 | H62 | H63 | H64 | H65 | H66 | SEQ ID NO |
|---|---|---|---|---|---|---|---|---|---|---|---|---|---|
| N5-VH_Kabat | G | S | S | T | G | Y | G | P | A | V | E | G | 29 |
| N5-VH_IMGT | G | S | S | T | | | | | | | | | 77 |
| N5-VH_Chothia | G | S | S | | | | | | | | | | 83 |
| | | | | | | CDR-H2 | | | | | | | |

| Residue | H114 | H115 | H116 | H117 | H118 | SEQ ID NO |
|---|---|---|---|---|---|---|
| N5-VH_Kabat | G | G | I | D | A | 30 |
| N5-VH_IMGT | G | G | I | D | A | 78 |
| N5-VH_Chothia | G | G | I | D | A | 84 |
| | | | CDR-H3 | | | |

Anti-ELTD1 N7 AA sequence

| Residue | L21 | L22 | L23 | L24 | L25 | L26 | L27 | L28 | SEQ ID NO | L45 | L46 | L47 | L48 | L49 | L50 | L51 |
|---|---|---|---|---|---|---|---|---|---|---|---|---|---|---|---|---|
| N7-VL_Kabat | S | G | G | Y | S | G | Y | G | 31 | E | N | D | K | R | P | S |
| N7-VL_IMGT | | | | Y | S | G | | | 85 | E | N | D | | | | |
| N7-VL_Chothia | S | G | G | Y | S | G | Y | G | 91 | E | N | D | K | R | P | S |
| | | | | CDR-L1 | | | | | | | | | CDR-L2 | | | |

| Residue | H26 | H27 | H28 | H29 | H30 | H31 | H32 | H33 | H34 | H35 | SEQ ID NO | H50 | H51 | H52 | H53 | H54 |
|---|---|---|---|---|---|---|---|---|---|---|---|---|---|---|---|---|
| N7-VH_Kabat | G | F | D | F | S | S | Y | A | M | N | 88 | A | I | S | D | T |
| N7-VH_IMGT | G | F | D | F | S | S | Y | A | M | N | 88 | A | I | S | D | T |
| N7-VH_Chothia | G | F | D | F | S | S | Y | A | M | N | 94 | A | I | S | D | T |
| | | | | | | CDR-H1 | | | | | | | | CDR-H2 | | |

| Residue | H97 | H98 | H99 | H100 | H101 | H102 | H103 | H104 | H105 | H106 | H107 | H108 | H109 | H110 | H111 | H112 |
|---|---|---|---|---|---|---|---|---|---|---|---|---|---|---|---|---|
| N7-VH_Kabat | | | D | A | G | Y | A | A | G | W | G | A | A | G | S | I |
| N7-VH_IMGT | A | K | D | A | G | Y | A | A | G | W | G | A | A | G | S | I |
| N7-VH_Chothia | | | D | A | G | Y | A | A | G | W | G | A | A | G | S | I |
| | | | | | | | CDR-H3 | | | | | | | | | |

-continued

Anti-ELTD1 N7 AA sequence

| Residue | SEQ ID NO | L84 | L85 | L86 | L87 | L88 | L89 | L90 | L91 | L92 | L93 | L94 | L95 | L96 | SEQ ID NO |
|---|---|---|---|---|---|---|---|---|---|---|---|---|---|---|---|
| N7-VL_Kabat | 32 | G | S | A | D | R | S | N | N | V | G | I | | | 33 |
| N7-VL_IMGT | 86 | G | S | A | D | R | S | N | N | V | G | I | F | G | 87 |
| N7-VL_Chothia | 92 | G | S | A | D | R | S | N | N | V | G | I | | | 93 |

CDR-L3

| Residue | H55 | H56 | H57 | H58 | H59 | H60 | H61 | H62 | H63 | H64 | H65 | H66 | SEQ ID NO |
|---|---|---|---|---|---|---|---|---|---|---|---|---|---|
| N7-VH_Kabat | G | S | G | T | G | Y | G | A | A | V | K | G | 35 |
| N7-VH_IMGT | G | S | G | T | | | | | | | | | 89 |
| N7-VH_Chothia | G | S | G | | | | | | | | | | 95 |

CDR-H2

| Residue | H113 | H114 | SEQ ID NO |
|---|---|---|---|
| N7-VH_Kabat | D | A | 36 |
| N7-VH_IMGT | D | A | 90 |
| N7-VH_Chothia | D | A | 96 |

CDR-H3

Anti-ELTD1 N11 AA sequence

| Residue | L21 | L22 | L23 | L24 | L25 | L26 | L27 | L28 | SEQ ID NO | L45 | L46 | L47 | L48 | L49 | L50 | L51 |
|---|---|---|---|---|---|---|---|---|---|---|---|---|---|---|---|---|
| N11-VL_Kabat | S | G | G | S | G | S | Y | G | 37 | D | N | T | N | R | P | S |
| N11-VL_IMGT | S | G | G | S | G | S | Y | G | 97 | D | N | T | N | R | P | S |
| N11-VL_Chothia | S | G | G | S | G | S | Y | G | 103 | D | N | T | N | R | P | S |

CDR-L1  CDR-L2

| Residue | H26 | H27 | H28 | H29 | H30 | H31 | H32 | H33 | H34 | H35 | SEQ ID NO | H50 | H51 | H52 | H53 | H54 |
|---|---|---|---|---|---|---|---|---|---|---|---|---|---|---|---|---|
| N11-VH_Kabat | | | | | | S | F | Y | M | F | 40 | A | I | S | N | T |
| N11-VH_IMGT | G | F | T | F | S | S | F | Y | | | 100 | | I | S | N | T |
| N11-VH_Chothia | G | F | T | F | S | S | F | | | | 106 | | | S | N | T |

CDR-H1  CDR-H2

| Residue | H97 | H98 | H99 | H100 | H101 | H102 | H103 | H104 | H105 | H106 | H107 | H108 | H109 | H110 | H111 | H112 |
|---|---|---|---|---|---|---|---|---|---|---|---|---|---|---|---|---|
| N11-VH_Kabat | | | A | A | A | G | C | T | G | C | G | G | A | G | S | I |
| N11-VH_IMGT | A | K | A | A | A | G | C | T | G | C | G | G | A | G | S | I |
| N11-VH_Chothia | | | A | A | A | G | C | T | G | C | G | G | A | G | S | I |

CDR-H3

-continued

Anti-ELTD1 N11 AA sequence

| Residue | SEQ ID NO | L45 | L46 | L47 | L48 | L49 | L50 | L51 | L52 | L53 | L54 | SEQ ID NO |
|---|---|---|---|---|---|---|---|---|---|---|---|---|
| N11-VL_Kabat | 38 | G | S | E | D | I | S | Y | I | G | I | 39 |
| N11-VL_IMGT | 98 | G | S | E | D | I | S | Y | I | G | I | 39 |
| N11-VL_Chothia | 104 | G | S | E | D | I | S | Y | I | G | I | 39 |

Chothia

| Residue | H55 | H56 | H57 | H58 | H59 | H60 | H61 | H62 | H63 | H64 | H65 | H66 | SEQ ID NO |
|---|---|---|---|---|---|---|---|---|---|---|---|---|---|
| N11-VH_Kabat | G | S | G | T | D | Y | G | A | A | V | Q | G | 41 |
| N11-VH_IMGT | G | S | G | T | | | | | | | | | 101 |
| N11-VH_Chothia | G | S | G | | | | | | | | | | 107 |

CDR-H2

| Residue | H113 | H114 | SEQ ID NO |
|---|---|---|---|
| N11-VH_Kabat | D | A | 42 |
| N11-VH_IMGT | D | A | 102 |
| N11-VH_Chothia | D | A | 108 |

CDR-H3

Anti-ELTD1 N15 AA sequence

| Residue | L21 | L22 | L23 | L24 | L25 | L26 | L27 | L28 | SEQ ID NO | L45 | L46 | L47 | L48 | L49 | L50 | L51 |
|---|---|---|---|---|---|---|---|---|---|---|---|---|---|---|---|---|
| N15-VL_Kabat | S | G | G | S | Y | S | Y | G | 43 | D | N | T | N | R | P | S |
| N15-VL_IMGT | | | | S | Y | S | | | 109 | D | N | T | | | | |
| N15-VL_Chothia | S | G | G | S | Y | S | Y | G | 115 | D | N | T | N | R | P | S |

CDR-L1 | | | | | | | | | CDR-L2

| Residue | H26 | H27 | H28 | H29 | H30 | H31 | H32 | H33 | H34 | H35 | SEQ ID NO | H50 | H51 | H52 | H53 | H54 |
|---|---|---|---|---|---|---|---|---|---|---|---|---|---|---|---|---|
| N15-VH_Kabat | | | | | | S | V | N | M | F | 46 | A | I | G | N | D |
| N15-VH_IMGT | G | F | T | F | S | S | V | N | | | 112 | | I | G | N | D |
| N15-VH_Chothia | G | F | T | F | S | S | V | | | | 118 | | | G | N | D |

CDR-H1 | | | | | | | | | | CDR-H2

| Residue | H97 | H98 | H99 | H100 | H101 | H102 | H103 | H104 | H105 | H106 | H107 | H108 | H109 | 110 | H111 | H112 |
|---|---|---|---|---|---|---|---|---|---|---|---|---|---|---|---|---|
| N15-VH_Kabat | | | A | S | A | C | S | T | S | G | C | G | G | A | G | S |
| N15-VH_IMGT | A | K | A | S | A | C | S | T | S | G | C | G | G | A | G | S |
| N15-VH_Chothia | | | A | S | A | C | S | T | S | G | C | G | G | A | G | S |

CDR-H3

-continued

Anti-ELTD1 N15 AA sequence

| Residue | SEQ ID NO | L84 | L85 | L86 | L87 | L88 | L89 | L90 | L91 | L92 | L93 | SEQ ID NO |
|---|---|---|---|---|---|---|---|---|---|---|---|---|
| N15-VL_Kabat | 44 | G | S | A | D | S | S | Y | I | G | I | 45 |
| N15-VL_IMGT | 110 | G | S | A | D | S | S | Y | I | G | I | 111 |
| N15-VL_Chothia | 116 | G | S | A | D | S | S | Y | I | G | I | 117 |
| | | | | | | | CDR-L3 | | | | | |

| Residue | H55 | H56 | H57 | H58 | H59 | H60 | H61 | H62 | H63 | H64 | H65 | H66 | SEQ ID NO |
|---|---|---|---|---|---|---|---|---|---|---|---|---|---|
| N15-VH_Kabat | A | G | G | T | D | Y | G | A | A | V | D | G | 47 |
| N15-VH_IMGT | A | G | G | T | | | | | | | | | 113 |
| N15-VH_Chothia | A | G | G | | | | | | | | | | 119 |
| | | | | | | | CDR-H2 | | | | | | |

| Residue | H113 | H114 | H115 | SEQ ID NO |
|---|---|---|---|---|
| N15-VH_Kabat | I | D | A | 48 |
| N15-VH_IMGT | I | D | A | 114 |
| N15-VH_Chothia | I | D | A | 120 |
| | | CDR-H3 | | |

Anti-ELTD1 N16 AA sequence

| Residue | L21 | L22 | L23 | L24 | L25 | L26 | L27 | L28 | SEQ ID NO | L45 | L46 | L47 | L48 | L49 | L50 | L51 |
|---|---|---|---|---|---|---|---|---|---|---|---|---|---|---|---|---|
| N16-VL_Kabat | S | G | G | G | G | S | Y | G | 49 | D | N | N | K | R | P | S |
| N16-VL_IMGT | | | | G | G | S | | | 121 | D | N | N | | | | |
| N16-VL_Chothia | S | G | G | G | G | S | Y | G | 127 | D | N | N | K | R | P | S |
| | | | CDR-L1 | | | | | | | | | CDR-L2 | | | | |

| Residue | H26 | H27 | H28 | H29 | H30 | H31 | H32 | H33 | H34 | H35 | SEQ ID NO | H50 | H51 | H52 | H53 | H54 |
|---|---|---|---|---|---|---|---|---|---|---|---|---|---|---|---|---|
| N16-VH_Kabat | | | | | | S | V | N | M | F | 52 | A | I | G | N | D |
| N16-VH_IMGT | G | F | T | F | S | S | V | N | | | 124 | | I | G | N | D |
| N16-VH_Chothia | G | F | T | F | S | S | V | | | | 130 | | | G | N | D |
| | | | | CDR-H1 | | | | | | | | | | CDR-H2 | | |

| Residue | H97 | H98 | H99 | H100 | H101 | H102 | H103 | H104 | H105 | H106 | H107 | H108 | H109 | H110 | H111 | H112 |
|---|---|---|---|---|---|---|---|---|---|---|---|---|---|---|---|---|
| N16-VH_Kabat | | | A | S | A | C | S | T | S | G | C | G | G | A | G | S |
| N16-VH_IMGT | A | K | A | S | A | C | S | T | S | G | C | G | G | A | G | S |
| N16-VH_Chothia | | | A | S | A | C | S | T | S | G | C | G | G | A | G | S |
| | | | | | | CDR-H3 | | | | | | | | | | |

-continued

Anti-ELTD1 N16 AA sequence

| Residue | SEQ ID NO | L84 | L85 | L86 | L87 | L88 | L89 | L90 | L91 | L92 | L93 | SEQ ID NO |
|---|---|---|---|---|---|---|---|---|---|---|---|---|
| N16-VL_Kabat | 50 | G | S | A | D | N | T | Y | V | G | I | 51 |
| N16-VL_IMGT | 122 | G | S | A | D | N | T | Y | V | G | I | 123 |
| N16-VL_Chothia | 128 | G | S | A | D | N | T | Y | V | G | I | 129 |

CDR-L3

| Residue | H55 | H56 | H57 | H58 | H59 | H60 | H61 | H62 | H63 | H64 | H65 | H66 | SEQ ID NO |
|---|---|---|---|---|---|---|---|---|---|---|---|---|---|
| N16-VH_Kabat | A | G | G | T | D | Y | G | A | A | V | D | G | 53 |
| N16-VH_IMGT | A | G | G | T | | | | | | | | | 125 |
| N16-VH_Chothia | A | G | G | | | | | | | | | | 131 |

CDR-H2

| Residue | H113 | H114 | H115 | SEQ ID NO |
|---|---|---|---|---|
| N16-VH_Kabat | I | D | A | 54 |
| N16-VH_IMGT | I | D | A | 126 |
| N16-VH_Chothia | I | D | A | 132 |

CDR-H3

Anti-ELTD1 N17 AA sequence

| Residue | L21 | L22 | L23 | L24 | L25 | L26 | L27 | L28 | L29 | SEQ ID NO | L46 | L47 | L48 | L49 | L50 | L51 |
|---|---|---|---|---|---|---|---|---|---|---|---|---|---|---|---|---|
| N17-VL_Kabat | S | G | G | G | S | Y | G | Y | G | 55 | W | D | N | K | R | P |
| N17-VL_IMGT | | | | G | S | Y | G | | | 61 | W | D | N | | | |
| N17-VL_Chothia | S | G | G | G | S | Y | G | Y | G | 67 | W | D | N | K | R | P |

CDR-L1 | CDR-L2

| Residue | H26 | H27 | H28 | H29 | H30 | H31 | H32 | H33 | H34 | H35 | SEQ ID NO | H50 | H51 | H52 | H53 | H54 |
|---|---|---|---|---|---|---|---|---|---|---|---|---|---|---|---|---|
| N17-VH_Kabat | | | | | | S | Y | A | M | N | 58 | S | I | D | D | G |
| N17-VH_IMGT | G | F | D | F | S | S | Y | A | | | 64 | | I | D | D | G |
| N17-VH_Chothia | G | F | D | F | S | S | Y | | | | 70 | | | D | D | G |

CDR-H1 | CDR-H2

| Residue | H97 | H98 | H99 | H100 | H101 | H102 | H103 | H104 | H105 | H106 | H107 | H108 | H109 | H110 | H111 | H112 |
|---|---|---|---|---|---|---|---|---|---|---|---|---|---|---|---|---|
| N17-VH_Kabat | | | D | A | S | S | G | G | V | W | S | A | A | A | G | I |
| N17-VH_IMGT | A | K | D | A | S | S | G | G | V | W | S | A | A | A | G | I |
| N17-VH_Chothia | | | D | A | S | S | G | G | V | W | S | A | A | A | G | I |

CDR-H3

Anti-ELTD1 N17 AA sequence

| Residue | L52 | SEQ ID NO | L85 | L86 | L87 | L88 | L89 | L90 | L91 | L92 | L93 | L94 | L95 | SEQ ID NO |
|---|---|---|---|---|---|---|---|---|---|---|---|---|---|---|
| N17-VL_Kabat | S | 56 | G | S | A | D | S | S | G | T | A | A | I | 57 |
| N17-VL_IMGT |  | 62 | G | S | A | D | S | S | G | T | A | A | I | 63 |
| N17-VL_Chothia | S | 68 | G | S | A | D | S | S | G | T | A | A | I | 69 |
| CDR-L2 | | | CDR-L3 | | | | | | | | | | | |

| Residue | H55 | H56 | H57 | H58 | H59 | H60 | H61 | H62 | H63 | H64 | H65 | H66 | SEQ ID NO |
|---|---|---|---|---|---|---|---|---|---|---|---|---|---|
| N17-VH_Kabat | G | S | D | T | T | Y | G | A | A | V | K | G | 59 |
| N17-VH_IMGT | G | S | D | T | | | | | | | | | 56 |
| N17-VH_Chothia | G | S | D | | | | | | | | | | 71 |
| | | | | | | CDR-H2 | | | | | | | |

| Residue | H113 | H114 | SEQ ID NO |
|---|---|---|---|
| N17-VH_Kabat | D | A | 60 |
| N17-VH_IMGT | D | A | 66 |
| N17-VH_Chothia | D | A | 72 |
| | | CDR-H3 | |

Example 2. Optimized Monoclonal Antibody Treatment Against ELTD1 for Glioblastoma (GBM) in a G55 Xenograft Mouse Model Glioblastoma is an aggressive brain tumor found in adults and the therapeutic approaches available have not significantly increased patient survival. Recently, the inventors discovered that ELTD1, an angiogenic biomarker, is highly expressed in human gliomas. Polyclonal anti-ELTD1 treatments were effective in glioma preclinical models, however, pAb binding is potentially promiscuous, is difficult to manufacture, and is not a favorable molecule when considering drug development and approval. Therefore, the aim of this example was to determine the effects of an optimized monoclonal anti-ELTD1 treatment in G55 xenograft glioma models. Magnetic resonance imaging (MRI) was used to assess the effects of the treatments on animal survival, tumor volumes, perfusion rates, and binding specificity. Immunohistochemistry and histology were conducted to confirm and characterize microvessel density and Notch1 levels, and to locate the molecular probes. RNA-sequencing was used to analyze the effects of the mAb treatment. The monoclonal anti-ELTD1 treatment significantly increased animal survival, reduced tumor volumes, normalized the vasculature, and showed higher binding specificity within the tumor compared to both control and polyclonal treated mice. Notch1 positivity staining and RNA-seq results suggested that ELTD1 has the ability to interact with and interrupt Notch1 signaling. Although little is known about ELTD1, particularly about its ligand and pathways, these data show that the monoclonal anti-ELTD1 antibodies can be used for anti-angiogenic therapy in glioblastomas.

Of all malignant gliomas diagnosed in adults, 82% are characterized as glioblastoma (GBM), which has an incidence of 3.19 per 100,000 persons in the United States [1,2].

This high-grade glioma undergoes unregulated vascular angiogenesis and is characterized as being invasive, highly vascular, and resistant to apoptosis [3]. The current treatment plan is surgical resection followed by a combination of radiation and chemotherapy with temozolomide or the anti-angiogenic mAb bevacizumab [4,5]. However, even with treatments, the median survival for patients is only 12-14 months post-detection, and less than 5% of patients survive past 5 years post-diagnosis [2,6]. GBMs undergo gene amplification and/or mutation of the epidermal growth factor (EGF) receptor and higher EGFR levels were shown to promote migration, tumor growth, and angiogenesis [7]. Gliomas rely heavily on angiogenesis for tumor growth and the new vessels are key for delivering oxygen and nutrients to the tumor site. Throughout the years, the primary focus among the pro-angiogenic factors was the vascular endothelial growth factor (VEGF) for its role of increasing vascularization in cancer. While the tumor develops, there is an upregulation of pro-angiogenic cytokines in the region that further increase VEGF-A, along with other microvasculature proliferation factors such as basic fibroblast growth factor (bFGF) and epidermal growth factor (EGF) [8]. Once upregulated, VEGF-A binds onto VEGF receptor 2 (VEGFR2) on endothelial cells to initiate a cascade of signaling pathways that promote the formation of new blood vessels [9]. Bevacizumab is a monoclonal therapy against VEGF-A approved as a GBM therapeutic agent along with multiple other cancers. However, this chemotherapeutic agent has not significantly increased the survival of patients suffering with GBM. Furthermore, bevacizumab has serious adverse side effect such as severe/fatal hemorrhaging that occurs up to 5-fold more frequently [10]. Due to bevacizumab's failure to increase patient's survival, it was crucial to shift the focus from VEGF to other angiogenic factors present in GBMs. In certain aspects, the present invention can be used to treat one or more cancers selected from a glioma, breast cancer, hepatocellular carcinoma, lung cancer, ovarian cancer; ovarian cancer; metastatic colorectal cancer; cervical cancer; renal cell carcinoma; glioblastoma; or a non-squamous non-small cell lung cancer.

The epidermal growth factor, latrophilin, and seven transmembrane domain-containing protein on chromosome 1 (ELTD1), alternatively known as the adhesion G protein-coupled receptor L4 (ADGRL4) was first discovered in developing cardiomyocytes [11]. ELTD1, a novel regulator of brain angiogenesis, was found to promote tumor growth and metastasis [12]. The present inventors previously reported that ELTD1 was highly expressed in high-grade gliomas and was expressed on both endothelial and tumor cells [11]. Furthermore, ELTD1 expression was shown to be regulated by the two main angiogenic pathways, where VEGF increased ELTD1 expression, and DLL4-Notch signaling decreased ELTD1 expression in normal vasculature [12]. Further investigation into ELTD1 demonstrated that increased signaling from VEGF-A resulted in an increase of ELTD1 expression in endothelial cells, and that targeting ELTD1 had decreased VEGFR2 expression in a glioma model [13,14].

There are approximately 17,000 new GBM diagnoses every year, increasing the need for new and more effective cancer therapeutics [1]. It was previously found that polyclonal antibody (pAb) treatments against ELTD1 in orthotropic GL261 and human G55 xenograft glioma preclinical models were successful in decreasing tumor volumes (TV), increasing survival, and decreasing microvessel density levels (MVD) when compared to untreated (UT) control [15]. However, batch-to-batch variabilities, as well as lack of selectivity of pAbs posed concerns about specificity as long-term treatment for patients. Monoclonal antibodies (mAb) are produced from a single B cell clone that allows for homogeneous antibodies and are established as a successful class of targeted treatments for various cancers and chronic inflammatory diseases [16]. Emerging mAb treatments bind onto growth factors overexpressed on the tumor to disrupt downstream signaling effects to decrease tumor cell growth, proliferation, and migration [17].

Previous research has demonstrated that pAb treatment against ELTD1 was an effective treatment in GBM pre-clinical models. This example used an optimized monoclonal antibody (mAb) against ELTD1 that has a higher specificity by only binding to the external region of the receptor (430 AA) overcoming the limitations set by the pAb treatments in hopes of obtaining a more specific and profound effect on a G55 glioma pre-clinical model.

The preparation of recombinant extracellular domain of ELTD1 human Ckappa fusion protein, generation of monoclonal antibodies, and immunoassays are as described hereinabove.

G55 Xenograft model and treatment. All animal studies were conducted with the approval (protocol 17-48) of the Oklahoma Medical Research Foundation Institutional Animal Care Use Committee policies, which follow NIH guidelines. Human G55 xenograft cells were implanted intracerebrally in two-month old male mice (Hsd:Athymic Nude-Foxn1nu mice; Harlan Inc., Indianapolis, IN), as previously described [13,15]. The animals were divided into three groups: UT, pAb and mAb anti-ELTD1 treated. Once tumors reached 6-7 mm3 (determined via MRI), mice were either left UT or were treated with 2 mg/kg of either polyclonal anti-ELTD1 (Bioss, ETL/ELTD1 Polyclonal Antibody, bs-13111R) or an optimized mAb against ELTD1 every 3-4 days (treated M/Th, T/F, W/Sat). All mice were euthanized when tumors reached >150 mm3.

In vivo magnetic resonance (MR) techniques. Morphological imaging. Mice were anesthetized and positioned in a cradle. A 30-cm horizontal bore Bruker Biospin magnet operating at 7 Tesla (Bruker BioSpin GmbH, Karlsruhe, Germany) was used. A BA6 gradient set and mouse head coil were used to perform all MRI experiments as previously described [15]. All animals were imaged every 2-3 days until the end of the study starting at 10 days post-G55 implantation surgery.

Perfusion imaging. The perfusion imaging method, arterial spin labeling, was used as previously described [23]. Perfusion maps were obtained on a single axial slice of the brain located on the point of the rostro-caudal axis where the tumor had the largest cross section. Five regions of interest (ROIs) were manually outlined around the tumor, and appropriate ROIs were also taken from the contralateral side of the brain for comparison purposes. To calculate the differences in (rCBF) values, tumor rCBF values were obtained at late (prior to termination) and early (at tumor detection) tumor stages and normalized to rCBF values in the contralateral brain region of corresponding animals.

Molecular-targeted MR imaging (mt-MRI). The contrast agent, biotin-BSA (bovine serum albumin)-Gd (gadolinium)-DTPA, was prepared as previously described by the present inventors [15], based on the modification of the method developed by Dafni et al [24,25]. pAb anti-ELTD1 (Bioss) or mAb anti-ELTD, were conjugated to the albumin moiety through a sulfo-NHS-EDC link according to the protocol of Hermanson [26]. mt-MRI was performed when tumor volumes were around 130-180 mm3. Molecular probes with a biotin-albumin-Gd-DTPA construct bound to anti-ELTD1 antibodies were injected via a tail vein catheter in mice. A non-specific mouse immunoglobulin IgG Ab (Alpha Diagnostics) was used with the biotin-albumin-Gd-DTPA construct as a negative control. MRI was done as previously described [13,24]. Relative probe concentrations were calculated to assess the levels of ELTD1 and the non-specific IgG contrast agent in each animal. Contrast difference images were created from the pre- and (90 minutes) post-contrast datasets for the slice of interest, by computing the difference in T1 relaxation times between the post-contrast and the pre-contrast image on a pixel basis. From difference images, ten ROIs of equal size (0.05 cm$^2$), were drawn within areas with the highest T1 relaxation at the TR 800 ms, in the tumor parenchyma and contralateral side of the brains of each animal, after anti-ETLD1 probe injections. T1 values obtained from the ROIs in the tumor regions were normalized to the corresponding contralateral sides. The T1 relaxation values of the specified ROIs were computed from all pixels in the ROIs, by the following equation taken (processed by ParaVision 5.0, Bruker): $S(TR)=S0(1-e-TR/T1)$, where TR is the repetition time, S0 is the signal intensity (integer machine units) at TR, T1 and TE=0, and T1 is the constant of the longitudinal relaxation time [27]. Overlays of contrast difference images and T1-weighted images were generated using Photoshop software (version C.S 6).

Immunohistochemistry and Standard Staining. All mice were euthanized after the last MRI examination. The brain of each animal was removed, preserved in 10% neutral buffered formalin, and processed routinely. Hematoxylin-eosin staining: tissues were fixed in 10% neutral buffered formalin, dehydrated, and embedded in paraffin. Sections were deparaffinized, rehydrated, and stained according to standard protocols. Several reagents were produced by Vector Labs Inc. (VLI) in Burlingame, CA.

Histological sections (5 μm) embedded in paraffin and mounted on HistoBond® Plus slides (Statlab Medical Products, Lewisville, TX) were rehydrated and washed in Phosphate Buffered Saline (PBS). The sections were processed using the ImmPRESS™ VR Reagent Anti-Rabbit IgG Peroxidase (VLI cat #MP-6401). Antigen retrieval (pH6 citrate antigen unmasking solution; (VLI cat #H-3300) was accomplished via 20-minutes in a steamer followed by 30-minutes cooling at room temperature. Sections were treated with a peroxidase blocking reagent (Bloxall, VLI cat #SP-6000), followed by 2.5% normal horse serum to inhibit nonspecific binding. Rabbit Anti-CD34 antibody (abcam81289; 5.28 μg/ml; Cambridge, MA) or Rabbit Anti-NOTCH 1 (abcam52627; 11 μg/ml; Cambridge, MA) was applied to each section and following incubation overnight (4° C.) in a humidified chamber, sections were washed in PBS, the ImmPRESS VR reagent was applied according to the manufacturer's directions.

To characterize microvessel density (MVD) and Notch expression levels, five ROIs, captured digitally (20×), were identified in each case. Only areas containing tumor tissue were analyzed, excluding areas with necrosis and/or significant artifacts. The number of positive pixels was divided by the total number of pixels (negative and positive) in the analyzed area. ROIs were analyzed and imaged using Aperio ImageScope (Leica Biosystems, Buffalo Grove, IL).

Sections for streptavidin horse radish peroxidase (SA-HRP) were processed as above, except they were incubated overnight with ready to use (RTU) Strp-HRP (VLI cat #SA-5704). Appropriate washes were in PBS. Slides were incubated with NovaRed® (VLI cat #SK-4805) chromogen for visualization. Counterstaining was carried out with Hematoxylin QS Nuclear Counterstain (VLI). Appropriate positive and negative tissue controls were used.

RNA isolation and preparation. Mice were euthanized after the last MRI examination. Brains were removed, snap frozen, and stored at −80° C. Total RNA from tumor tissues from all groups was purified with a RNeasy Mini Kit (Qiagen) and quantified by spectrophotometry (Nanodrop).

Concentration of RNA was ascertained, and overall quality of RNA was verified. Sequencing libraries were generated (Lexogen Quantseq FWD library prep kit) according to the manufacturer's protocol. Briefly, the first strand of cDNA was generated using 5'-tagged poly-T oligomer primers, and following RNase digestion, the second strand was generated using 5'-tagged random primers. A subsequent PCR step with additional primers added the complete adapter sequence to the initial 5' tags, added unique indices for demultiplexing of samples, and amplified the library. Final libraries for each sample were assayed (Agilent Tapestation) for appropriate size and quantity. These libraries were pooled in equimolar amounts (fluorometric analyses). Final pools were absolutely quantified using qPCR (Roche LightCycler 480 instrument with Kapa Biosystems Illumina Library Quantification reagents). Sequencing was performed (Illumina Nextseq 500 instrument) with High Output chemistry and 75-bp single-ended reads.

Bioinformatics Analysis. Paired-end fastq files were checked for quality using multiQC [28], for which the following mean (standard deviation) descriptive values were 54 million reads (12), 68.8% (2.8%) duplicate reads, and a GC content of 51.3% (0.7%). The indexing and alignment were run with kallisto[29] against build 38 of the human reference genome from the Genome Reference Consortium (GRCh38). Assignment of counts to exon features and normalization were performed along with the alignment via the biojupies pipeline4 to provide a counts matrix. Significant differential genes were determined by DESeq2[30] for genes having both a Benjamini-Hochberg adjusted p-value <0.05 and an absolute log fold-change of >1.3. Gene set enrichment analysis was performed on the identified differential genes via ennchR[31] (gseapy API).

Statistical Analysis. Survival curves were analyzed using Kaplan-Meier curves. Tumor volumes, perfusion changes, and immunohistochemistry protein levels, and molecular-targeted MRI data were analyzed and compared by one- or two-way ANOVA with multiple comparisons (Tukey's or Sidak's respectively). Data were represented as mean±SD, and p-values of either *<0.05, <0.01, *<0.001, ****<0.0001 were considered statistically significant.

Figure 1B:
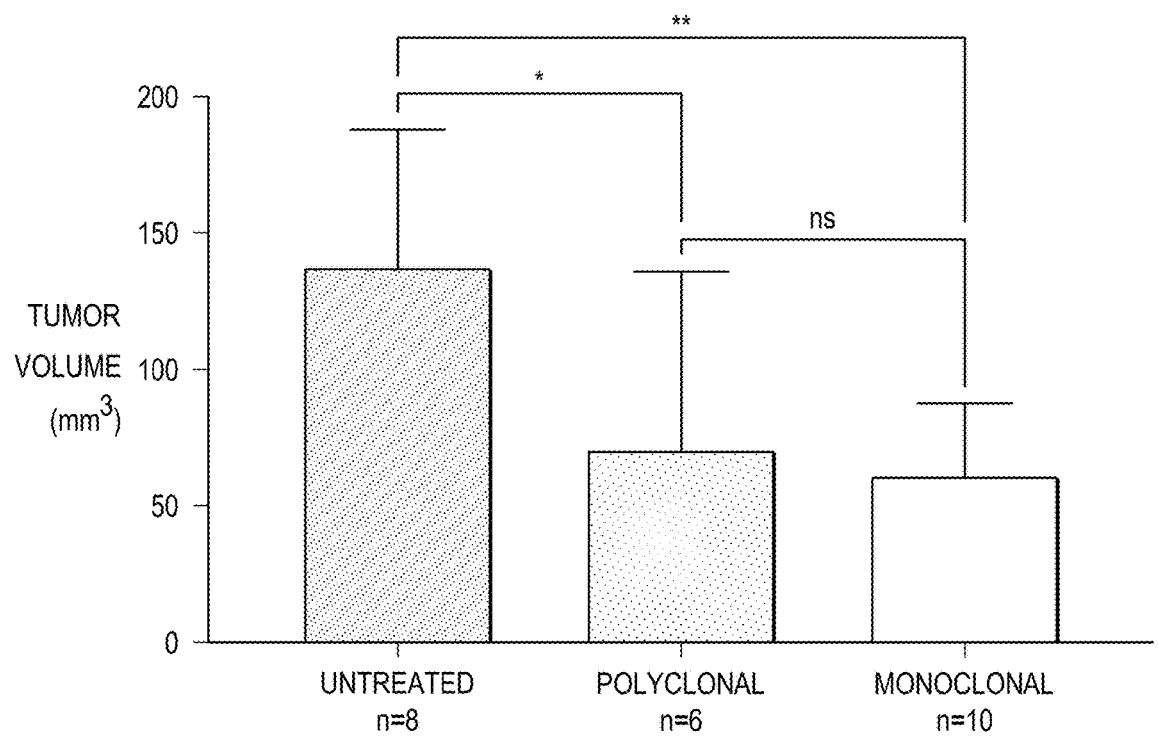
Figure 1C:
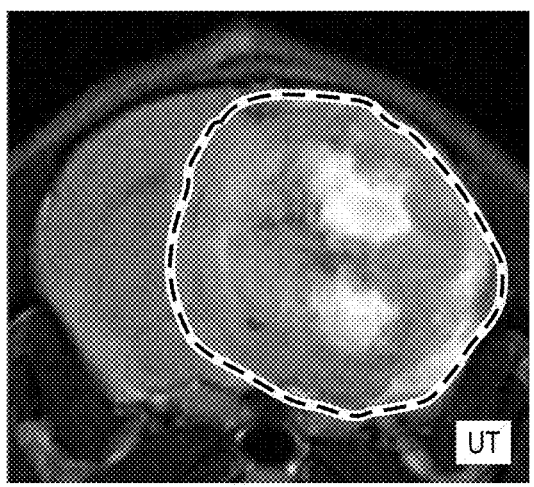
Figure 1D:
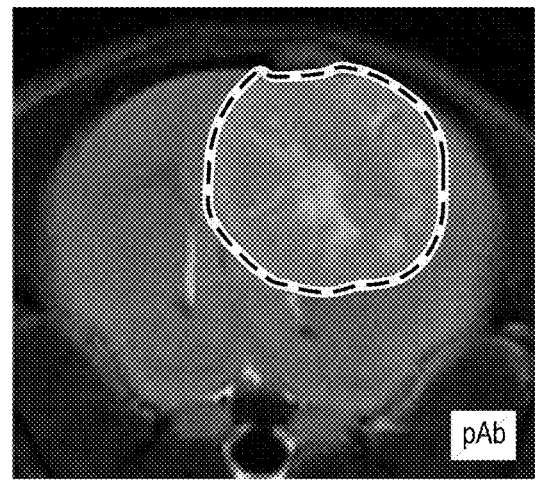
Figure 1E:
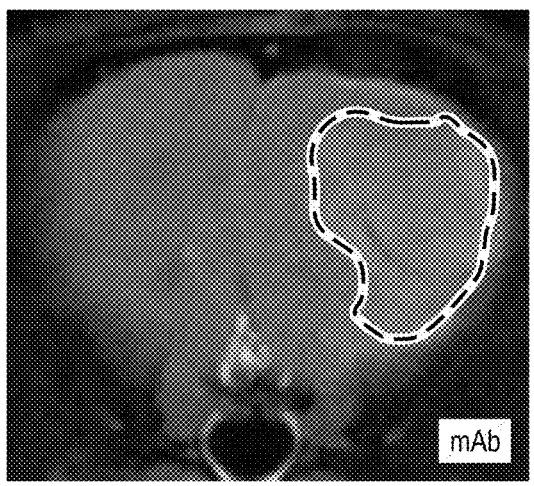

Prior studies demonstrated that non-specific IgG antibody treatments as a control group did not differ from untreated, therefore in this example the inventors only utilized untreated animals as the control group [15]. G55 glioma-bearing mice were treated with Abs against ELTD1. Both anti-ELTD1 pAb (p=0.0207) and anti-ELTD1 mAb (p=0.0024), significantly increased survival compared to untreated mice (average survival of untreated animals was ~9 days post tumor detection) as shown in FIG. 1A. Morphological imaging and analysis demonstrated that tumor volumes at 9 days post-tumor detection (as evidenced by MRI), were significantly lower with the mAb (p=0.0067) and pAb (p=0.0384) anti-ELTD1 treatment compared to controls (FIG. 1B). Representative images of tumor bearing mice from all treatment groups are shown in FIG. 1C.

Figure 2A:
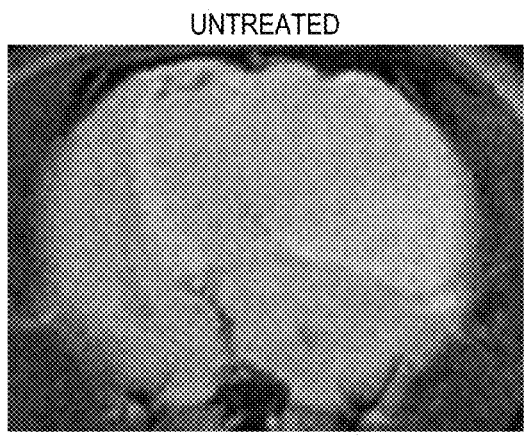
FIGS. 2A to 2G show monoclonal anti-ELTD1 treatment of mice with GBM normalizes vasculature within the tumor. Representative morphological images with respective MR perfusion maps for each treatment group: UT controls (FIG. 2A-B), anti-ELTD1 pAb-treated animals (FIG. 2C-D), and anti-ELTD1 mAb-treated animals (FIG. 2E-F).
Figure 2B:
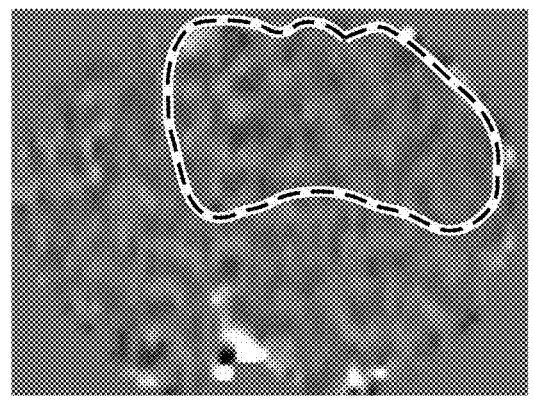
Figure 2C:
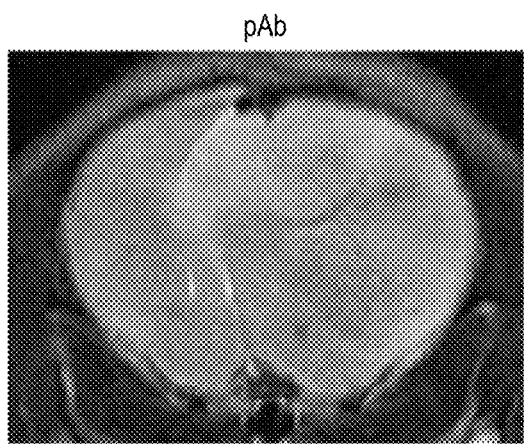
Figure 2D:
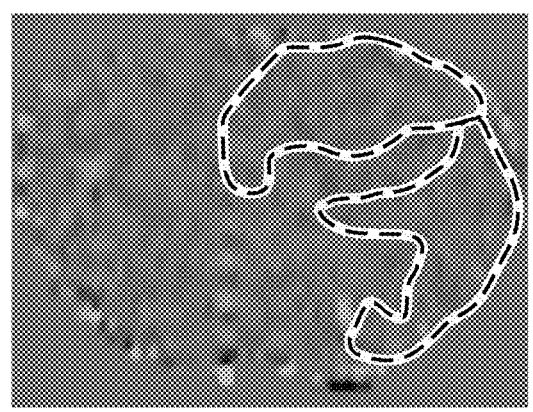
Figure 2E:
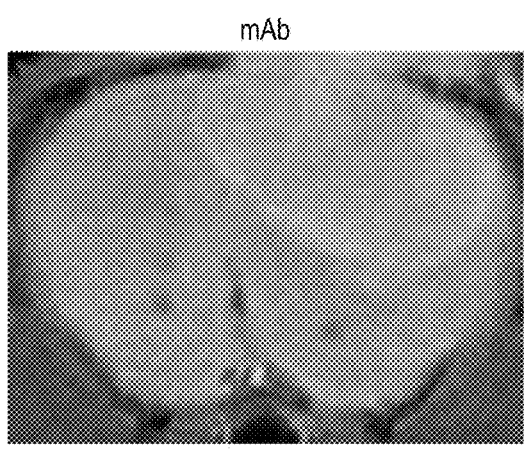
Figure 2F:
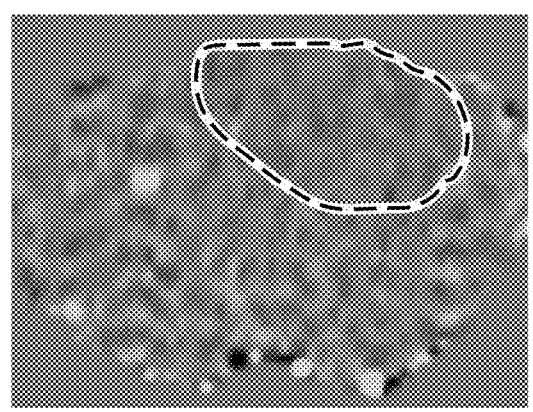
Figure 2G:
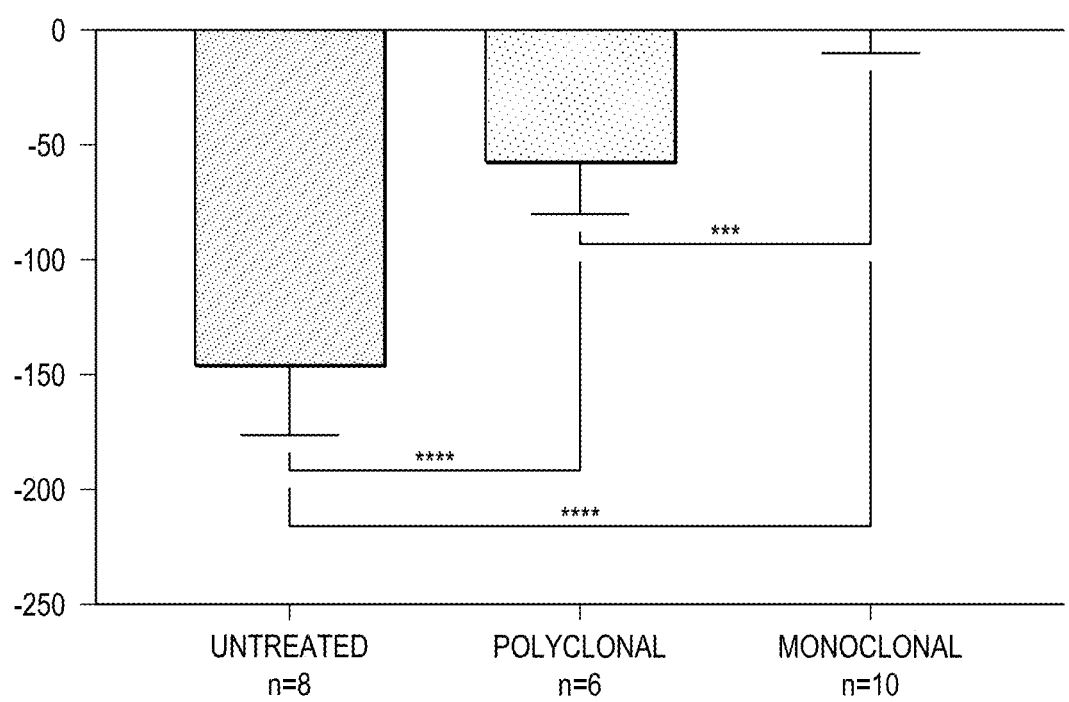

MRI perfusion measures the relative cerebral blood flow (rCBF) and can be used to assess the microvasculature alterations associated with tumor angiogenesis. Healthy normal tissue has a set rCBF, however as the tumor grows, it disrupts the vasculature, and therefore decreases the perfusion rate. Differences in rCBF demonstrated that the untreated mice had a decrease in rCBF in the tumor regions depicting increased angiogenesis while the anti-ELTD1 treated animals had a normalization of perfusion values. Representative morphological MRIs along with the corresponding perfusion maps of the brain are depicted in FIG. 2A-F. The decrease in perfusion (depicted as decreased normalized rCBF) as a result of the tumor, outlined by the yellow dashed line in 2B, 2D, 2F, is demonstrated by the dark areas. The anti-ELTD1 mAb and anti-ELTD1 pAb treatments were successful in decreasing angiogenesis and therefore increasing perfusion within the tumor region. The anti-ELTD1 pAb treatment was able to minimize the decrease in rCBF (p<0.0001) compared to UT mice. The anti-ELTD1 mAb treatment was significantly more effective in decreasing the rCBF compared to both pAb treatment (p=0.0001) and UT animals (p<0.0001) (FIG. 2G) and normalized the rCBF within the tumor region to contralateral levels.

Figure 3A:
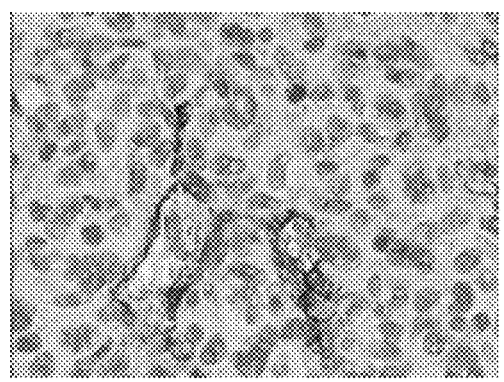
FIGS. 3A to 3D show that anti-ELTD1 antibody therapy is effective in decreasing the microvessel density (MVD) in mice with GBM. Representative IHC images (20×) for CD34 from untreated (FIG. 3A), anti-ELTD1 pAb-treated (FIG. 3B), and anti-ELTD1 mAb-treated (FIG. 3C) animals. Dark red/brown staining in the slides represent vessels in the tumor region highlighted by the arrows.
Figure 3B:
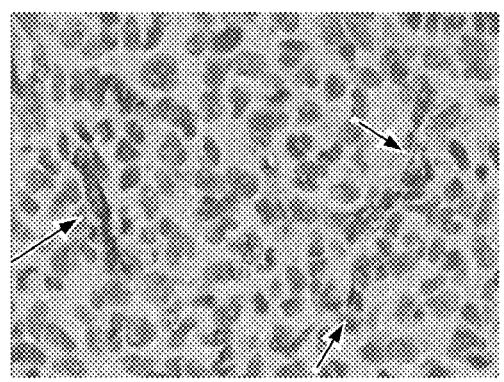
Figure 3C:
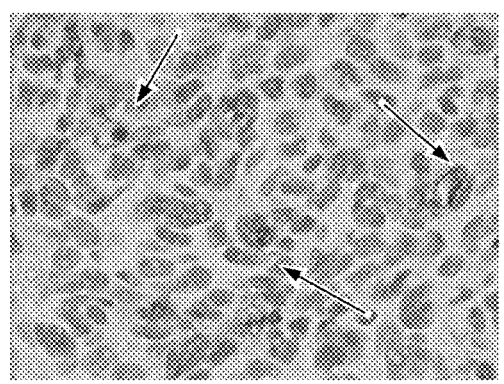
Figure 3D:
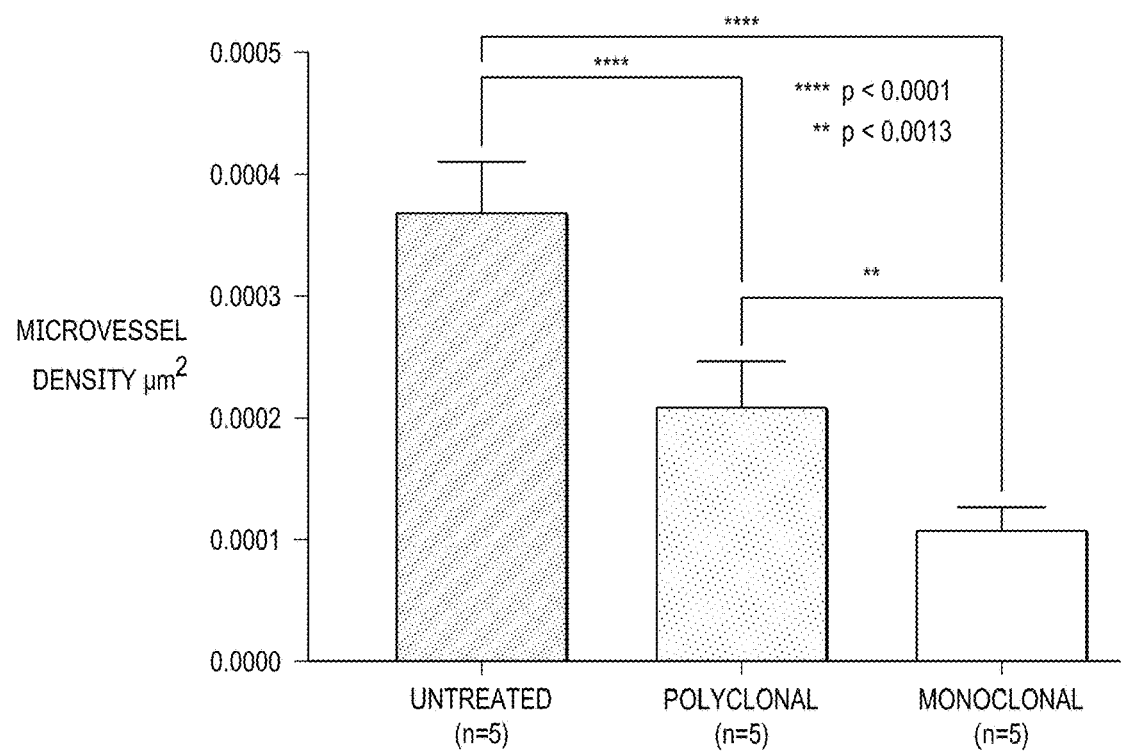

ELTD1 has been linked with pathological angiogenesis. Therefore, the inventors analyzed microvessel density (MVD) to determine whether the anti-ELTD1 Ab treatments would alter the tumor vasculature. Representative CD34 IHC images for each treatment groups are shown in FIG. 3A-C. CD34 analysis demonstrated that the anti-ELTD1 treatments significantly decreased the MVD levels (p<0.0001) compared to untreated animals (FIG. 3D). The anti-ELTD1 mAb treatment further decreased the MVD levels compared to the polyclonal anti-ELTD1 treatment (p=0.0013) and was able to return the MVD to near normal levels.

Figure 4A:
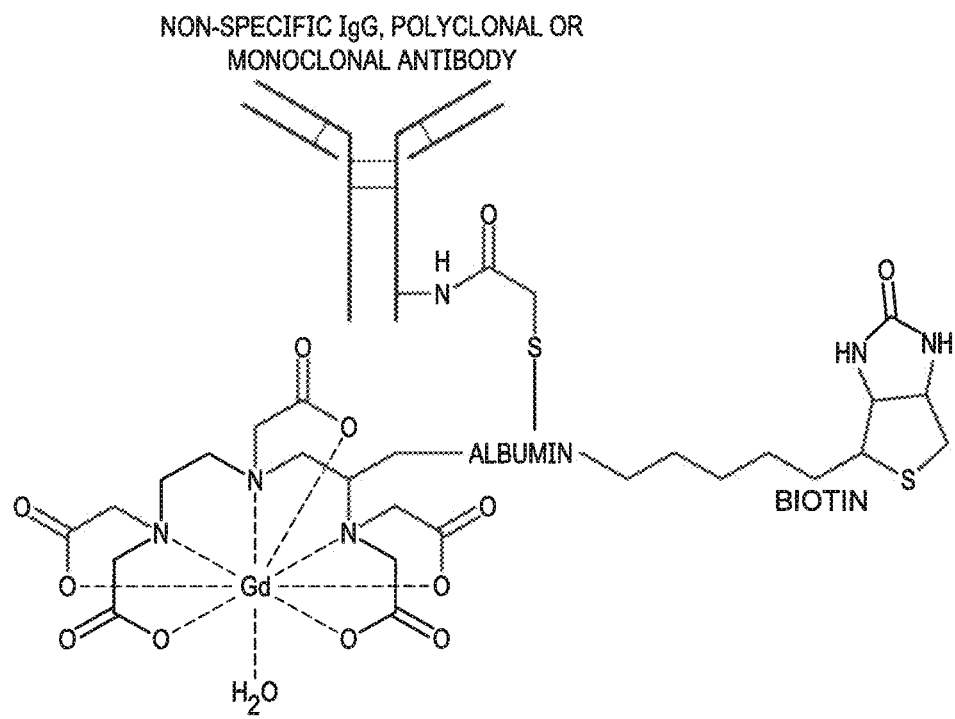
FIGS. 4A to 4H show an anti-ELTD1 mAb probe has significantly higher binding specificity against the GBM tumor.
Figure 4B:
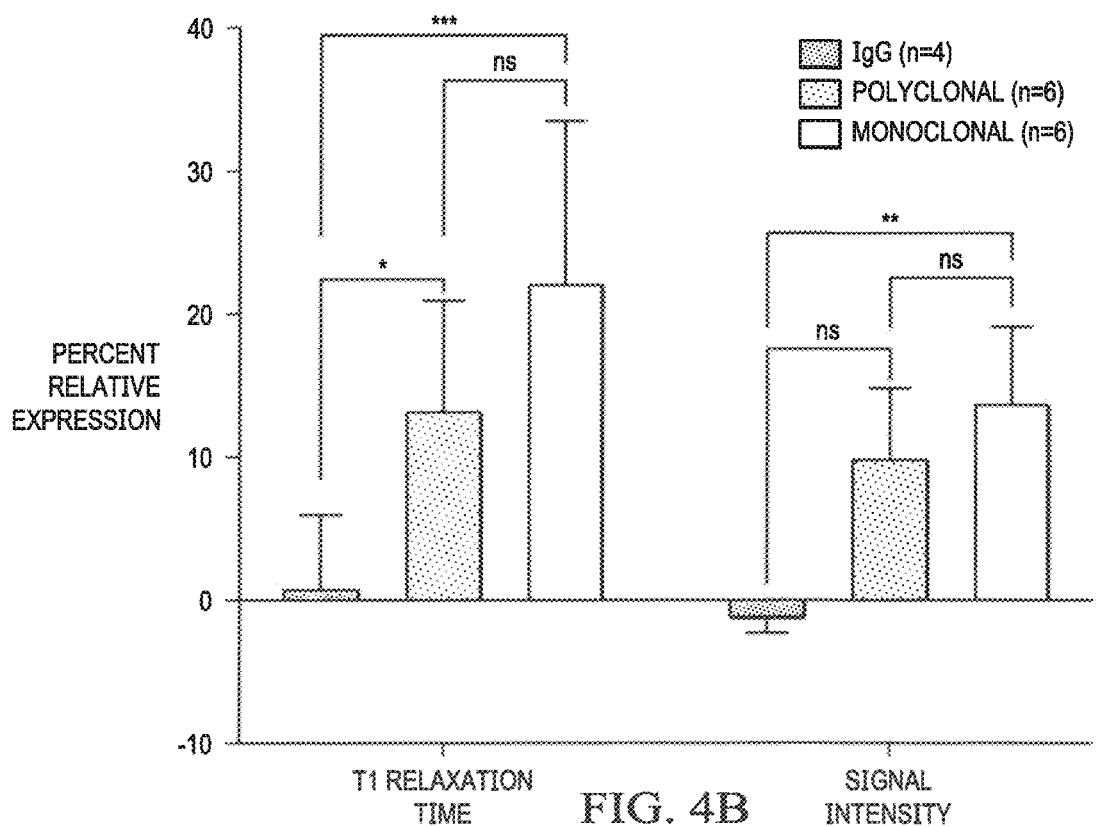

To determine where the Ab was localizing in vivo, the inventors synthesized a biotin-BSA (bovine serum albumin)-Gd-DTPA probe attached to either non-specific IgG, anti-ELTD1 pAb or anti-ELTD1 mAb (FIG. 4A). The molecular probes were injected via tail-vein catheter into untreated G55-glioma bearing mice and T1 relaxation times and signal intensity were calculated via MRI. T1 relaxation is an MRI contrast parameter that is reduced in the presence of the molecular probe of the present invention. The results shown in FIG. 4B demonstrate the presence of the molecular probe as the percent relative expression, due to its effect on T1 relaxation. Both T1 ($p=0.0002$) and signal intensity ($p=0.008$) were significantly increased by the anti-ELTD1 mAb attached probe compared to the non-specific IgG attached probe. The anti-ELTD1 pAb attached probe significantly increased the T1 relaxation ($p=0.0307$) but did not significantly affect the signal intensity ($p=0.0602$).

Figure 4C:
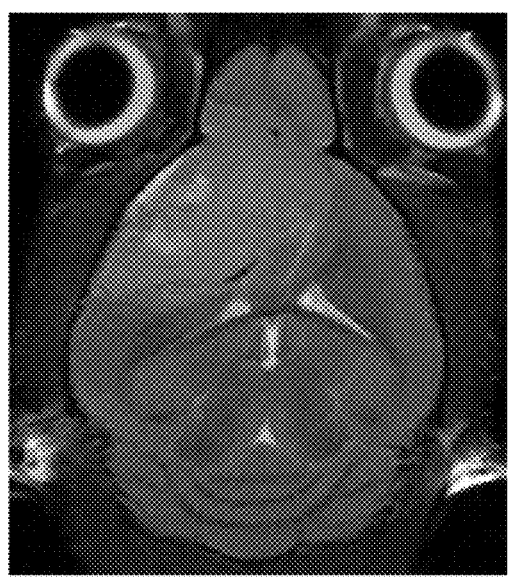
Figure 4D:
Figure 4E:
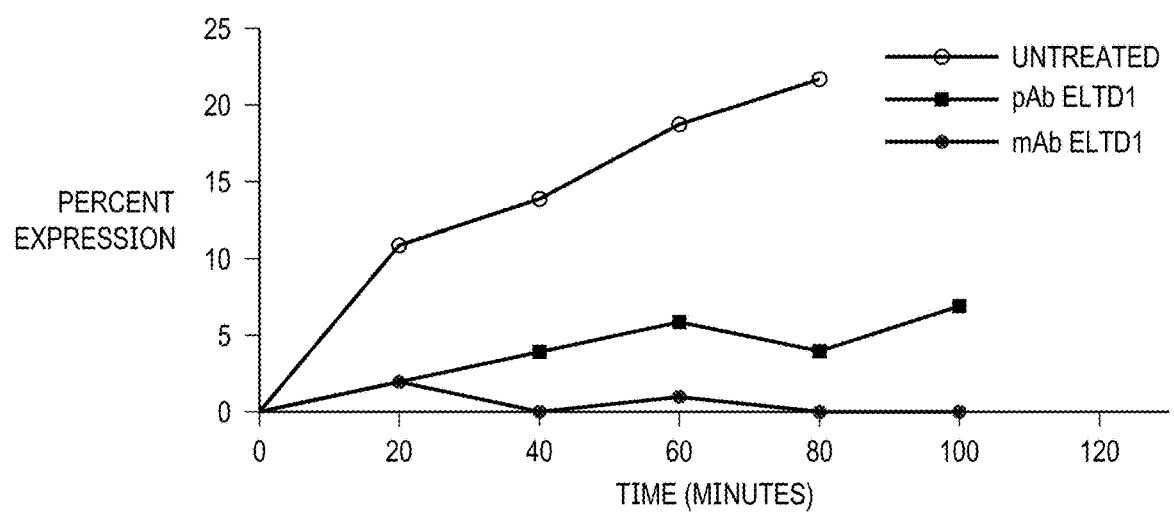

Molecular targeted MRIs of representative anti-ELTD1 mAb and non-specific IgG probe data was overlaid onto morphological images of untreated G55 tumor bearing animals. FIG. 4C demonstrates that the anti-ELTD1 mAb attached probe had an increased binding specificity against the tumor region. The non-specific IgG probe background binding mainly clustered around the blood vessels (FIG. 4D). After monitoring the expression of the molecular probes, the inventors saw that the anti-ELTD1 mAb attached probe had a more profound and sustained effect when compared to both the non-specific IgG and anti-ELTD1 pAb attached probe (FIG. 4E).

Figure 4F:
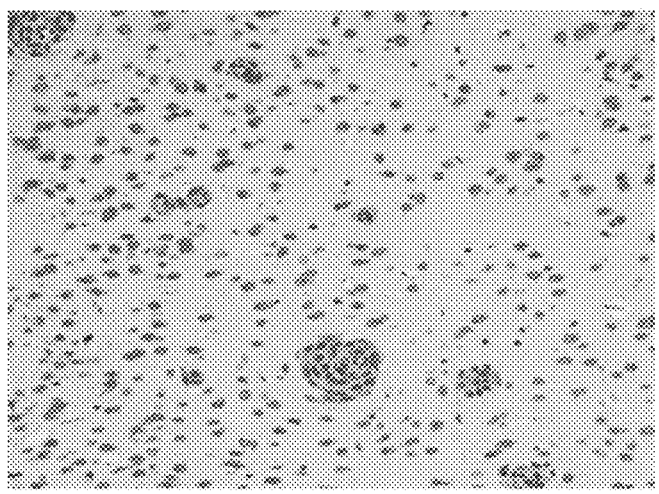
Figure 4G:
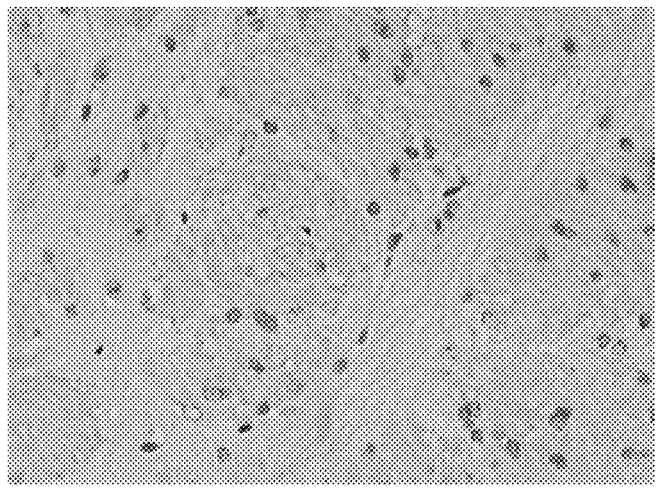
Figure 4H:
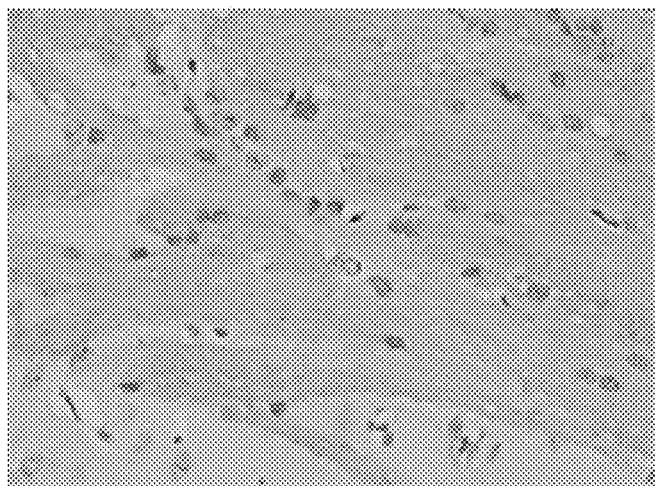

The molecular probe had an attached biotin tag to further localize it in the tissue. Once molecular targeting was concluded, the animals were terminated, and tissues taken for histology. By staining the tumor tissue with SA-HRP the inventors confirmed the molecular targeting results. The anti-ELTD1 mAb and pAb attached probes were localized in the tumor tissue post termination while there were no traces of non-specific IgG attached probes in the tissue. (FIG. 4F-H). This data demonstrates that the anti-ELTD1 mAb-attached probe has significantly higher binding specificity against the tumor region than both the pAb-attached probe and IgG probe.

Figure 5A:
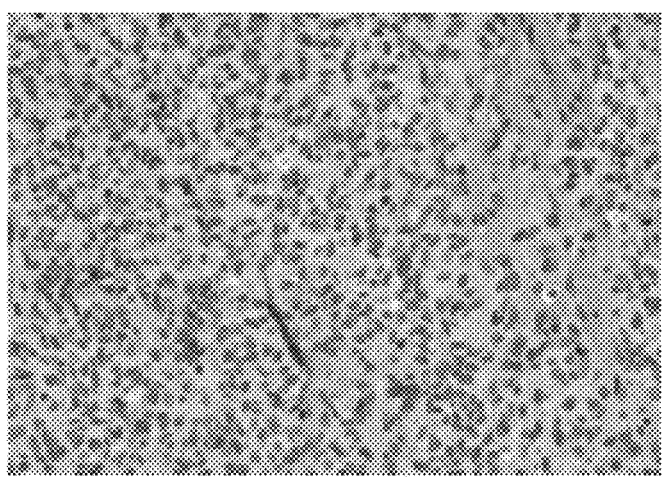
FIGS. 5A to 5E show anti-ELTD1 mAb treatment of mice with GBM significantly decreases Notch1 levels.
Figure 5B:
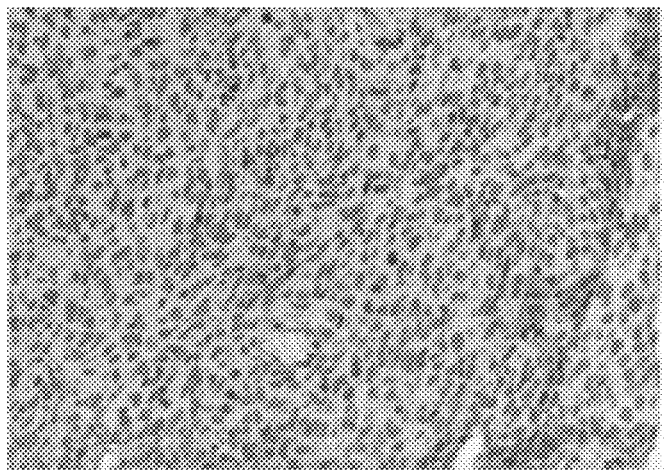
Figure 5C:
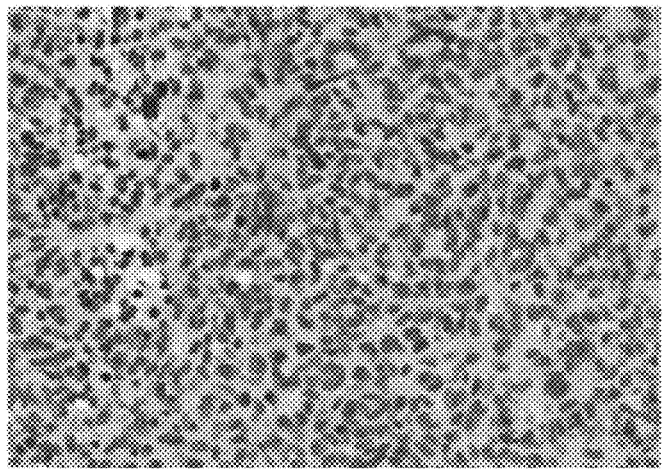
Figure 5D:
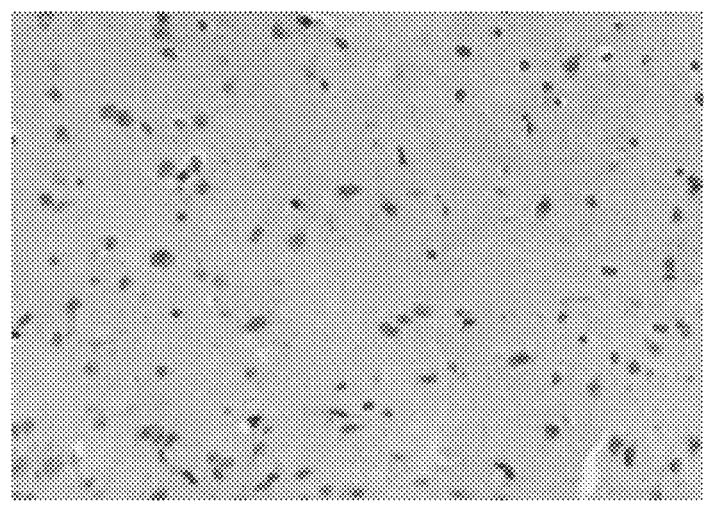
Figure 5E:
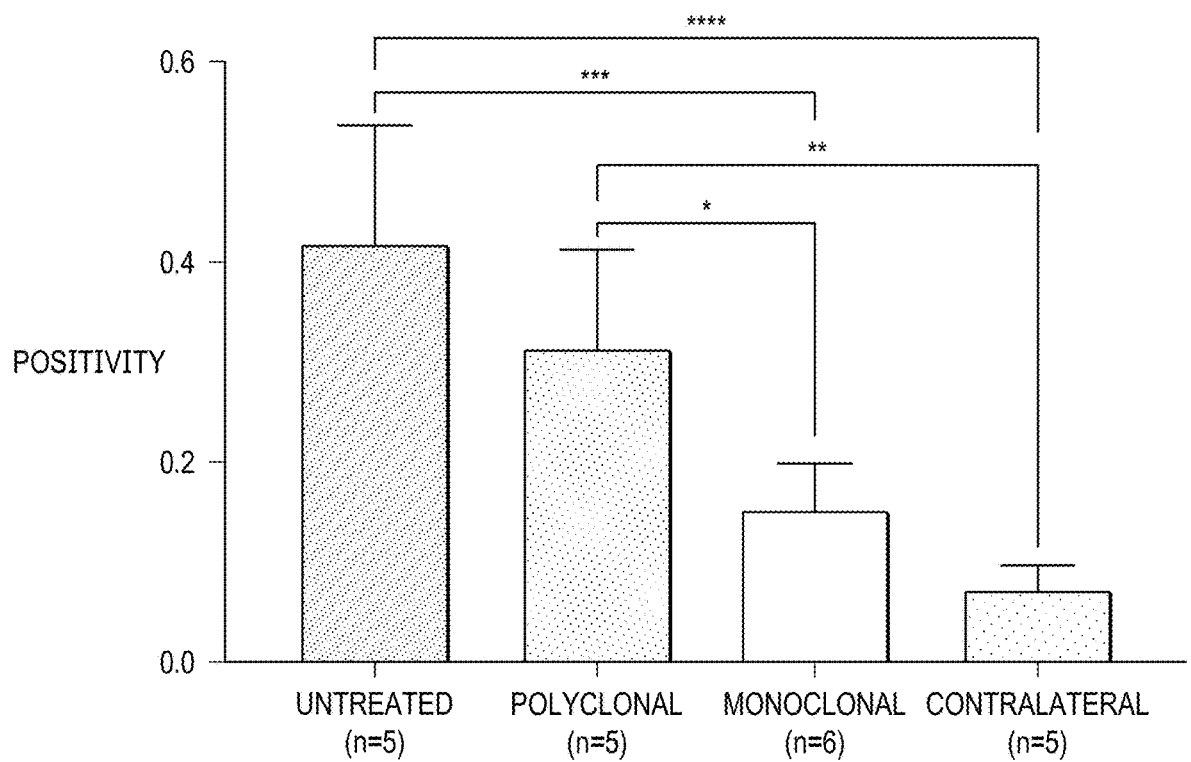

Notch1 signaling is important for cell differentiation, proliferation, as well as tumor angiogenesis and in normal vasculature has been shown to decrease ELTD1 expression [32]. Therefore, the inventors examined if Notch1 levels changed with anti-ELTD1 Ab treatment in tissues of mice with GBM. Positivity analysis of the stained samples demonstrated that the untreated glioma tumor samples had the highest amount of Notch1. The anti-ELTD1 mAb treatment significantly decreased Notch1 expression levels compared to both anti-ELTD1 pAb treatment ($p=0.0357$) and untreated control animals ($p=0.0006$) and brought down the expression to contralateral levels (FIG. 5E).

Figure 6A:
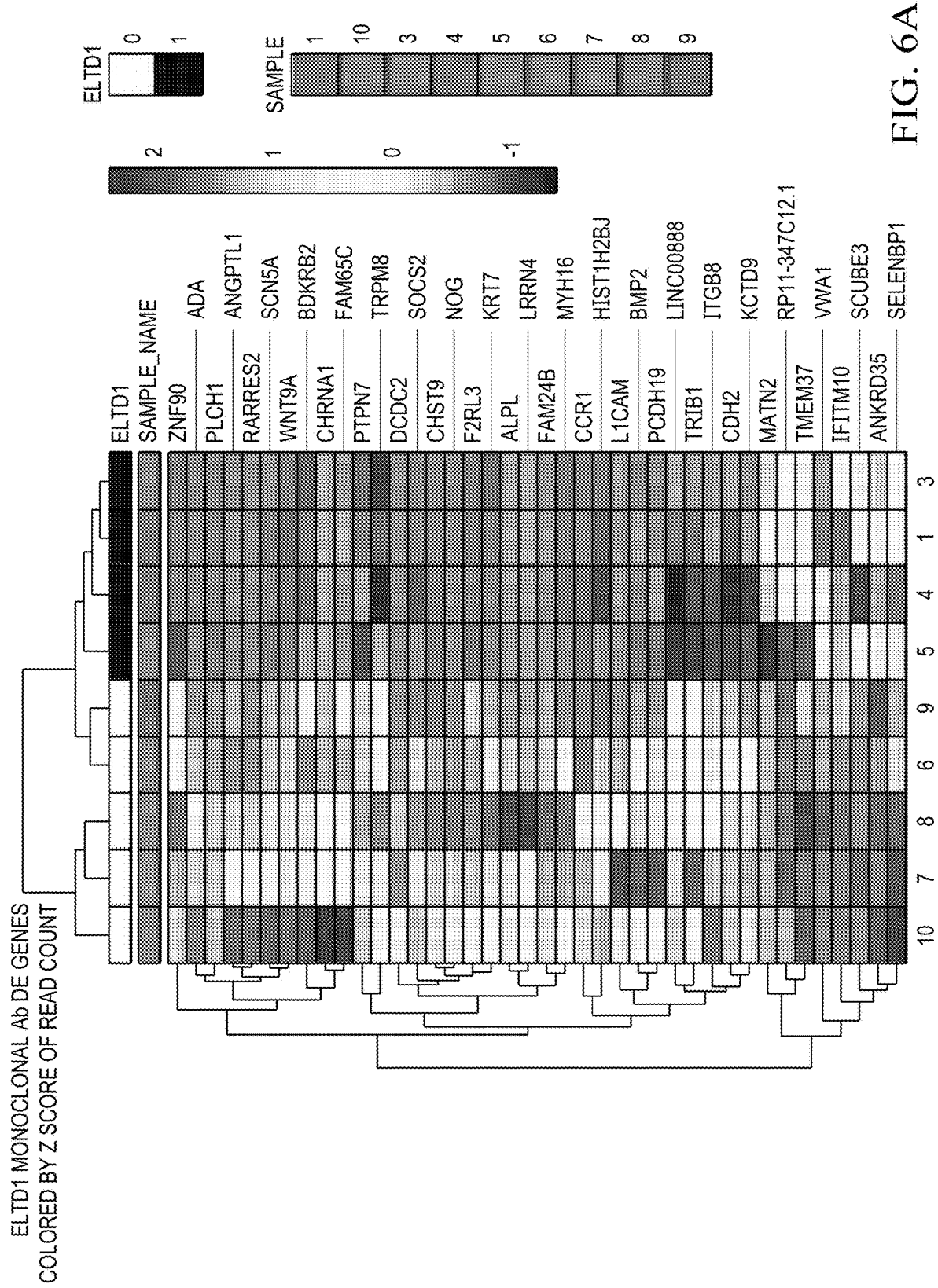
FIGS. 6A and 6B show (FIG. 6A) gene-fold changes when comparing ELTD1 mAb-treated mice with GBM to UT mice with GBM from upregulated (red) to downregulated (blue), obtained from RNA-seq analysis.
Figure 6B:
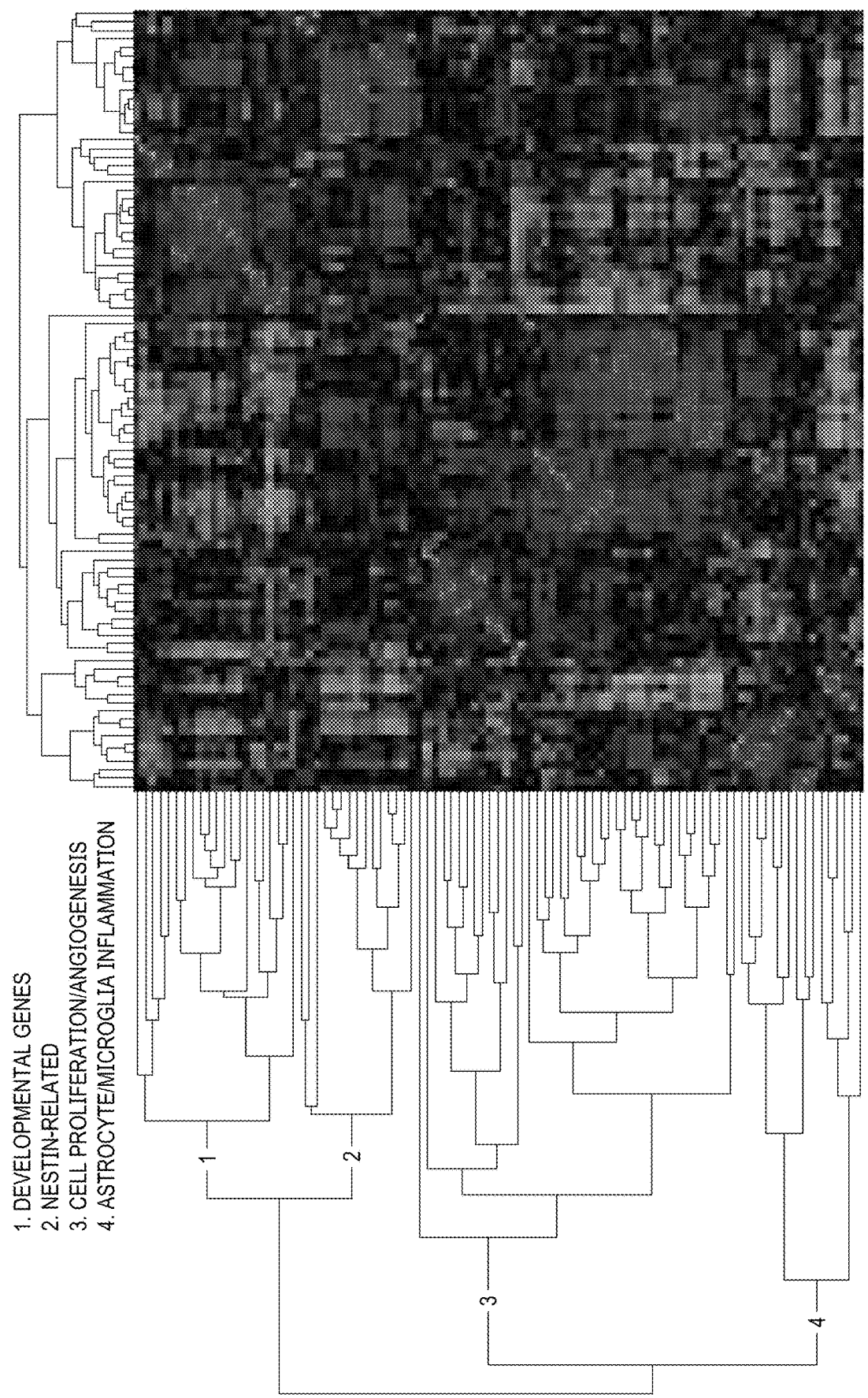

Since in vivo data demonstrated that anti-ELTD1 mAb treatment against ELTD1 was more effective in the G55 xenograft model, the inventors examined the effect that anti-ELTD1 mAb treatment (compared to untreated) had on the genes in the tumor region. From all of the genes found in FIG. 6A, ADA, SCN5A, L1CAM, BMP2, ALPL, TRPM8 (all increased in tumors), SELENBP1 (decreased in tumors) have been directly associated with gliomas. While other genes were associated with various other cancers such as hepatocellular carcinoma (VWA1—decreased [33]), lung cancer (SCUBE3—decreased [34], PLCH1-increased [35], CHRNA1—increased [36], CDH2—increased)[37], and breast cancer (IFITM10—decreased [38], DCDC2—increased [39], CHST9—increased [40], CDH2—increased [41]). To see if some of the genes down-regulated upon anti-ELTD1 mAb treatment had been similarly co-regulated in other experiments, the inventors first calculated gene-gene Pearson's correlations using experiments from the microarray platform GPL570, which are publicly available as part of NCBI's GEO database. FIG. 6B shows the clustered gene-gene correlations of the down-regulated genes using the GPL570 data. Roughly, 4 clusters (developmental genes, nestin-related, cell proliferation/angiogenesis, astrocyte microglia inflammation) are apparent, indicating that groups of genes seen as differentially expressed in these studies match those observed in other experiments.

The following tables summarize the changes in expression caused to the different diseases or conditions using the novel antibodies of the present invention.

TABLE 1

| mAb Anti-ELTD1 Therapy Gene-Fold Changes: Down-regulated >2-fold-Cancer | | | |
|---|---|---|---|
| Gene | >2-fold decrease | Protein | Description |
| SCN5A | −5.11 | Sodium channel protein type 5 subunit alpha | Protein mediates the voltage-dependent sodium ion permeability of excitable membranes |
| | | | Voltage-gated Na+ channels (VGSC) are associated with malignancy progession in breast cancer cells (Mohammed et al., Int J Oncol 2016; 48(1): 73-83) |
| | | | VGSC enhances metastasis (motility, invasion and oncogenic expression) in breast cancer cells (Aktas et al., Acta Biochim Biophys Sin (Shanghai) 2015; 47(9): 680-6) |
| L1CAM | −3.79 | L1 cell adhesion molecule | Protein encoded by this gene is an axonal glycoprotein belonging to the immunoglobulin supergene family |
| | | | Overexpression of L1CAM associated with proliferation and metastasis of pancreatic cancer cells (Zuo et al., Pancreatology 2018; 18(3): 328-333) |

TABLE 2 mAb Anti-ELTD1 Therapy Gene-Fold Changes: Upregulated >2-fold-Cancer

| Gene | >2-fold increase | Protein | Description |
|---|---|---|---|
| CD74 | 3.45 | CD74 molecule, major histocompatibility complex, class II invariant chain | Associates with class II MHC and involved in regulating antigen presentation for immune response. Cell surface receptor for cytokine macrophage MIF, involved in survival pathways and cell proliferation. Highly expressed in thyroid carcinoma (Cheng et al., Endocr Relat Cancer 2015; 22(2): 179-90) |

Through a global microarray meta-analysis (GAMMA) [42] the inventors identified ELTD1, an angiogenic marker, to be highly expressed in high-grade gliomas and other groups have suggested that high ELTD1 expression levels may correlate with the aggressiveness of the glioma [32,43]. Previous studies have demonstrated that anti-ELTD1 pAb treatments were effective in mouse GL261 and human G55 xenograft glioma models [15]. Other groups have also discovered that microRNA-139-5p directly binds onto and targets ELTD1 to inhibit cell proliferation in gliomas [44].

This example focuses on an optimized mAb therapy against ELTD1 in an aggressive human G55 xenograft glioma mouse model. The data show that repetitive I.V. treatments with both anti-ELTD1 pAb and anti-ELTD1 mAb led to a significant decrease in tumor volumes and increase in survival. A prior study by the present inventors showed a survival increase of 7-10 days with anti-ELTD1 pAb treatment, however this current study only showed an average increase of 5 days [15]. The discrepancy between studies is due to the different doubling times between the G55 cells. The 2017 study used high-passaged G55 cells in which the untreated mice had a doubling time of 2.5 days with an average survival of 18 days. However this example used low-passaged G55 cells that appeared more aggressive due to their faster doubling period of 2 days and an average survival of 10 days. The anti-ELTD1 mAb treatment, however, was able to increase the doubling time to approximately 2.7 days even in this more aggressive glioma model.

The optimized anti-ELTD1 mAb treatment was shown to not only return the perfusion levels to normal, depicting a normalization of the vasculature within the tumor region, but was also effective in significantly decreasing the microvessel density (MVD) levels. Together, these data demonstrate that the mAb of the present invention, and its use in mAb therapy against ELTD1, had a more profound effect on the tumor-related microvasculature when compared to both untreated animals and anti-ELTD1 pAb-treated animals.

Prior studies using human G55 cells have shown increased hemorrhaging using anti-VEGF therapy in mice and patients undergoing Avastin treatment [10,15]. The inventors did not observe any hemorrhaging in the anti-ELTD1 pAb- or anti-ELTD1 mAb-treated tumor regions on the MR images, nor when stained with Prussian blue. Therefore, this shows that anti-ELTD1 Ab treatment may be safer for use in the clinic.

Together, these data demonstrated that ELTD1 is an important angiogenic marker in high-grade gliomas. In addition, by using an optimized mAb treatment against ELTD1 against GBM in mice, the inventors were able to significantly increase survival, decrease tumor volume, and normalize the tumor-associated vasculature. These data demonstrate that the optimized mAb against ELTD1 had higher binding specificity when compared to an anti-ELTD1 pAb confirmed through molecular targeting and histology.

Prior studies have stated that ELTD1 expression is increased by VEGF but repressed by Notch/DLL4 interaction in normal vasculature while the present inventors demonstrate that this relationship may be more complex in the tumor environment [12]. The inventors were able to significantly reduce Notch1 protein levels within the tumor to levels near that of contralateral normal tissue with the anti-ELTD1 mAb treatment. Furthermore, RNA-sequencing data demonstrated that 3 of the genes (SCN5A, L1CAM, BMP2) affected with the anti-ELTD1 mAb treatment are directly associated with gliomas and are known to influence and interact with Notch signaling. Therefore, ELTD1 has a more complex relationship with Notch1 than previously understood.

Aside from the possible relationship with Notch, the RNA-seq data gave further insight as to what pathways the anti-ELTD1 Ab treatment is targeting. ADA and BMP2 expression is correlated with poor prognosis in glioma patients [45,46], which were both downregulated with the anti-ETLD1 treatments. Furthermore, the anti-ELTD1 treatment worked to downregulate SCN5A, TRPM8 and BMP2, which were all shown to increase glioma cell proliferation, migration, and invasion [47-49]. Alkaline phosphatase (ALPL) is a stem cell marker, that is highly expressed around necrotic areas within the tumor, and high expression of ALPL and CD133 (another stem cell marker) have been associated with poor prognosis for patients [50]. The anti-ELTD1 mAb therapy was successful in downregulating ALPL. CD133+ glioma cells show neurosphere-like growth, drive tumor formation, and are resistant to standard therapies [51]. L1CAM, a gene downregulated by anti-ELTD1 treatment, is overexpressed in GBMs and CD133+ glioma cells, and regulates neural cell growth, migration, and survival during development [52,53]. Furthermore, targeting and inhibiting L1CAM in CD133+ glioma cells suppressed tumor growth and increased the survival in a glioma xenograft model [54]. Glioma stem cells (GSC) are the main cause of GBM recurrence after therapy and are characterized by CD133 [55]. However, recent reports have shown that CD133 may not be a robust marker for GSC and CD133-cells that possess GSC properties may give rise to aggressive tumors [55,56]. Nestin, was first characterized as a neuronal stem cell marker and found on the surface of both CD133-positive and -negative cells and may serve as a more efficient GSC marker in GBMs [55,56]. Furthermore, nestin has been shown to be a key player in proliferation, migration, and survival of GBMs and other cancers [57-59]. Interestingly, cluster gene-gene analysis from the genes downregulated by the anti-ELTD1 treatment suggests that there is a down-regulation response for nestin related pathways.

These data demonstrate that an optimized anti-ELTD1 mAb is a potential anti-angiogenic therapy against GBMs.

Although discovered in 2001, there are various unknowns about ELTD1, including its mechanism of action and its ligand.

Example 3

In this present example, an anti-ELTD1 single chain variable fragment (scFv) was generated and shown to maintain binding of the 430 AA external region of ELTD1 in a G55 glioma xenograft preclinical model. The inventors used morphological MRI to assess tumor volumes, and perfusion imaging to measure vascular changes following anti-ELTD1 scFv compared to anti-ELTD1 mAb treatment in tumor regions. Animal survival was also determined following anti-ELTD1 scFv or anti-ELTD1 mAb treatments. Through the use of mt-MR imaging, the inventors also assessed the binding affinity and specificity of anti-ELTD1 scFv fragment as a probe.

Preparation of recombinant extracellular domain of ELTD1 human Ckappa fusion protein was as described hereinabove in Example 2. Generation of anti-ELDT1 Abs was as described hereinabove. The enzyme immunoassay was as described hereinabove. G55 Xenograft model and treatment was as described hereinabove. In vivo magnetic resonance (MR) techniques were as described hereinabove. Immunohistochemistry and standard staining were as described hereinabove. Statistical analysis was as described hereinabove.

Figure 7A:
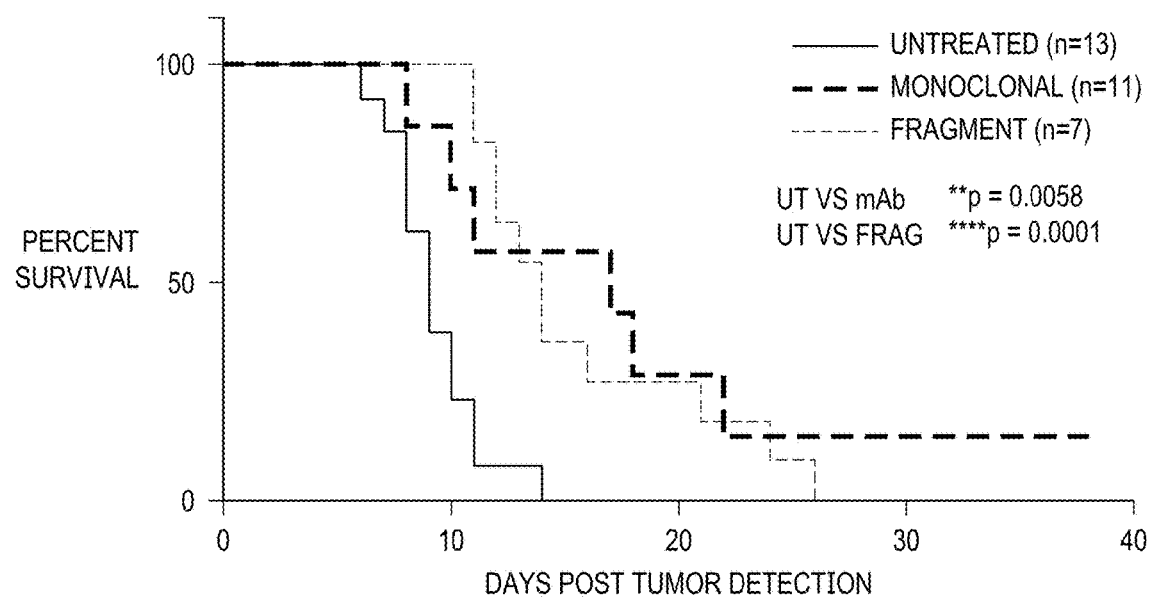
FIGS. 7A to 7E show that anti-ELTD1 treatments were successful in increasing percent survival post GMB tumor detection as well as decreasing tumor volumes.
Figure 7B:
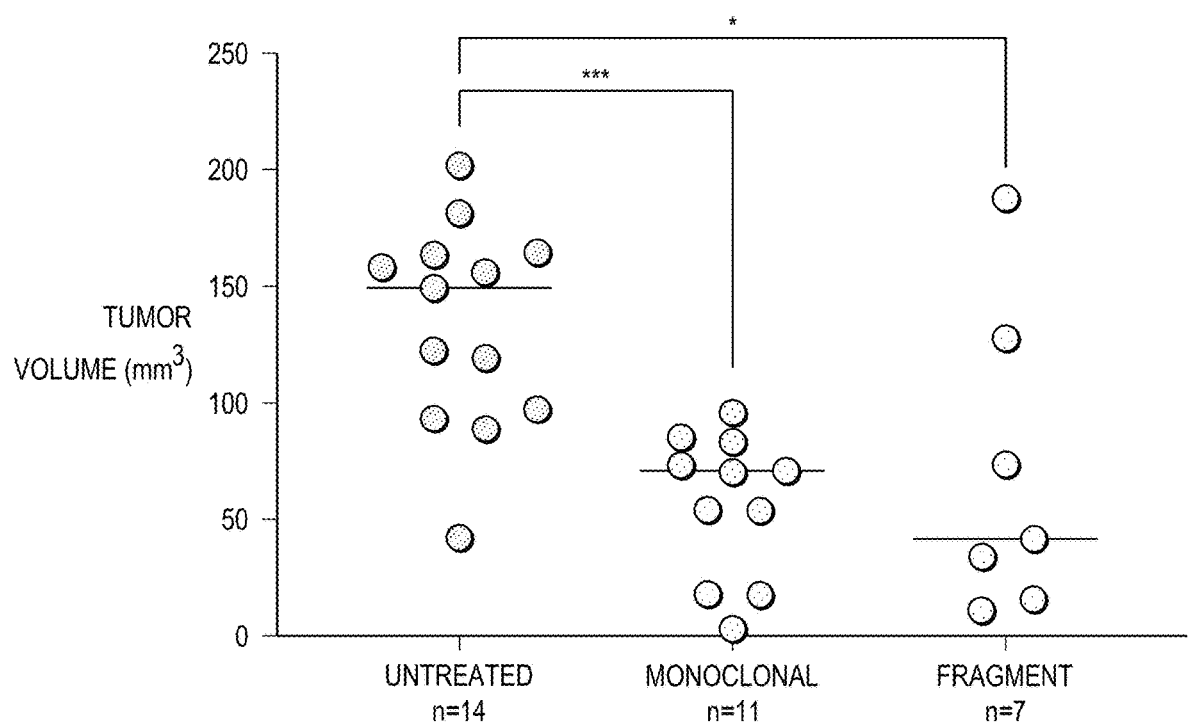
Figure 7C:
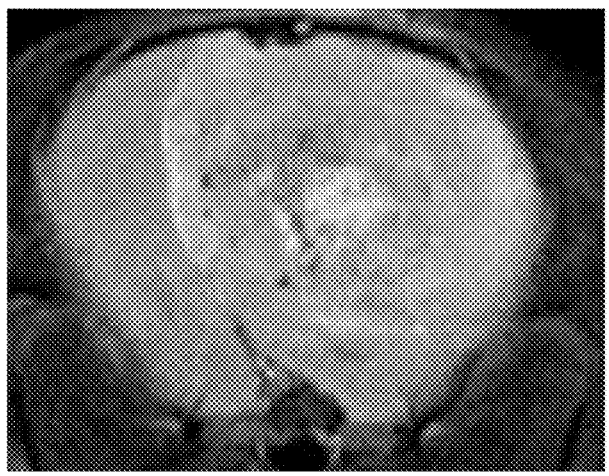
Figure 7D:
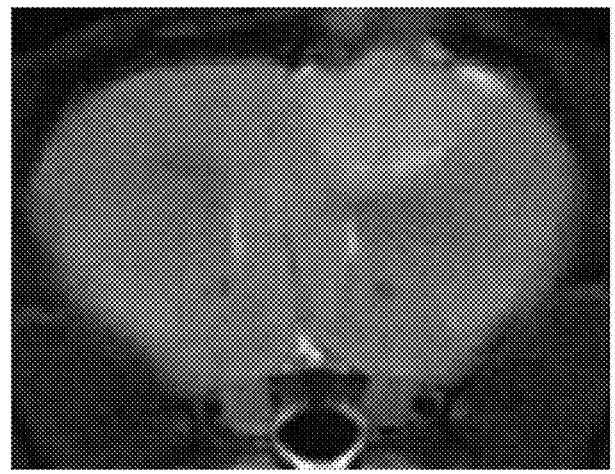
Figure 7E:
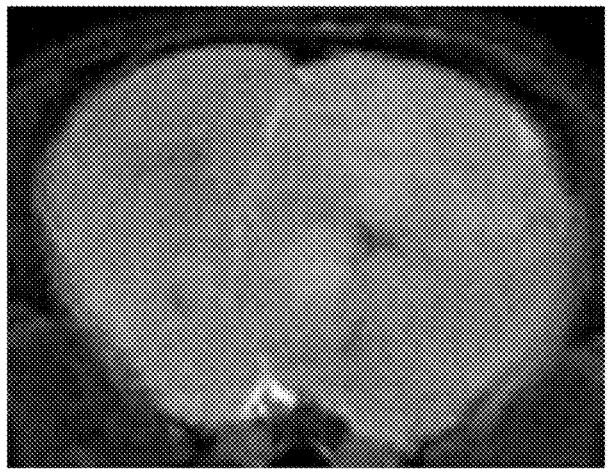

The inventors intracerebrally implanted human G55 cells into two-month old male Athymic Nude mice. Tumor growth was monitored via morphological MR Imaging and upon tumor detection (6-7 $mm^3$) treatments were administered every 3-4 days via tail-vein with either the monoclonal anti-ELTD1 mAb or anti-ELTD1 scFv (also referred to as fragment in this manuscript). The percent survival post tumor detection of G55-glioma bearing mice was significantly higher with both the anti-ELTD1 mAb (*p=0.0058) and anti-ELTD1 scFv (*p=0.0001) treatment as depicted in FIG. 7A. The untreated group had an average survival of 9 days and therefore the inventors compared the tumor volumes at day 9 post tumor detection. Tumor volumes at 9 days post tumor detection were significantly lower with the anti-ELTD1 Ab treated mice (mAb *p=0.0009; scFv fragment *p=0.017) when compared with untreated controls (FIG. 7B). Representative MRIs of G55 tumor-bearing mice from all treatment groups are shown in FIG. 7C-E.

Figure 8A:
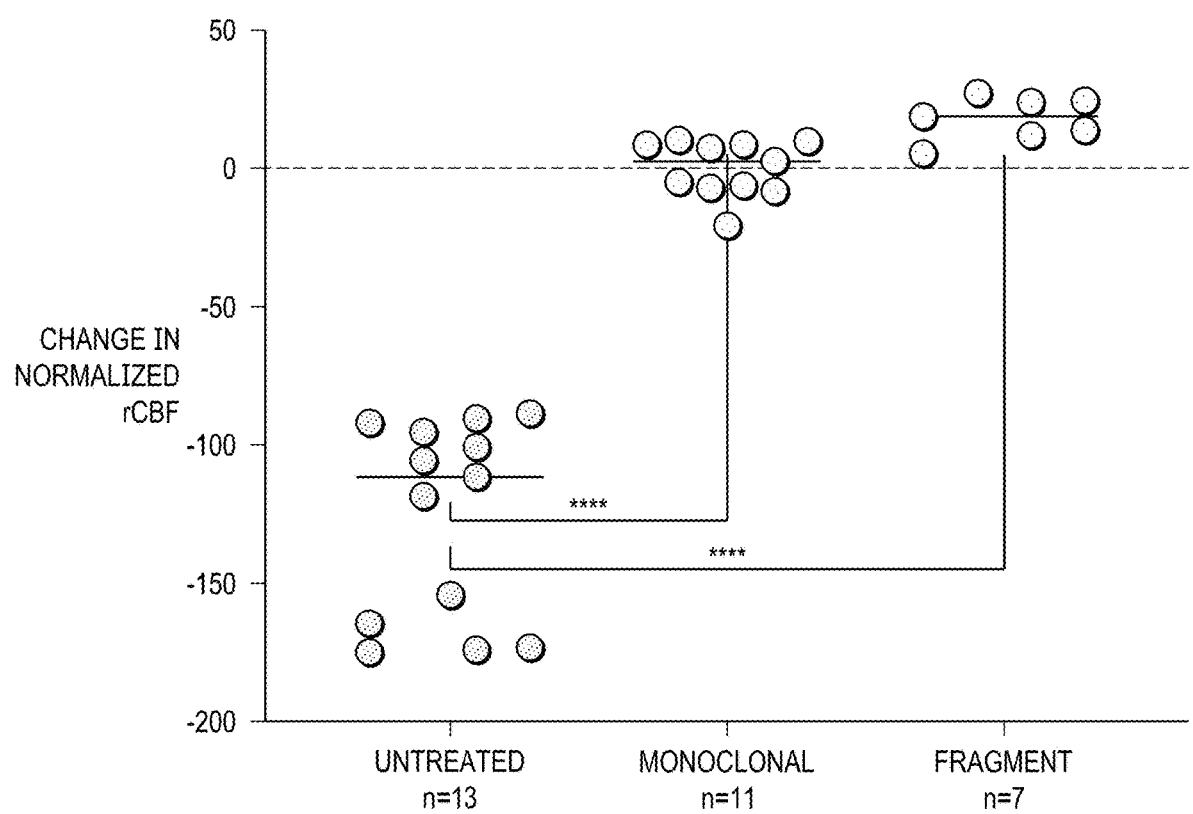
FIGS. 8A to 8G show that relative cerebral blood flow (rCBF) was normalized with the anti-ELTD1 Ab treatments of mice with GBM.
Figure 8B:
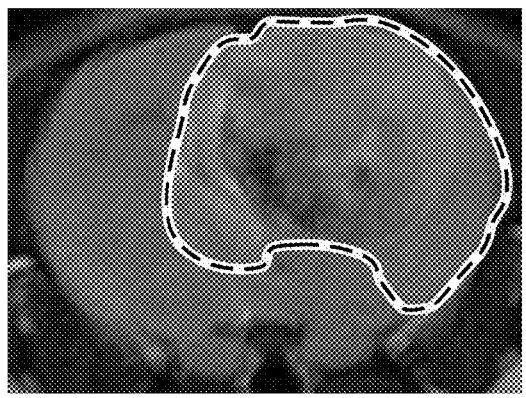
Figure 8C:
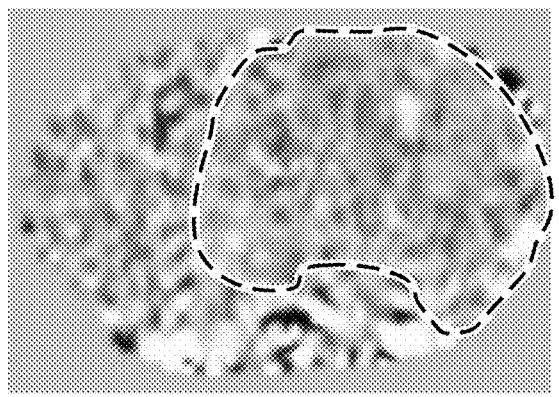
Figure 8D:
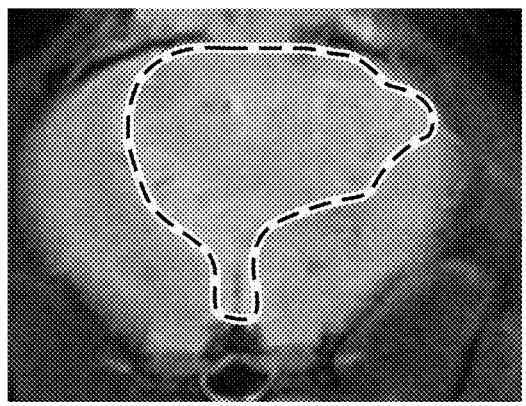
Figure 8E:
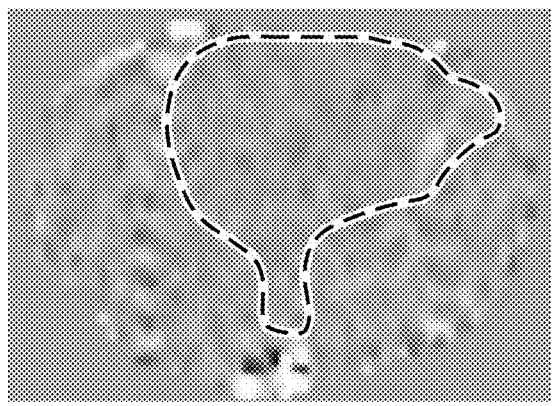
Figure 8F:
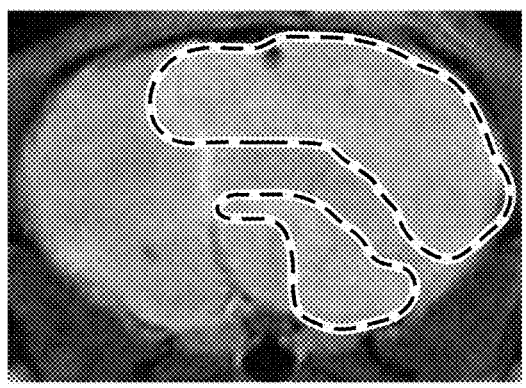
Figure 8G:
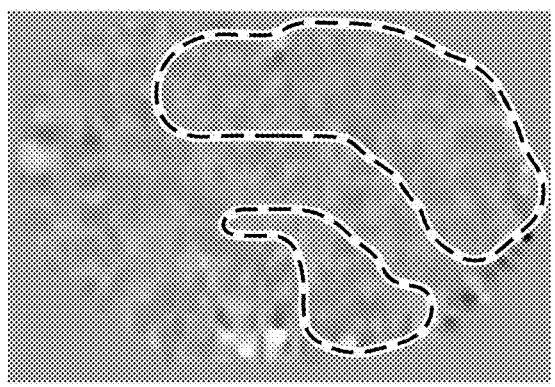
Figure 9A:
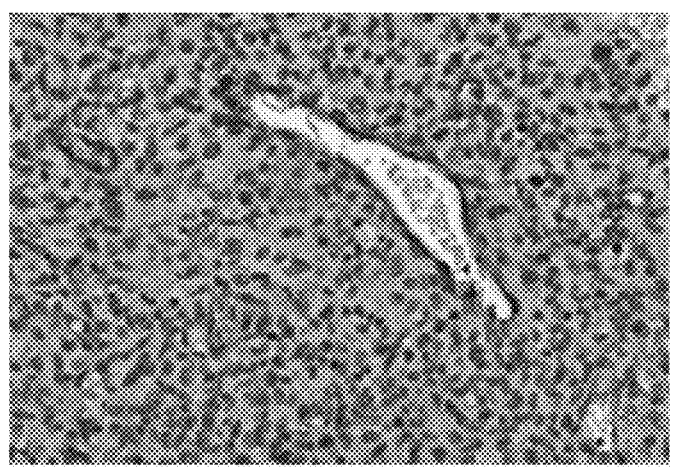
FIGS. 9A to 9D show that anti-ELTD1 Ab treatment of mice with GBM significantly decreased tumor associated vasculature. MVD was analyzed with Aperio ImageScope for the treatment groups. Representative IHC images (20×) of CD34 staining for untreated (FIG. 9A), anti-ELTD1 mAb-treated (FIG. 9B) and scFv fragment-treated (FIG. 9C) animals are shown. Arrows are pointing to the vessels found in the tumor region.
Figure 9B:
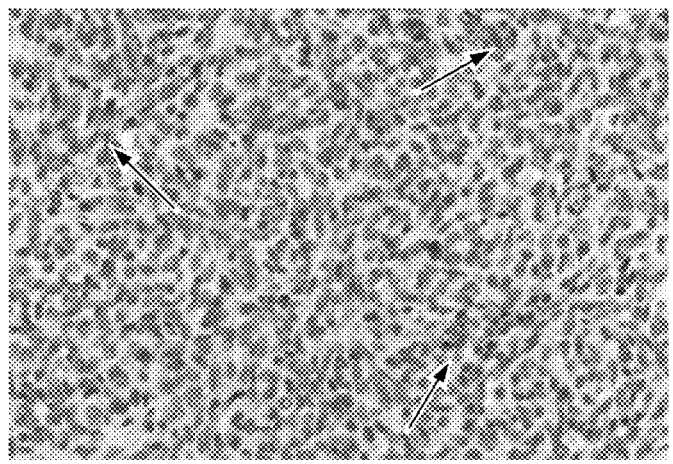
Figure 9C:
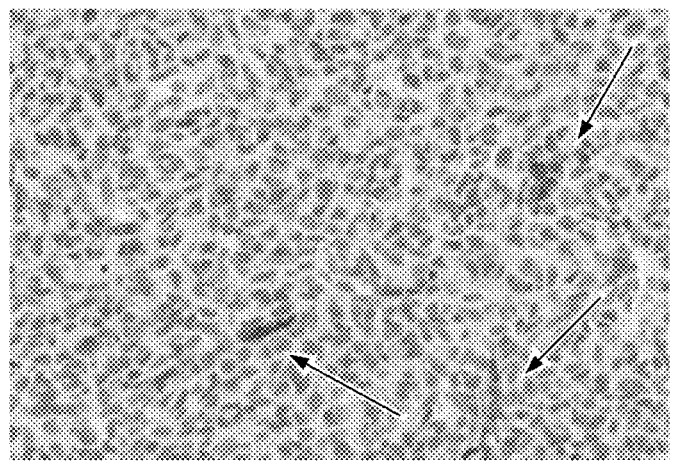
Figure 9D:
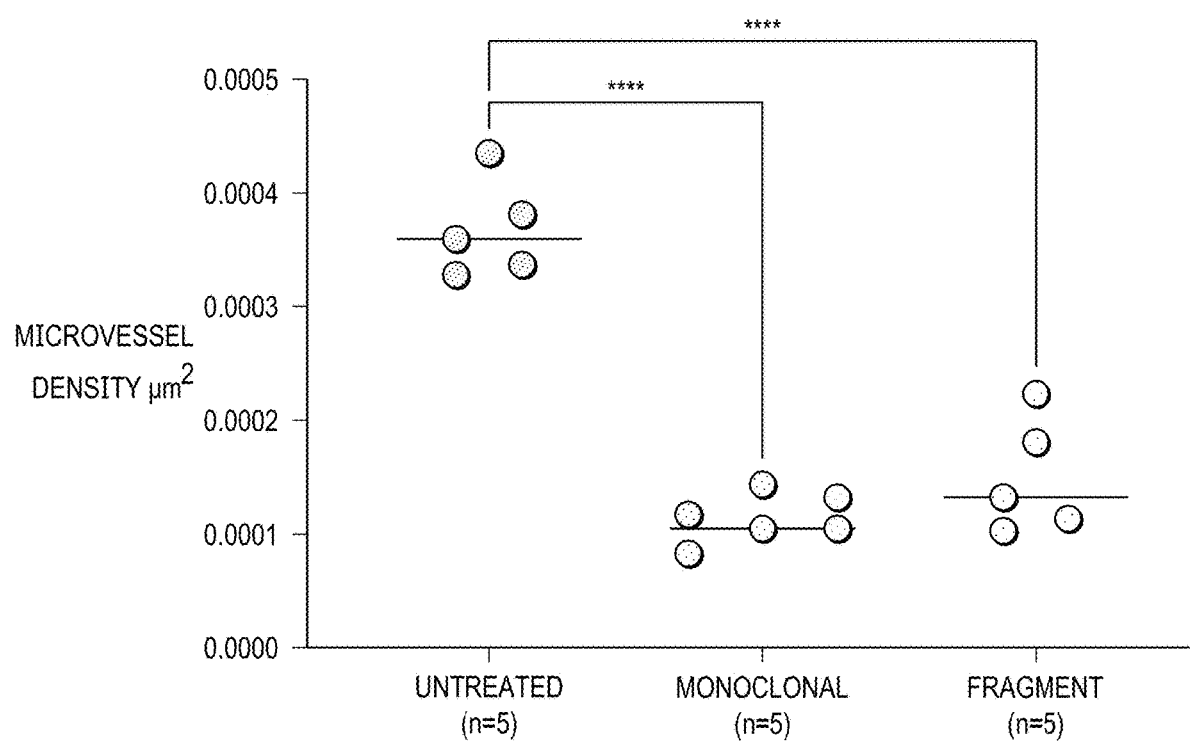

Anti-ELTD1 treatment targets angiogenesis, therefore the inventors examined if the treatments had an effect on the microvasculature. Tumor microvascular changes associated with tumor angiogenesis can be measured through the decrease of relative cerebral blood flow (rCBF). As the vasculature within the tumor region grows, it exponentially becomes more chaotic therefore decreasing the perfusion rate. Perfusion scans performed with MRI demonstrated a characteristic decrease in rCBF in the tumor region of untreated animals (FIG. 8A). The perfusion values in mice treated with anti-ELTD1 Ab treatments were significantly improved when compared to untreated animals (p<0.0001 for both). The anti-ELTD1 mAb treatment showed a normalization of perfusion values, while the anti-ELTD1 scFv fragment treated animals had a slight increase of perfusion (FIG. 8A). FIGS. 8C, 8E, 8G show representative perfusion scans for each group. The untreated perfusion scan (FIG. 8C) has distinct dark regions only within the tumor region (outlined by the yellow dashed line) depicting the decrease in perfusion within the region. However, the tumor regions in the perfusion scans of the anti-ELTD1 mAb- (FIG. 8E) and anti-ELTD1 scFv fragment (FIG. 8G)—treated mice are homologous with the contralateral tissue. Furthermore, the effect anti-ELTD1 Ab treatment on the tumor associated vasculature was determined. Both of the anti-ELTD1 Ab therapies significantly decrease the microvessel density levels (MVD) (p<0.0001) in the tumor region when compared to untreated animals (FIG. 9D). Representative CD34 IHC images for all of the treatment groups are shown in FIGS. 9A-C.

Figure 10A:
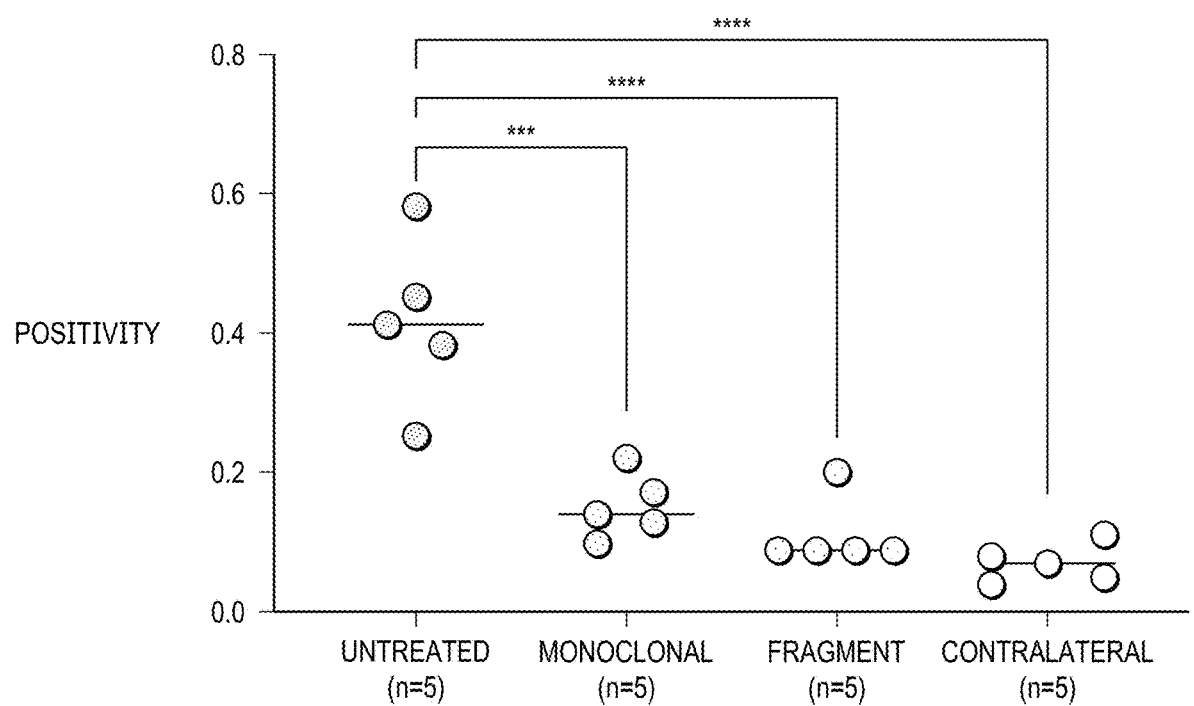
FIGS. 10A to 10E show that anti-ELTD1 Ab treatments of mice with GBM decreased Notch1 levels. Notch1 positivity was analyzed with Aperio ImageScope for the treatment groups (FIG. 10A) Notch1 positivity staining for all treatment groups. Contralateral normal tissue had significantly decreased Notch1 staining compared to UT animals. Both anti-ETLD1 treatments were successful in decreasing and normalizing Notch1 levels to those seen in contralateral tissue. Representative IHC images (20×) of Notch1 staining of tumor tissue from untreated mice (FIG. 10B), anti-ELTD1 mAb treated mice (FIG. 10C), scFv fragment treated mice (FIG. 10D), and contralateral control tissue (FIG. 10E) (*$p=0.0001$, **$p<0.0001$).

ELTD1 expression has been demonstrated to be upregulated by VEGF and downregulated by Notch/DLL4 in normal vasculature [33]. In previous studies, the inventors examined the relationship between VEGF and ELTD1, and discovered that by targeting ELTD1, VEGFR2 (the receptor of VEGF) levels were decreased in a glioma model [31]. Therefore, in this example the inventors again determined if anti-ELTD1 Ab treatments had an effect on Notch1. Tissue from glioma-bearing mice from each group was stained with for Notch1 and the positivity was analyzed. The inventors sought to characterize the difference in Notch1 positivity levels between tissue in the tumor region and contralateral normal tissue. FIG. 10A demonstrates that the positivity levels in the contralateral tissue was significantly lower (p<0.0001) when compared to the levels in the tumor region of untreated animals. Furthermore, our anti-ELTD1 mAb and anti-ELTD1 scFv fragment treatments were successful in significantly decreasing Notch1 levels (p=0.0001 and p<0.0001 respectively) within the tumor region and were able to bring them to a level similar to that of normal contralateral tissue (FIG. 10A). Representative tissue images shown in FIGS. 10B-10E depict the decreased Notch1 staining within the anti-ELTD1 Ab-treated tumor regions.

Figure 10B:
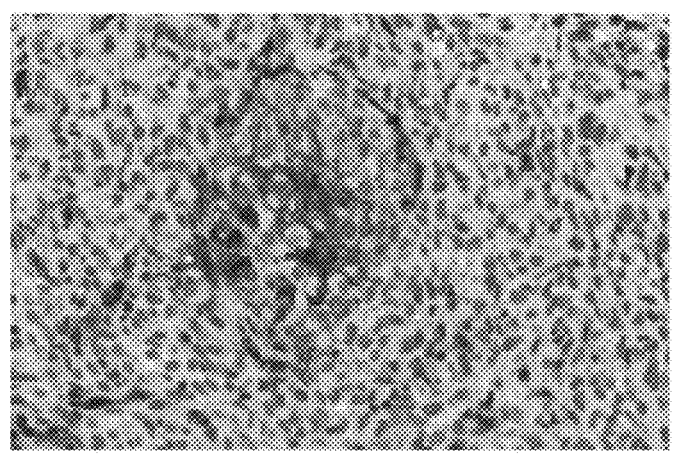
Figure 10C:
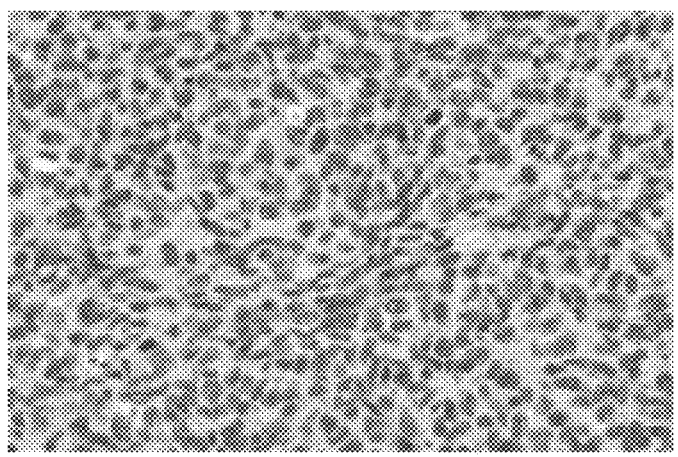
Figure 10D:
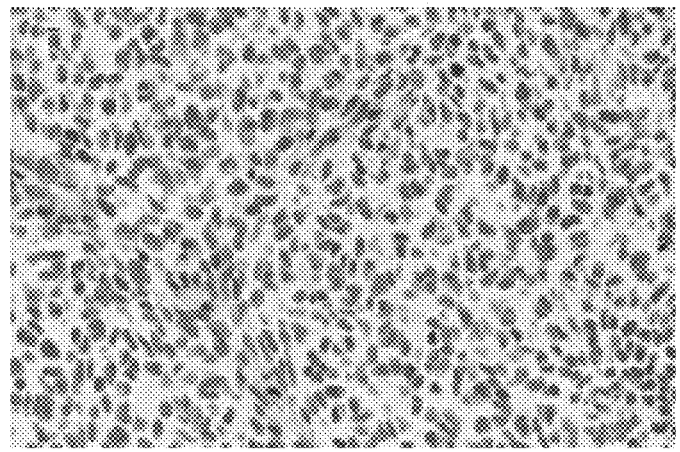
Figure 10E:
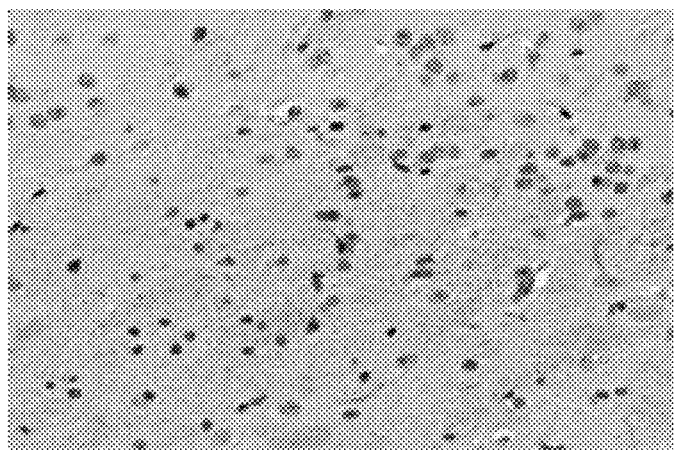
Figure 11A:
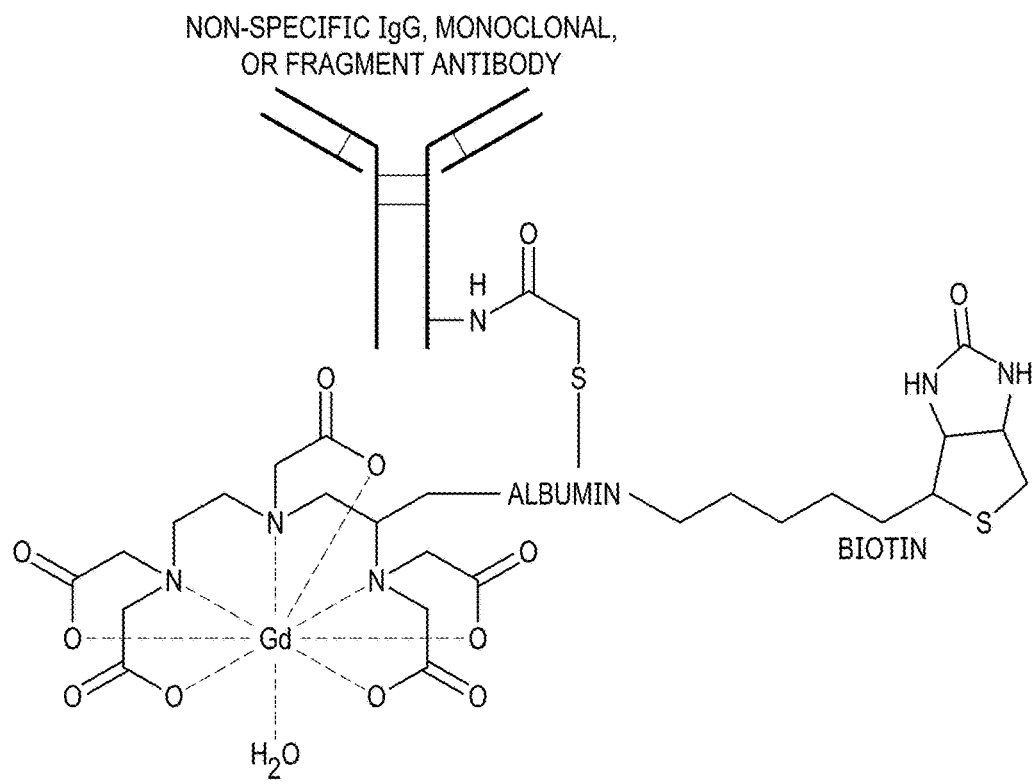
FIGS. 11A to 11D show that the anti-ELTD1 Ab attached probes were successful in reaching and infiltrating the tumor region.
Figure 11B:
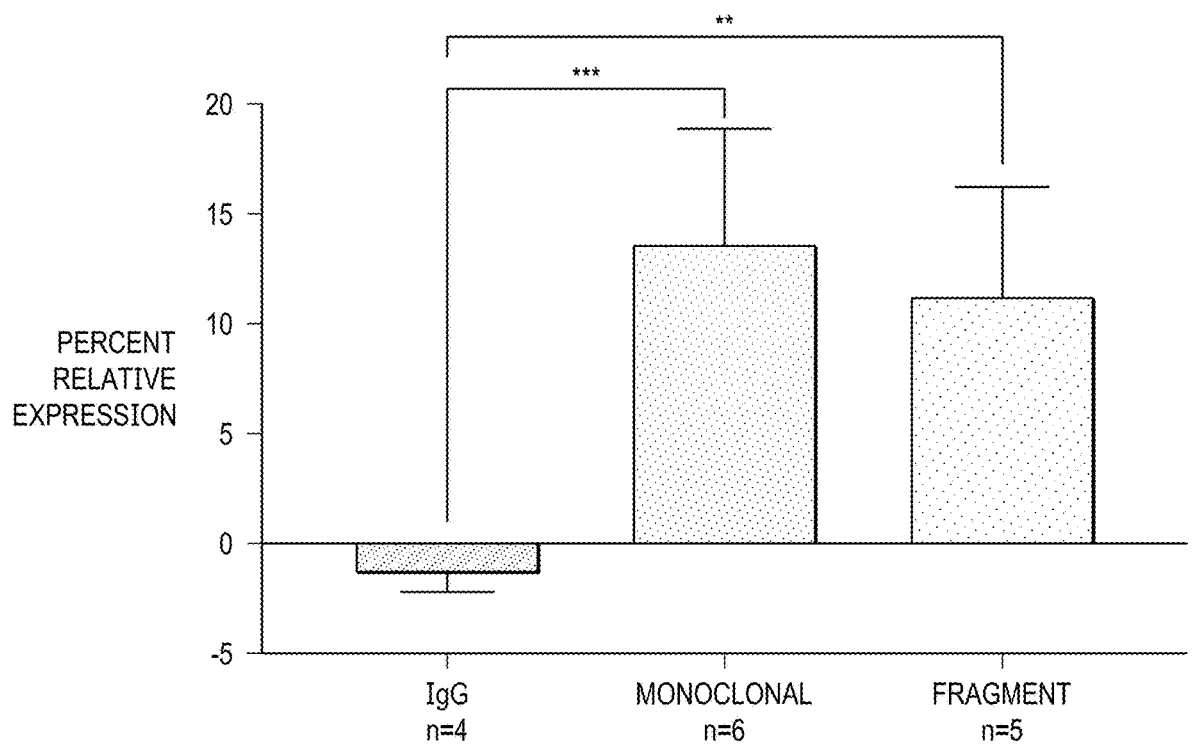

To determine whether the antibody treatments were crossing the blood-brain-barrier (BBB) and were responsible for the previous results shown above, the inventors attached either non-specific IgG, anti-ELTD1 mAb, or anti-ELTD1 scFv fragment onto a molecular probe previously described (albumin-biotin-Gd-DTPA) and shown in FIG. 11A. The molecular probes were injected via tail-vein into untreated glioma-bearing animals and were monitored via MR molecular targeting imaging. The Gd-DTPA attached onto our molecular probes allows the determination of where the probe is attaching and allows measurements of signal intensity within the tumor region. FIG. 10B demonstrates that the non-specific IgG attached probe was a suitable control because the signal intensity was at baseline after 90 minutes. Differences in signal intensity, however, were significantly higher for the anti-ELTD1 mAb and anti-ELTD1 scFv fragment attached molecular probes shown in FIG. 11B (p=0.0007 and p=0.0038, respectively). Furthermore, FIG. 11C demonstrates how the anti-ELTD1 mAb attached probe localized within the tumor region over the course of 90 minutes. The anti-ELTD1 scFv fragment attached probe had slightly decreased signal intensity 90 minutes post injection, therefore the inventors examined the binding of the molecular probe for up to 180 minutes. FIG. 11D demonstrates that the fragment attached probe requires a longer time to bind onto and localize in the tumor region.

Figure 11C:
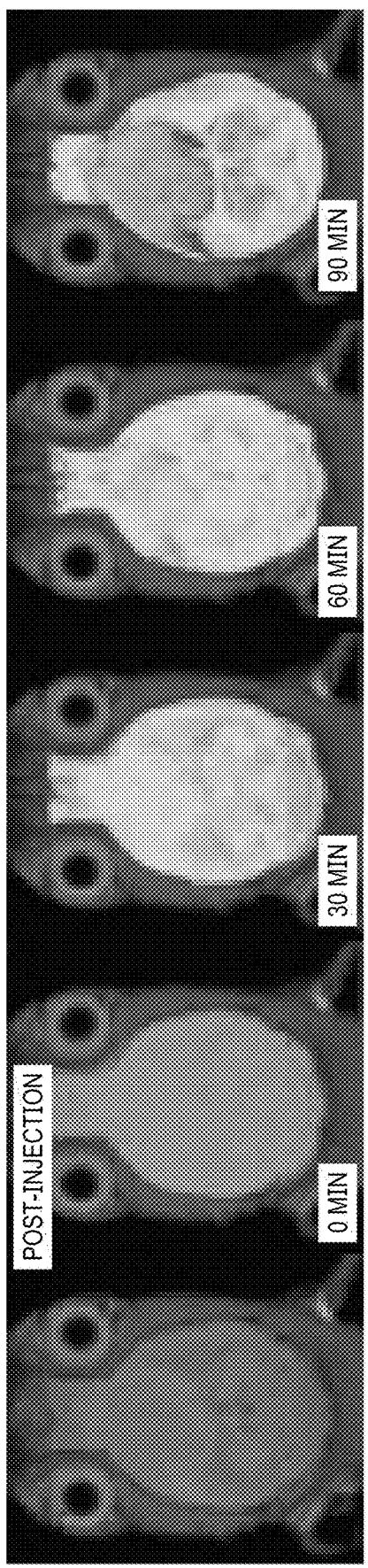
Figure 11D:
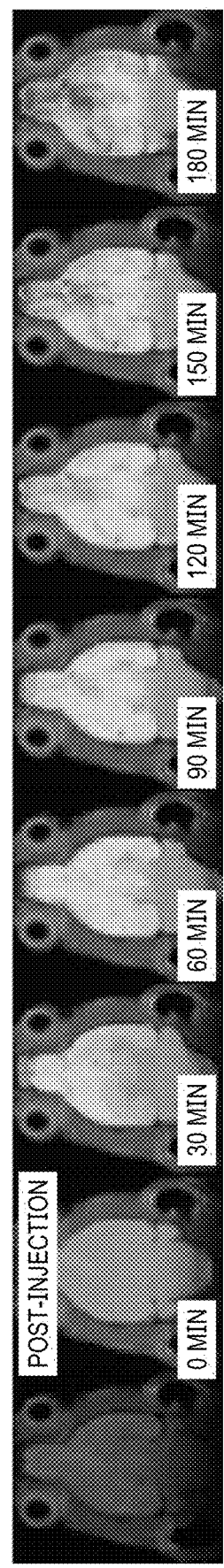
Figure 12:
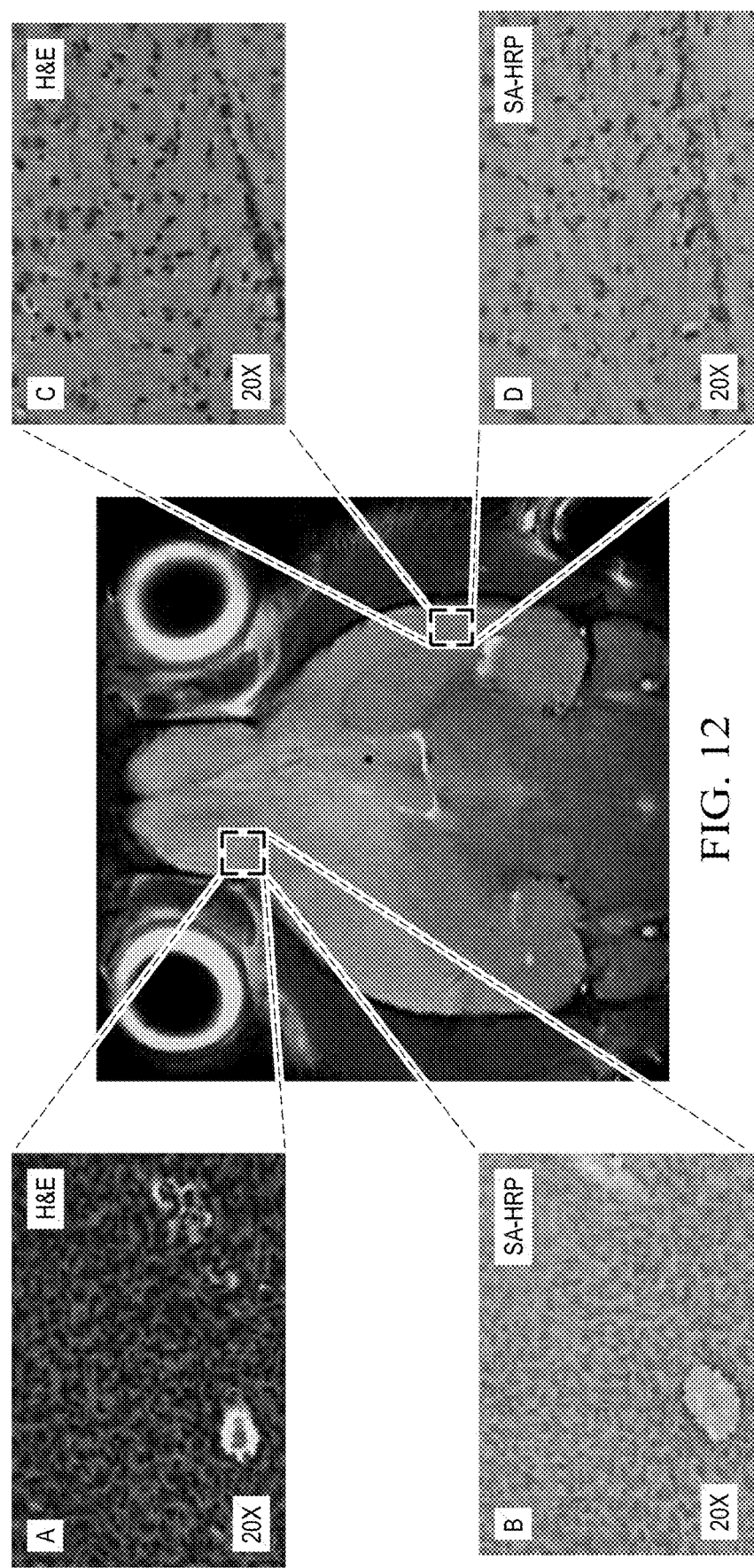

The anti-ELTD1 scFv fragment-attached probe did not only localize in the bulk tumor seen through MRI, but also bound around other regions thought initially not to be tumor tissue, as seen in the last frame of FIG. 11C. The glioma tissue was then stained with SA-HRP, which binds onto the biotin tag attached on the molecular probe, to further examine the regions to which the probe bound. The anti-ELTD1 scFv fragment-attached probe was successful in reaching the bulk tumor as shown through SA-HRP staining depicted in the top voxel in FIG. 12. Furthermore, H&E analysis of the tissue discovered that there were extremely diffuse tumor regions along the lateral cortex regions of the brain, which the probe successfully bound onto, as shown in the last frame of FIG. 12C. The molecular probe was also found through SA-HRP staining in the diffuse tumor regions as seen in the bottom, right voxel in FIG. 12.

Example 4. Retinopathy

Using the antibodies of the present invention in a retinopathy model, the following changes in RNA expression were determined.

TABLE 3 mAb Anti-ELTD1 Therapy Gene-Fold Changes: Down-regulated >2-fold

| Gene | >2-fold decrease | Protein | Description |
| --- | --- | --- | --- |
| ADA | −4.53 | Adenosine deaminase | Catalyzes the hydrolytic deamination of adenosine and 2-deoxyadenosine |
|  |  |  | Causal role of ADA2 in inflammation; Increased ADA2 associated with diabetic retinopathy (Fulzele et al., Biomed Res Int 2015; 846501) |
| APLN | −2.81 | apelin | Gene encodes a peptide that functions as an endogenous ligand for the G protein coupled receptor APJ |
|  |  |  | Apelin is associated with retinal neovascularization (McAnally et al., PLoS One 2018; 13(9): e0202436; Ishimaru et al., Sci Rep 2017; 7(1): 15062) |

Example 5. Tissue Regeneration

Using the antibodies of the present invention in a tissue regeneration model, the following changes in RNA expression were determined.

TABLE 4 mAb Anti-ELTD1 Therapy Gene-Fold Changes: Upregulated >2-fold

| Gene | >2-fold increase | Protein | Description |
| --- | --- | --- | --- |
| BGLAP | 3.52 | bone gamma-carboxyglutamate (gla) protein | BGLAP has 4,051 functional associations with biological entities spanning 8 categories (molecular profile, organism, chemical, functional term, phrase or reference, disease, phenotype or trait, structural feature, cell line, cell type or tissue, gene, protein or microRNA). |
|  |  |  | Thought to stabilize healing phase (Ghiacci et al., Biomed Mater 2017; 12(4): 045016) |
| MATN2 | 3.48 | matrilin 2 | Gene encodes member of von Willebrand factor A domain containing protein family. Thought to be involved in the formation of filamentous networks in the extracellular matrices of various tissues. |
|  |  |  | Required for regeneration of muscle, nerve and other tissues in wound healing (Korpos et al., Neural Regen Res 2015; 10(6): 866-9) |
|  |  |  | Matrilin 2 involved in peripheral nerve regeneration (Malin et al., J Cell Sci 2009; 122(Pt 7): 995-1004) |
| VWA1 | 2.49 | von Willebrand factor A domain containing 1 | Belongs to von Willebrand factor A (VWFA) domain superfamily of ECM proteins and appears to play a role in cartilage structure and function |
|  |  |  | Associated with fracture healing (Yuan and Cai, Mol Med Rep 2017; 16(4): 4529-36) |

Summary

Antibodies are an important and a well-established class of drugs. Most recently, research has focused on single chain variable fragments (scFvs) as an alternative for larger whole antibody molecules. Therefore, scFvs have been developed against various targets for different cancers [34-37]. Furthermore, scFvs have been attached onto molecular targeting moieties for development of potential therapeutic and diagnostic applications using MRI and bioluminescence imaging [37-40].

As shown above, anti-ELTD1 pAb treatment has decreased tumor volumes and increased animal survival in both mouse GL261 and human G55 xenograft glioma models [26]. Since pAbs are not currently a viable therapy, the aim of this patent was to create and optimize a monoclonal antibody therapy against ELTD1. The inventors created an anti-ELTD1 mAb and an anti-ELTD1 scFv fragment against the external region of ETLD1. Generation of monoclonal antibodies to ELTD1 was accomplished in a chicken. This choice of host stems from the fact that it is farther removed from human than is rodents and therefore allows the generation of antibodies that are higher affinity and that have the potential of reacting across species.

Regarding treatment responses in mice with GBM, both monoclonal antibodies to ELTD1 (anti-ELTD1 mAb and anti-ELTD1 scFv fragment) were successful in increasing survival and decreasing tumor volumes. Although the anti-ELTD1 scFv fragment treatment appeared to be successful, there was a high amount of variance seen within the tumor volumes and survival post tumor detection within the group.

Both anti-ELTD1 mAb and anti-ELTD1 scFv fragment were successful in normalizing the perfusion levels within the tumor region. Furthermore, both of the anti-ELTD1 treatments were successful in not only decreasing, but also normalizing the microvessel density (MVD) levels within the tumor region. These results show that by targeting ELTD1, it's possible to normalize the tumor-related vasculature within the tumor region. The relationship between ELTD1 and VEGFR2 in GBM was shown hereinabove. Those data showed that treatment of mice bearing GBM tumors with anti-ELTD1 Abs decreased levels of VEGFR2 in the tumor tissues. In the current invention, experiments were performed to shed some light on the relationship between anti-ELTD1 mAb treatment and Notch, another important angiogenic marker [31]. Untreated G55 tumors were found to have increased Notch1 protein expression compared to contralateral normal tissue. However, through repetitive treatments with both anti-ELTD1 mAb and anti-ELTD1 scFv fragment, Notch1 protein expression levels decreased within the tumor. Notch1 has been shown to play a major role in promoting angiogenesis as does VEGFR2. Therefore, the finding that anti-ELTD1 Ab therapy increases two distinct molecules that are critical in angiogenesis is an important finding. Indeed, in these experiments, treatment of mice bearing GBM tumors with the anti-VEGF mAb Avastin, decreased VEGFR2 but did not decrease Notch1. The decrease in Notch1 within the tumor may further explain and support the normalization of vasculature in the tumor but is not a limitation of the present invention.

By constructing biotin-albumin-Gd-DTPA molecular probes bound to either non-specific IgG, anti-ELTD1 mAb or anti-ELTD1 scFv fragment, it was possible to localize the antibodies in vivo and to quantify the signal intensity produced by the probes within the tumor region. Through this, the inventors were able to determine that both the monoclonal and fragment anti-ELTD1 attached probes were successful in localizing within the tumor region. Furthermore, the molecular targeting data demonstrated that the anti-ELTD1 scFv fragment attached probe was able to bind to diffuse tumor regions that were once undetectable via MRI. This finding shows that the anti-ELTD1 scFv fragment can be used to localize diffuse tumors and may provide a novel detection tool for identifying the extent of tumor tissue.

Figure 13:
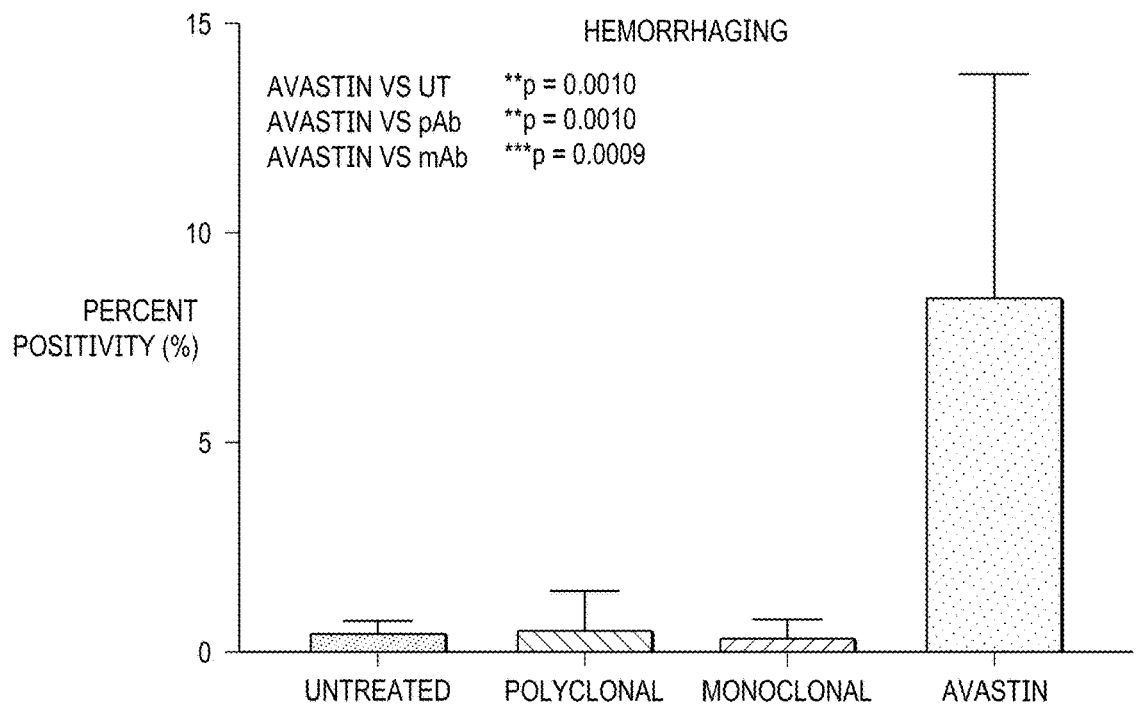
FIG. 13 shows that anti-ELTD1 mAb treatment is associated with less hemorrhaging (measuring percent positivity) than anti-VEGF mAb (Avastin) treatment in G55 gliomas. Histology iron stained tissue sections from G55 tumors for either untreated mice or mice treated with either anti-ELTD1 pAb, anti-ELTD1 mAb, or Avastin. Note the high levels of hemorrhaging (increased levels of iron staining) for the Avastin treated mice. There was a significant increase in hemorrhaging in tissues from the Avastin-treated mice compared to other groups ($p<0.01$ for all).

By staining for iron of hemoglobin in red blood cells it was also possible to assess the effect of hemorrhaging associated with antibody therapies against VEGF (Avastin) compared to anti-ELTD1 pAb or mAb treatments in G55 human GBM xenograft tissue section (FIG. 13). Given that one of the most serious and life-threatening adverse events of Avastin therapy in cancer is hemorrhage, it was important to know if anti-ELTD1 Ab therapies also caused hemorrhage. In the current invention, anti-ELTD1 Ab therapies did not show hemorrhage while Avastin therapy did.

Figure 14:
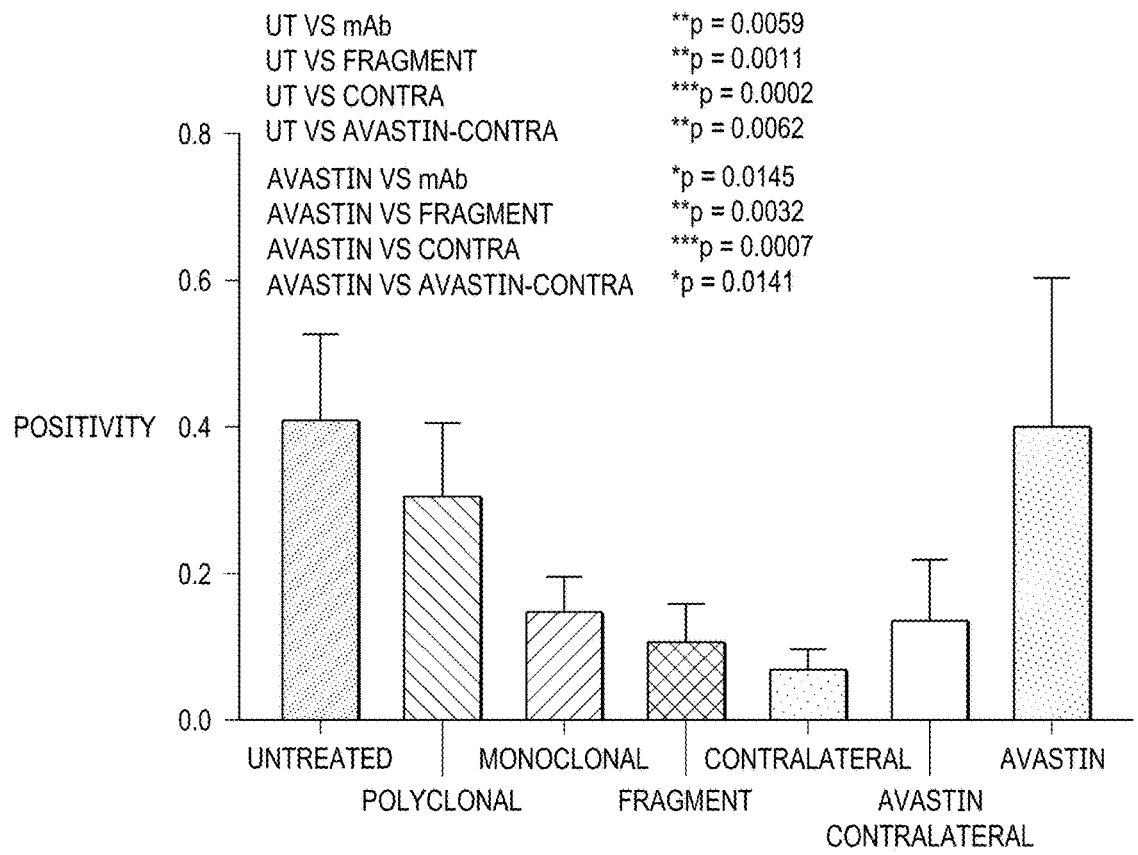
FIG. 14 shows that anti-ELTD1 mAb and scFv fragment treatments have less Notch levels (measuring percent positivity) than anti-VEGF mAb (Avastin) treatment in G55 gliomas. Notch stained tissue sections from G55 tumors for either untreated mice or mice treated with either anti-ELTD1 pAb, anti-ELTD1 mAb, anti-ELTD1 scFv fragment or Avastin. Note the high levels of Notch for the Avastin treated mice. Contralateral tissues from untreated (Contralateral) or Avastin-treated (Avastin Contralateral) mice were included for comparisons. There was a significant increase in Notch levels for the Avastin-treated tissues compared to the other groups ($p<0.05$ for all). Untreated (UT) Notch levels were also significantly higher compared to other groups ($p<0.01$ for all).

Anti-ELTD1 was found to significantly decrease Notch protein levels, which were high in untreated G55 tumors, and shown to not be affected by anti-VEGF (Avastin) treatment, i.e. anti-ELTD1 treatment (pAb, mAb or scFv fragment of mAb) were found to significantly decrease Notch, whereas Avastin-treatment had no effect (FIG. 14).

In conclusion, these molecular targeting data demonstrate the diagnostic use of the anti-ELTD1 mAb and the anti-ELTD1 scFv fragment for distinguishing diffuse tumors that are undetectable through MR imaging. Furthermore, both of the anti-ETLD1 treatments were successful in increasing survival, decreasing tumor volumes, and normalizing tumor associated vasculature. Although ELTD1 was shown to be downregulated through the Notch/DLL4 pathways in normal vasculature, this study shows the relationship between ELTD1 and Notch1 in GBM tumors. It was also shown that anti-ELTD1 mAb or anti-ELTD1 scFv fragment treatments did not result in hemorrhaging, as is commonly associated with Avastin treatment. This example demonstrated that both the monoclonal and scFv antibody therapy against ELTD1 were effective and can be used for anti-angiogenic therapy(ies) against GBM tumors.

Example 4. A New Biomarker Target, ELTD1, for Multiple Sclerosis: Molecular-Targeted MRI Detection of ELTD1 in a Mouse Experimental Autoimmune Encephalomyelitis (EAE) Model Multiple sclerosis, or MS, is an autoimmune disease that affects the ability of the nervous system to carry signals to and from the brain. Inflammation causes damage to myelin, the protective covering that surrounds nerve cells, slowing and sometimes blocking nerve impulses. The disease carries with it a variety of symptoms, including problems with vision, tremors, paralysis, painful spasms, imbalance, and cognitive changes. In glioblastomas (GBM), the inventors detected over-expression of ELTD1 (epidermal growth factor, latrophilin, and 7 transmembrane domain containing protein 1 on chromosome 1) and found that Abs targeting ELTD1 could increase animal survival and decrease tumor volumes. From RNA-seq analysis of tumor tissues from anti-ELTD1 treated animals, we discovered that some of the genes affected by anti-ELTD1 antibody are also associated with MS. Molecular-targeted MR imaging of ELTD1 was used to assess ELTD1 levels in a mouse model for MS (EAE, or experimental autoimmune encephalomyelitis).

In vivo ELTD1 levels were assessed using molecular-targeted MRI (mtMRI) via coupling anti-ELTD1 Abs with a gadolinium (Gd)-based MRI contrast agent. Experimental autoimmune encephalomyelitis (EAE) mice (2-3 months old; female; n=10; Anti-ELTD1-albumin-Gd-DTPA-biotin (anti-ELTD1-probe) (n=5 with anti-ELTD1 probe; n=5 with a non-specific IgG contrast agent), were anesthetized with isoflurane (2-3%) for MRI scans. The targeted contrast agent probe for ELTD1 (20 µg) was used to obtain ELTD1 expression images. MRI experiments were done on a Bruker Biospec 7.0 Tesla/30 cm horizontal-bore imaging system. Multiple brain region 1H MR image slices were taken using a spin echo multislice (repetition time (TR) 0.8 s, echo time (TE) 23 ms, 128×128 matrix, 4 steps per acquisition, 3×4 cm2 field of view, 1 mm slice thickness). Rat brains were imaged at 0 (pre-contrast) and at 20 min. intervals up to 90 min. post-contrast agent injection. T1-weighted images were obtained using a variable TR (repetition time) spin-echo sequence. Pixel-by-pixel relaxation maps were reconstructed from a series of T1-weighted images using a non-linear two-parameter fitting procedure. The T1 value of a specified region-of-interest (ROI) was computed from all the pixels in the identified ROIs.

Figure 15A:
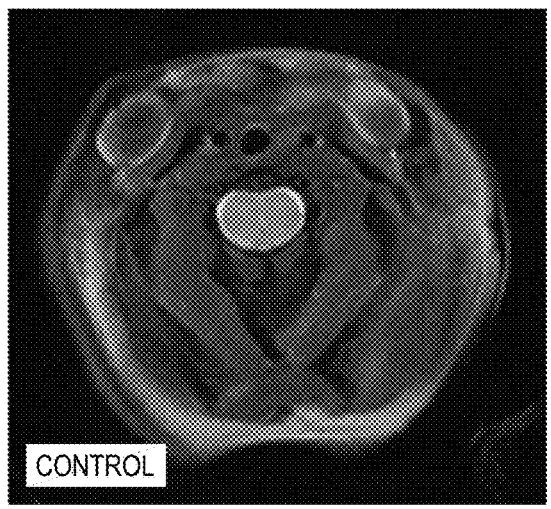
FIGS. 15A to 15C show T2 MRI scans demonstrating changes in the cervical spinal cord of Experimental autoimmune encephalomyelitis (EAE) mice at day 27 following disease progression versus a control animal.
Figure 15B:
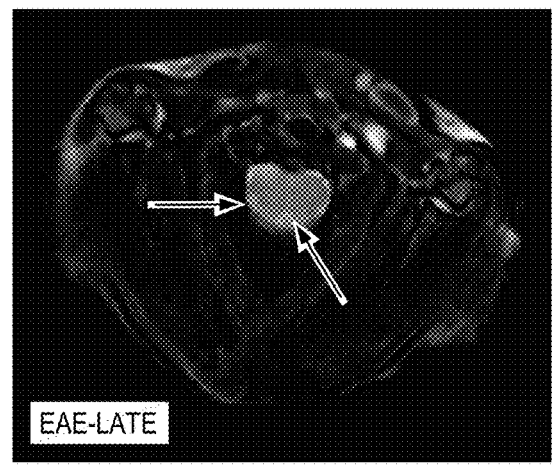
Figure 15C:
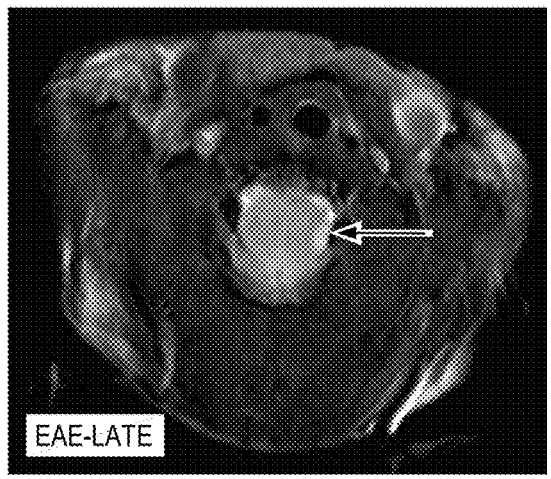

FIGS. 15A to 15C show T2 MRI scans demonstrating changes in the cervical spinal cord of EAE mice at day 27 following disease progression versus a control.

Figure 16C:
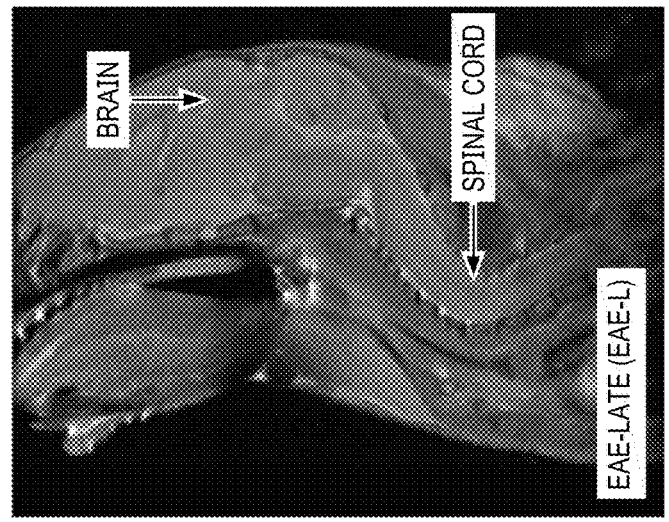
FIGS. 16A to 16C show contrast images obtained using a Gd-DTPA MRI contrast agent and T1-weighted MRI scans taken early at day 10 (EAE-E) and late at day 26 (EAE-L) following disease progression versus a control animal.
Figure 16B:
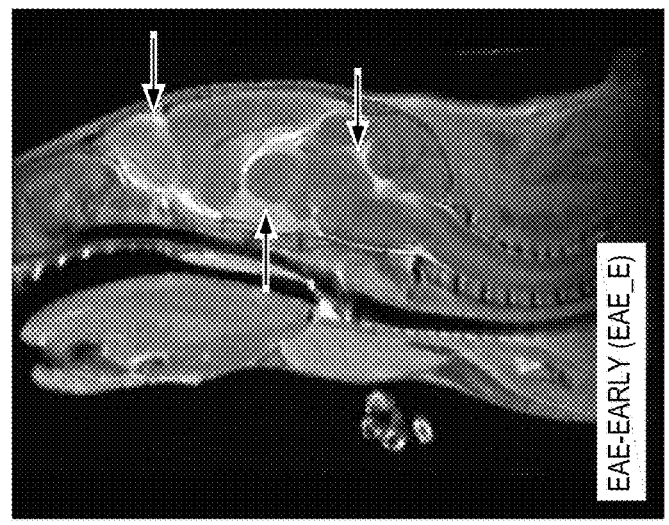
Figure 16A:
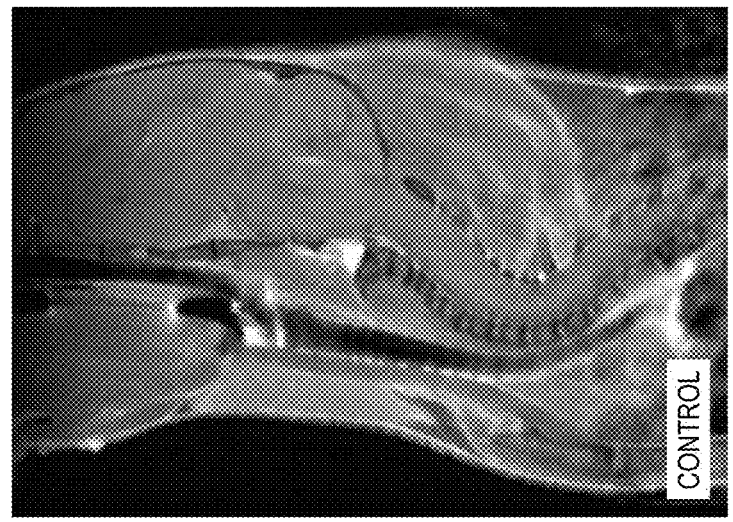

FIGS. 16A to 16C show contrast images obtained using a Gd-DTPA MRI contrast agent and T1-weighted MRI scans taken at day 10 (EAE-E) and day 26 (EAE-L) following disease progression.

Figure 17:
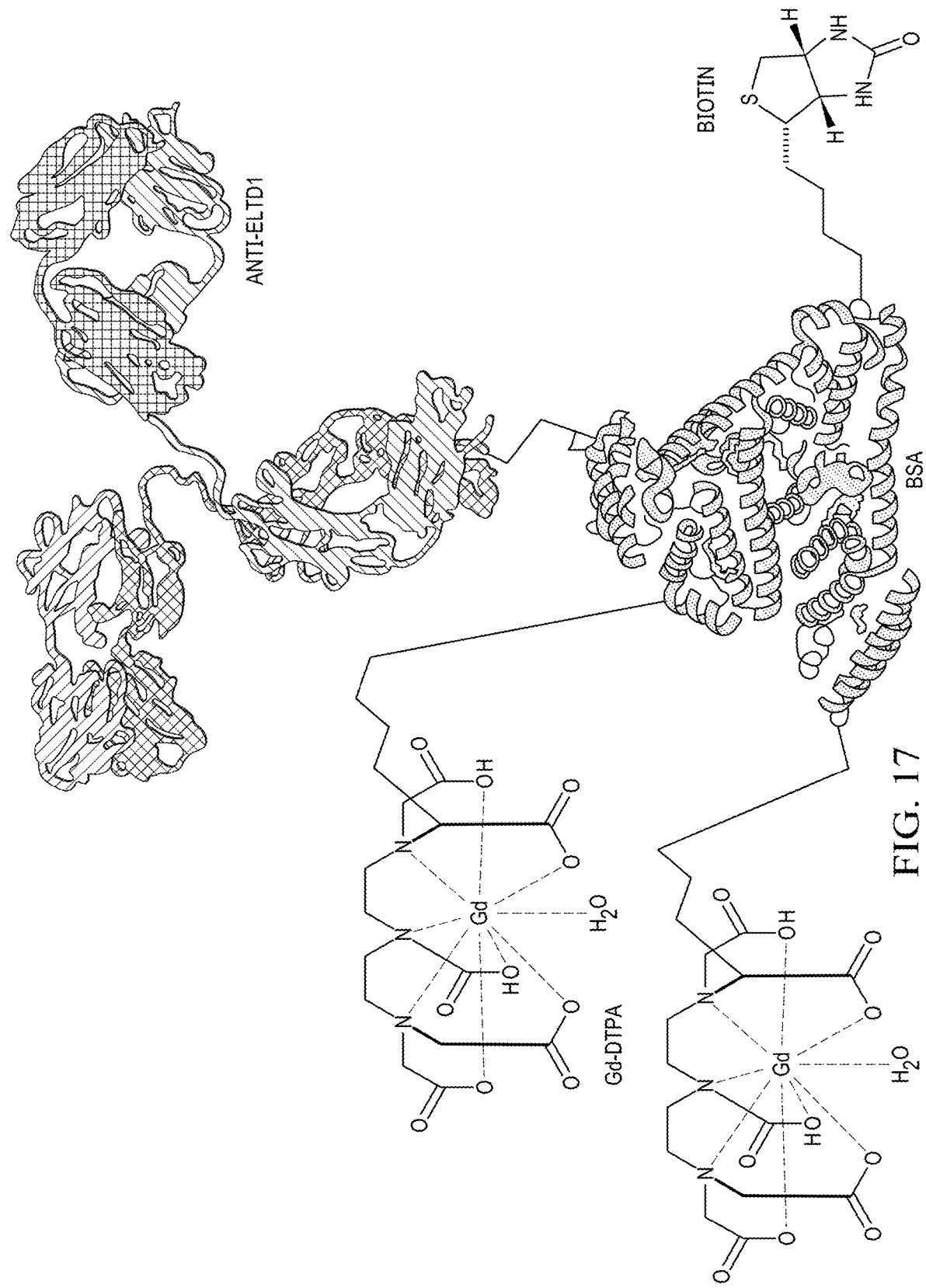
FIG. 17 shows the anti-ELTD1 mAb probe. A monoclonal antibody (mAb) against the extracellular domain of ELTD1 was conjugated to albumin which had Gd-DTPA and biotin attached to the construct.

FIG. 17 shows the anti-ELTD1 mAb probe. A monoclonal antibody (mAb) against the extracellular domain of ELTD1 was conjugated to albumin which had Gd-DTPA and biotin attached to the construct.

Figure 18B:
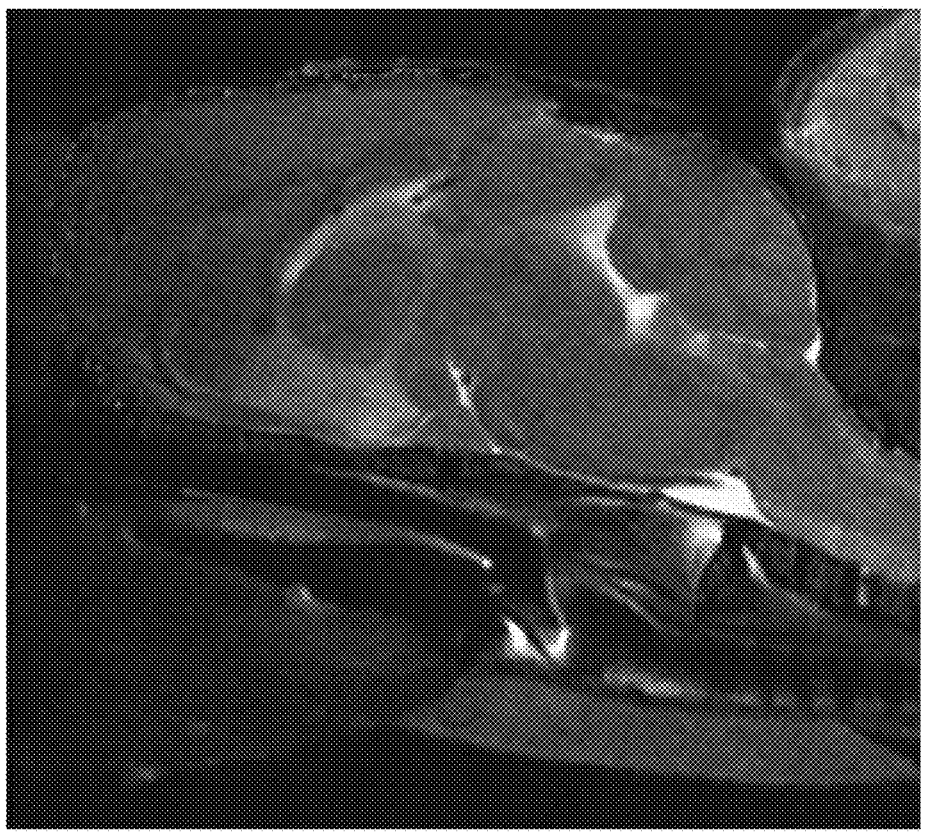
FIGS. 18A to 18C show mAb anti-ELTD1 MRI probe efficiently binds to various brain regions in an EAE mouse model for Multiple Sclerosis (MS), compared to non-selective control MRI contrast agent. $p<0.0001$ when comparing anti-ELTD1 probe vs. control IgG contrast agent % change in T1 relaxation rates.
Figure 18A:
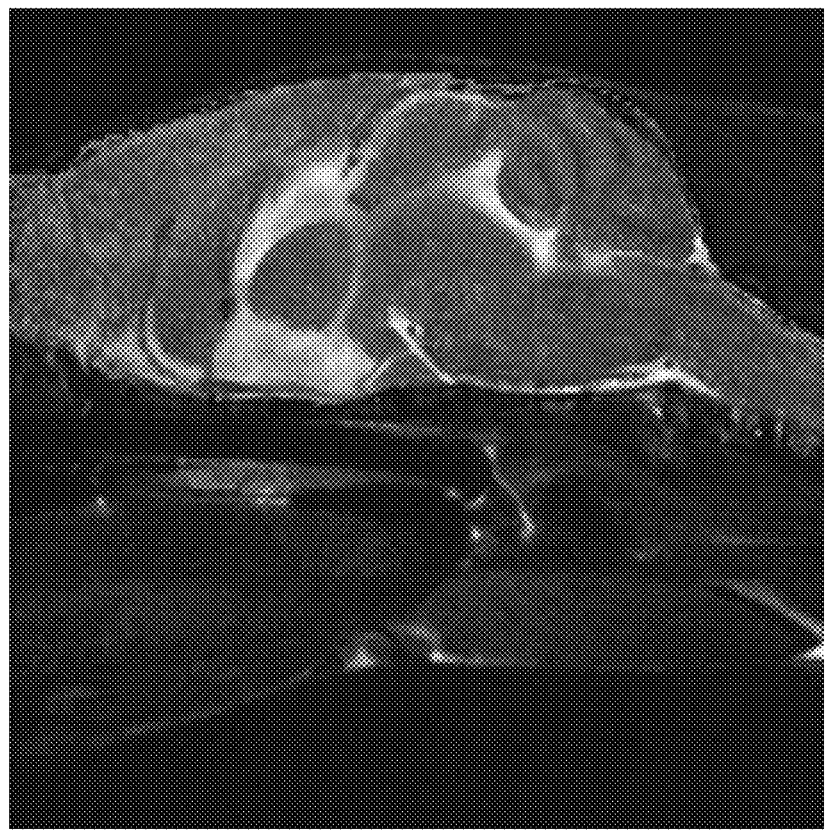
Figure 18C:
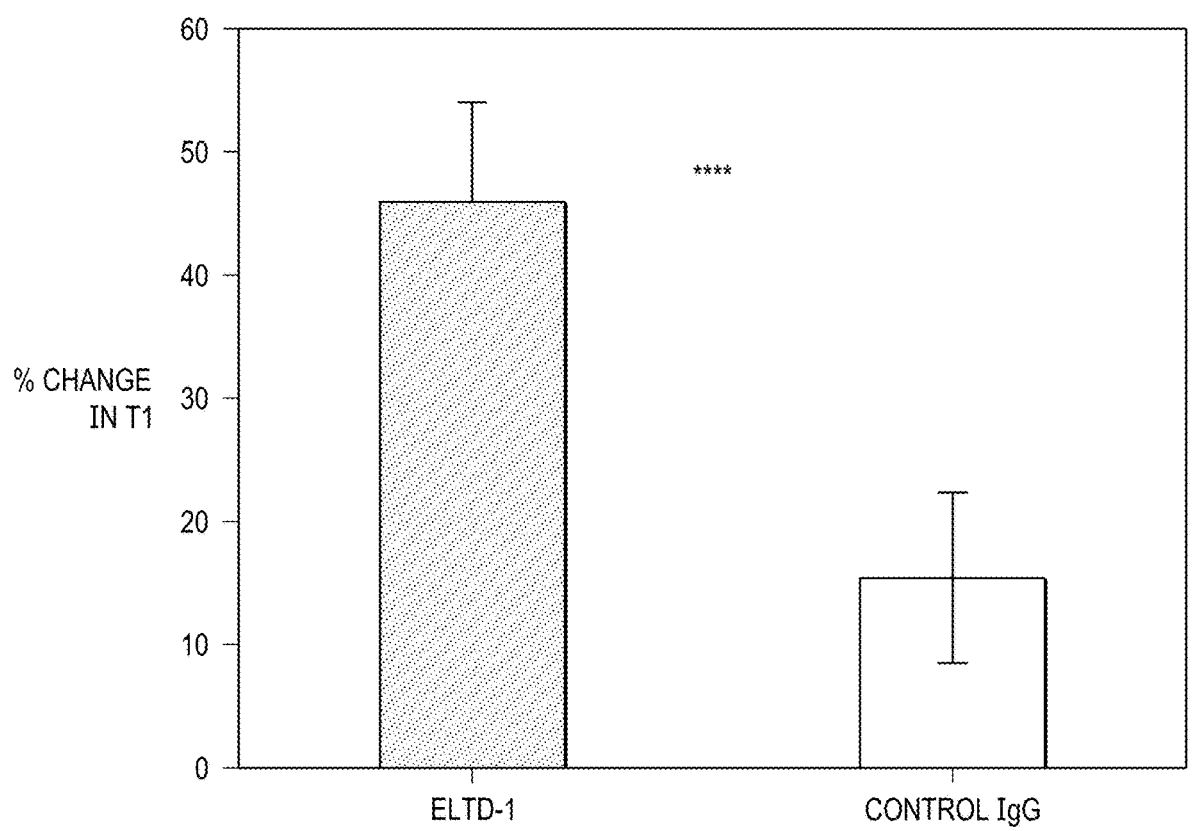

FIGS. 18A to 18C show anti-ELTD1 mAb MRI probe efficiently binds to various brain regions in an EAE mouse model for MS, compared to non-selective control MRI contrast agent. $p<0.0001$ when comparing anti-ELTD1 probe vs. control IgG contrast agent % change in T1 relaxation rates.

Figure 19A:
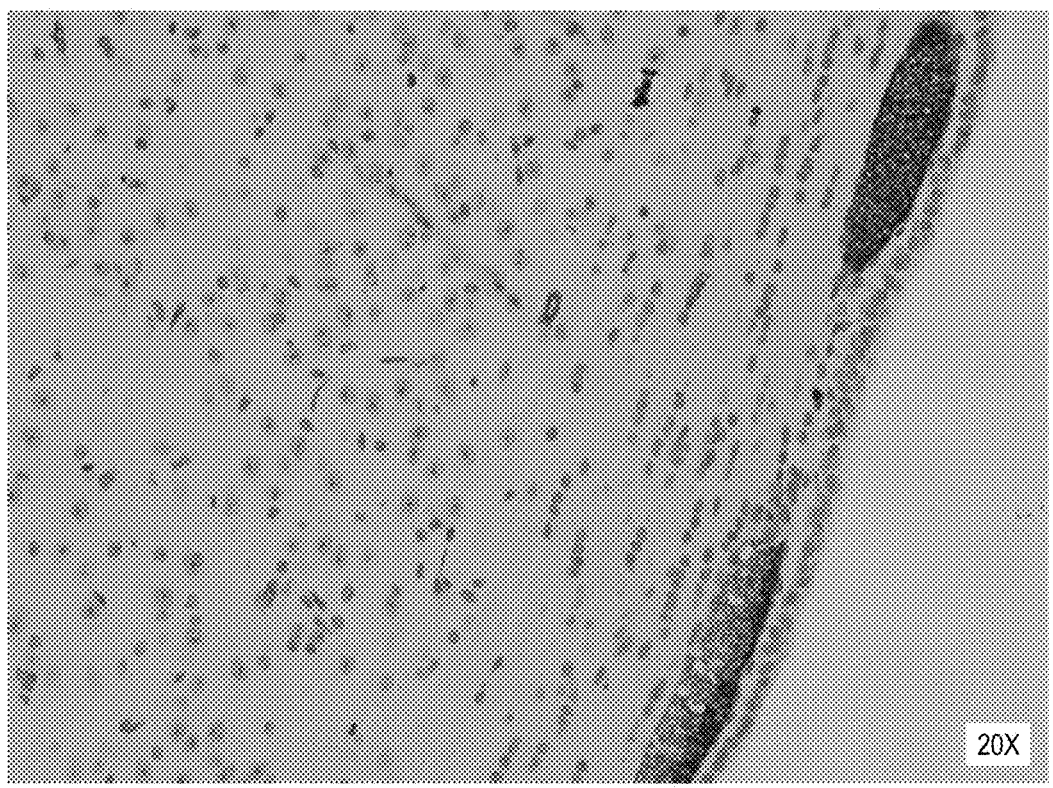
FIGS. 19A and 19B show (FIG. 19A) mAb anti-ELTD1 MRI probe efficiently binds to endothelial cells in the brain of an EAE mouse model for MS. Molecular-targeted MR imaging for ELTD1 (streptavidin-HRP (horse radish peroxidase) binds to biotin moiety of anti-ELTD1 probe).
Figure 19B:
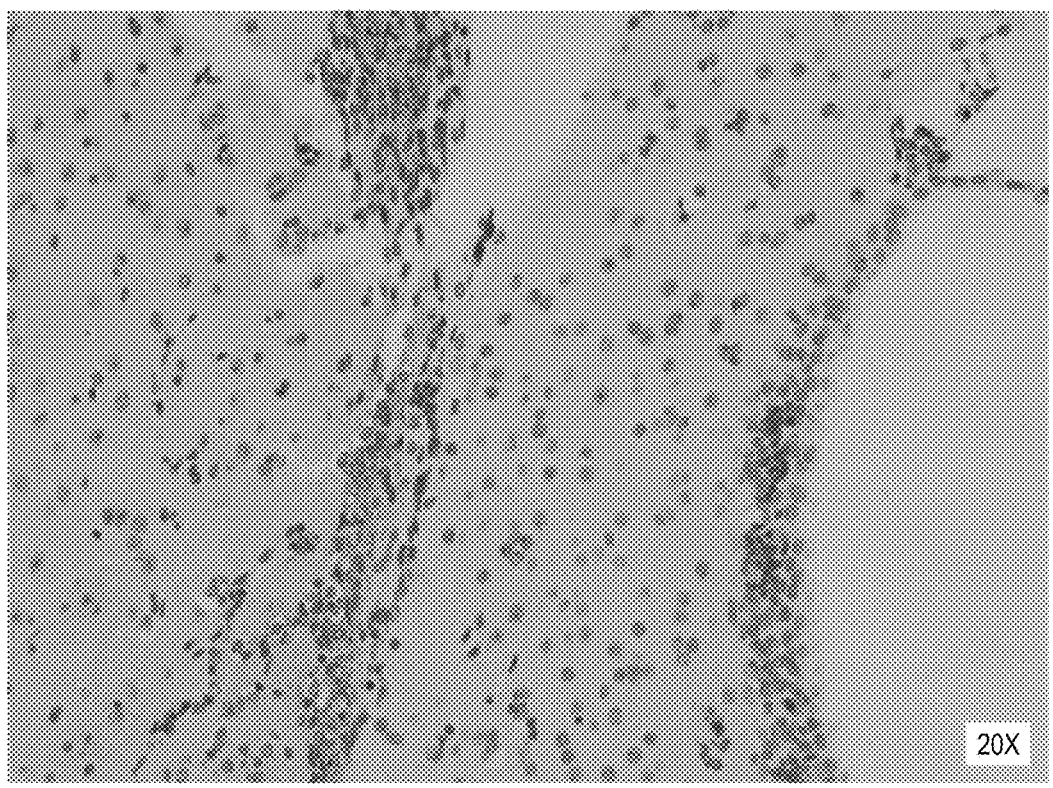

FIGS. 19A and 19B show: (FIG. 19A) anti-ELTD1 mAb MRI probe efficiently binds to endothelial cells in the brain of an EAE mouse model for MS. Molecular-targeted MR imaging for ELTD1 (strep-avidin-HRP (horse radish peroxidase) binds to biotin moiety of anti-ELTD1 probe). (FIG. 19B) Immunohistochemistry staining for ELTD1 indicates high levels in endothelial cells of EAE mouse.

Thus, using mtMRI the inventors were able to demonstrate significantly increased ELTD1 levels in EAE mice (model for MS) administered the anti-ELTD1 mAb probe, compared to EAE mice administered a non-specific IgG contrast agent. The data in FIGS. 15A to 15C demonstrate the use of the present invention for in vivo mtMR imaging for ELTD1 levels in an EAE mouse model for MS. mtMRI shows for the first time non-invasive in vivo detection of ELTD1 in a mouse model for MS.

Table 5: RNA sequencing data showing that of the 23 genes altered by anti-ELTD-1 mAb therapy in a GBM model, 7 are similarly associated with MS.

TABLE 5 mAb Anti-ELTD1 Therapy Gene-Fold Changes: Down-regulated >2-fold Multiple Sclerosis

| Gene | >2-fold decrease | Protein | Description |
|---|---|---|---|
| SCN5A | −5.11 | Sodium channel protein type 5 subunit alpha | Protein mediates the voltage-dependent sodium ion permeability of excitable membranes<br>SCN5A encodes several sodium channels including Nav1.5. NaV1.5 is upregulated in EAE (experimental autoimmune encephalomyelitis) mouse model (Pappalardo et al., Neuroreport 2014; 25: 1208-15) |
| ADA | −4.53 | Adenosine deaminase | Catalyzes the hydrolytic deamination of adenosine and 2-deoxyadenosine<br>Elevated adenosine deaminase in CSF of MS patients (Samuraki et al., Mult Scler Relat Disord 2017; 13: 44-46) |
| APLN | −2.81 | apelin | Gene encodes a peptide that functions as an endogenous ligand for the G protein coupled receptor APJ<br>Serum apelin-13 levels are elevated in MS patients (Alpua et al., Ann Indian Acad Neurol 2018; 21: 126) |
| SPNS2 | −2.74 | spinster homolog 2 | SPNS2 has 2,740 functional associations with biological entities spanning 8 categories<br>SPNS2 knock-out mice are protected against EAE (Donoviel et al., FASEB J 2015; 29: 5018-28) |
| BMP2 | −2.71 | bone morphogenetic protein 2 | Gene encodes a secreted ligand of the TGF-beta (transforming growth factor-beta) superfamily of proteins<br>High serum levels of BMP-2 related to failure of remyelination and neuro-regeneration in relapsing remitting MS patients (Pen et al., J Neuroimmunol 2017; 310: 120-128) |

TABLE 6 mAb Anti-ELTD1 Therapy Gene-Fold Changes: Upregulated >2-fold Multiple Sclerosis

| Gene | >2-fold increase | Protein | Description |
|---|---|---|---|
| CD74 | 3.45 | CD74 molecule, major histocompatibility complex, class II invariant chain | Associates with class II major histocompatibility complex (MHC) and is an important chaperone that regulates antigen presentation for immune response. Also serves as cell surface receptor for cytokine macrophage migration inhibitory factor (MIF) which, when bound to the encoded protein, initiates survival pathways and cell proliferation.<br>MIF receptor CD74 is downregulated in B cells from early onset MS patients (Rijvers et al., Eur J Immunol 2018; 48(11): 1861-71) |
| IKZF1 | 2.63 | IKAROS family zinc finger 1 (Ikaros) | Gene encodes a transcription factor that belongs to the family of zinc-finger DNA-binding proteins associated with chromatin remodeling. The expression of this protein is restricted to the fetal and adult hemo-lymphopoietic system, and it functions as a regulator of lymphocyte differentiation.<br>IKZF1 plays a central regulatory role in controlling gene expression in the pathogenesis of MS (Liu et al., Mol Biol Rep 2013; 40: 3731-7) |

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited features, elements, components, groups, integers, and/or steps, but do not exclude the presence of other unstated features, elements, components, groups, integers and/or steps. In embodiments of any of the compositions and methods provided herein, "comprising" may be replaced with "consisting essentially of" or "consisting of". As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only. As used herein, the phrase "consisting essentially of" requires the specified features, elements, components, groups, integers, and/or steps, but do not exclude the presence of other unstated features, elements, components, groups, integers and/or steps as well as those that do not materially affect the basic and novel characteristic(s) and/or function of the claimed invention.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES—EXAMPLE 2

1. Dolecek T A, Propp J M, Stroup N E, Kruchko C. CBTRUS statistical report: primary brain and central nervous system tumors diagnosed in the United States in 2005-2009. Neuro Oncol. 2012; 14 Suppl 5: v1-49.
2. Tamimi A F, Juweid M. Epidemiology and Outcome of Glioblastoma. In: De Vleeschouwer S, editor. Glioblastoma. Brisbane (AU), 2017.
3. Alves T R, Lima F R, Kahn S A, Lobo D, Dubois L G, Soletti R, Borges H, Neto V M. Glioblastoma cells: a heterogeneous and fatal tumor interacting with the parenchyma. Life Sci. 2011; 89: 532-9.
4. Beal K, Abrey L E, Gutin P H. Antiangiogenic agents in the treatment of recurrent or newly diagnosed glioblastoma: analysis of single-agent and combined modality approaches. Radiat Oncol. 2011; 6: 2.
5. Ghiaseddin A, Peters K B. Use of bevacizumab in recurrent glioblastoma. CNS Oncol. 2015; 4: 157-69.

6. Thakkar J P, Dolecek T A, Horbinski C, Ostrom Q T, Lightner D D, Barnholtz-Sloan J S, Villano J L. Epidemiologic and molecular prognostic review of glioblastoma. Cancer Epidemiol Biomarkers Prev. 2014; 23: 1985-96.
7. Fumari F B, Fenton T, Bachoo R M, Mukasa A, Stommel J M, Stegh A, Hahn W C, Ligon K L, Louis D N, Brennan C, Chin L, DePinho R A, Cavenee W K. Malignant astrocytic glioma: genetics, biology, and paths to treatment. Genes Dev. 2007; 21: 2683-710.
8. Suhardja A, Hoffman H. Role of growth factors and their receptors in proliferation of microvascular endothelial cells. Microsc Res Tech. 2003; 60: 70-5.
9. Olar A, Aldape K D. Using the molecular classification of glioblastoma to inform personalized treatment. J Pathol. 2014; 232: 165-77.
10. Genentech I. Avastin Prescribing Information. 2018.
11. Nechiporuk T, Umess L D, Keating M T. ETL, a novel seven-transmembrane receptor that is developmentally regulated in the heart. ETL is a member of the secretin family and belongs to the epidermal growth factor-seven-transmembrane subfamily. J Biol Chem. 2001; 276: 4150-7.
12. Masiero M, Simoes F C, Han H D, Snell C, Peterkin T, Bridges E, Mangala L S, Wu S Y, Pradeep S, Li D, Han C, Dalton H, Lopez-Berestein G, Tuynman J B, Mortensen N, Li J L, Patient R, Sood A K, Banham A H, Harris A L, Buffa F M. A core human primary tumor angiogenesis signature identifies the endothelial orphan receptor ELTD1 as a key regulator of angiogenesis. Cancer Cell. 2013; 24: 229-41.
13. Ziegler J, Zalles M, Smith N, Saunders D, Lerner M, Fung K M, Patel M, Wren J D, Lupu F, Battiste J, Towner R A. Targeting ELTD1, an angiogenesis marker for glioblastoma (GBM), also affects VEGFR2: molecular-targeted MRI assessment. Am J Nucl Med Mol Imaging. 2019; 9: 93-109.
14. Dieterich L C, Mellberg S, Langenkamp E, Zhang L, Zieba A, Salomaki H, Teichert M, Huang H, Edqvist P H, Kraus T, Augustin H G, Olofsson T, Larsson E, Soderberg O, Molema G, Ponten F, Georgii-Hemming P, Alafuzoff I, Dimberg A. Transcriptional profiling of human glioblastoma vessels indicates a key role of VEGF-A and TGFbeta2 in vascular abnormalization. J Pathol. 2012; 228: 378-90.
15. Ziegler J, Pody R, Coutinho de Souza P, Evans B, Saunders D, Smith N, Mallory S, Njoku C, Dong Y, Chen H, Dong J, Lerner M, Mian O, Tummala S, Battiste J, Fung K M, Wren J D, Towner R A. ELTD1, an effective anti-angiogenic target for gliomas: preclinical assessment in mouse GL261 and human G55 xenograft glioma models. Neuro Oncol. 2017; 19: 175-85.
16. Buss N A, Henderson S J, McFarlane M, Shenton J M, de Haan L. Monoclonal antibody therapeutics: history and future. Curr Opin Pharmacol. 2012; 12: 615-22.
17. Reichert J M, Rosensweig C J, Faden L B, Dewitz M C. Monoclonal antibody successes in the clinic. Nat Biotechnol. 2005; 23: 1073-8.
18. Lee Y, Kim H, Chung J. An antibody reactive to the Gly63-Lys68 epitope of N T-proBNP exhibits O-glycosylation-independent binding. Exp Mol Med. 2014; 46: e114.
19. Boussif O, Lezoualc'h F, Zanta M A, Mergny M D, Scherman D, Demeneix B, Behr J P. A versatile vector for gene and oligonucleotide transfer into cells in culture and in vivo: polyethylenimine. Proc Natl Acad Sci USA. 1995; 92: 7297-301.
20. Andris-Widhopf J, Rader C, Steinberger P, Fuller R, Barbas C F, 3rd. Methods for the generation of chicken monoclonal antibody fragments by phage display. J Immunol Methods. 2000; 242: 159-81.
21. Barbas C F. Phage Display: A Laboratory Manual. Cold Spring Harbor Laboratory Press: Cold Spring Harbor, NY; 2001.
22. Han J, Lee J H, Park S, Yoon S, Yoon A, Hwang D B, Lee H K, Kim M S, Lee Y, Yang W J, Youn H D, Kim H, Chung J. A phosphorylation pattern-recognizing antibody specifically reacts to RNA polymerase II bound to exons. Exp Mol Med. 2016; 48: e271.
23. Zhu W, Kato Y, Artemov D. Heterogeneity of tumor vasculature and antiangiogenic intervention: insights from M R angiography and DCE-MRI. PLoS One. 2014; 9: e86583.
24. Towner R A, Smith N, Doblas S, Garteiser P, Watanabe Y, He T, Saunders D, Herlea O, Silasi-Mansat R, Lupu F. In vivo detection of inducible nitric oxide synthase in rodent gliomas. Free Radic Biol Med. 2010; 48: 691-703.
25. Dafni H, Landsman L, Schechter B, Kohen F, Neeman M. MRI and fluorescence microscopy of the acute vascular response to VEGF165: vasodilation, hyperpermeability and lymphatic uptake, followed by rapid inactivation of the growth factor. NMR Biomed. 2002; 15: 120-31.
26. Hermanson G. Bioconjugate techniques: New York: Academic Press; 1996.
27. Haacke E. Magnetic resonance imaging: physical principles and sequence design.: New York: Wiley-Liss; 1999.
28. Ewels P, Magnusson M, Lundin S, Kaller M. MultiQC: summarize analysis results for multiple tools and samples in a single report. Bioinformatics. 2016; 32: 3047-8.
29. Torre D, Lachmann A, Ma'ayan A. BioJupies: Automated Generation of Interactive Notebooks for RNA-Seq Data Analysis in the Cloud. Cell Syst. 2018; 7: 556-61 e3.
30. Love M I, Huber W, Anders S. Moderated estimation of fold change and dispersion for RNA-seq data with DESeq2. Genome Biol. 2014; 15: 550.
31. Chen E Y, Tan C M, Kou Y, Duan Q, Wang Z, Meirelles G V, Clark N R, Ma'ayan A. Enrichr: interactive and collaborative HTML5 gene list enrichment analysis tool. BMC Bioinformatics. 2013; 14: 128.
32. Serban F, Daianu O, Tataranu L G, Artene S A, Emami G, Georgescu A M, Alexandru O, Purcaru S O, Tache D E, Danciulescu M M, Sfredel V, Dricu A. Silencing of epidermal growth factor, latrophilin and seven transmembrane domain-containing protein 1 (ELTD1) via siRNA-induced cell death in glioblastoma. J Immunoassay Immunochem. 2017; 38: 21-33.
33. Zou Q, Xiao Z, Huang R, Wang X, Wang X, Zhao H, Yang X. Survey of the translation shifts in hepatocellular carcinoma with ribosome profiling. Theranostics. 2019; 9: 4141-55.
34. Zhao C, qin Q, Wang Q, Zhang J, Xu Y, Li W, Gu M, Chen S, Deng A. SCUBE3 overexpression predicts poor prognosis in non-small cell lung cancer. Biosci Trends. 2013; 7: 264-9.
35. Zhang Y, Hua S, Zhang A, Kong X, Jiang C, Deng D, Wenlong B. Association between polymorphisms in COMT, PLCH1, and CYP17A1, and non-small-cell lung cancer risk in Chinese nonsmokers. Clin Lung Cancer. 2013; 14: 45-9.
36. Chang P M, Yeh Y C, Chen T C, Wu Y C, Lu P J, Cheng H C, Lu H J, Chen M H, Chou T Y, Huang C Y. High expression of CHRNA1 is associated with reduced survival in early stage lung adenocarcinoma after complete resection. Ann Surg Oncol. 2013; 20: 3648-54.
37. Zhuo H, Zhao Y, Cheng X, Xu M, Wang L, Lin L, Lyu Z, Hong X, Cai J. Tumor endothelial cell-derived cadherin-2 promotes angiogenesis and has prognostic significance for lung adenocarcinoma. Mol Cancer. 2019; 18: 34.
38. Varley K E, Gertz J, Roberts B S, Davis N S, Bowling K M, Kirby M K, Nesmith A S, Oliver P G, Grizzle W E, Forero A, Buchsbaum D J, LoBuglio A F, Myers R M. Recurrent read-through fusion transcripts in breast cancer. Breast Cancer Res Treat. 2014; 146: 287-97.
39. Cai Y, Li W F, Sun Y, Liu K. Downregulation of microRNA-645 suppresses breast cancer cell metastasis via targeting DCDC2. Eur Rev Med Pharmacol Sci. 2017; 21: 4129-36.
40. Yuan J, Zhang N, Zhu H, Liu J, Xing H, Ma F, Yang M. CHST9 rs1436904 genetic variant contributes to prognosis of triple-negative breast cancer. Sci Rep. 2017; 7: 11802.
41. Lee J W, Guan W, Han S, Hong D K, Kim L S, Kim H. MicroRNA-708-3p mediates metastasis and chemoresistance through inhibition of epithelial-to-mesenchymal transition in breast cancer. Cancer Sci. 2018; 109: 1404-13.
42. Wren J D. A global meta-analysis of microarray expression data to predict unknown gene functions and estimate the literature-data divide. Bioinformatics. 2009; 25: 1694-701.
43. Towner R A, Jensen R L, Colman H, Vaillant B, Smith N, Casteel R, Saunders D, Gillespie D L, Silasi-Mansat R, Lupu F, Giles C B, Wren J D. ELTD1, a potential new biomarker for gliomas. Neurosurgery. 2013; 72: 77-90; discussion 1.
44. Dai S, Wang X, Li X, Cao Y. MicroRNA-139-5p acts as a tumor suppressor by targeting ELTD1 and regulating cell cycle in glioblastoma multiforme. Biochem Biophys Res Commun. 2015; 467: 204-10.
45. Huang J, He Y, Chen M, Du J, Li G, Li S, Liu W, Long X. Adenosine deaminase and adenosine kinase expression in human glioma and their correlation with glioma associated epilepsy. Mol Med Rep. 2015; 12: 6509-16.
46. Yang X, Li D, Cheng S, Fan K, Sheng L, Zhang J, Feng B, Xu Z. The correlation of bone morphogenetic protein 2 with poor prognosis in glioma patients. Tumour Biol. 2014; 35: 11091-5.
47. Guo M, Jiang Z, Zhang X, Lu D, Ha A D, Sun J, Du W, Wu Z, Hu L, Khadarian K, Shen J, Lin Z. miR-656 inhibits glioma tumorigenesis through repression of BMPR1A. Carcinogenesis. 2014; 35: 1698-706.
48. Xing D, Wang J, Ou S, Wang Y, Qiu B, Ding D, Guo F, Gao Q. Expression of neonatal Nav1.5 in human brain astrocytoma and its effect on proliferation, invasion and apoptosis of astrocytoma cells. Oncol Rep. 2014; 31: 2692-700.
49. Zeng J, Wu Y, Zhuang S, Qin L, Hua S, Mungur R, Pan J, Zhu Y, Zhan R. Identification of the role of TRPM8 in glioblastoma and its effect on proliferation, apoptosis and invasion of the U251 human glioblastoma cell line. Oncol Rep. 2019.
50. Iwadate Y, Matsutani T, Hirono S, Shinozaki N, Saeki N. Transforming growth factor-beta and stem cell markers are highly expressed around necrotic areas in glioblastoma. J Neurooncol. 2016; 129: 101-7.
51. Brescia P, Ortensi B, Fornasari L, Levi D, Broggi G, Pelicci G. CD133 is essential for glioblastoma stem cell maintenance. Stem Cells. 2013; 31: 857-69.
52. Izumoto S, Ohnishi T, Arita N, Hiraga S, Taki T, Hayakawa T. Gene expression of neural cell adhesion molecule L1 in malignant gliomas and biological significance of L1 in glioma invasion. Cancer Res. 1996; 56: 1440-4.
53. Kiefel H, Bondong S, Hazin J, Ridinger J, Schirmer U, Riedle S, Altevogt P. L1CAM: a major driver for tumor cell invasion and motility. Cell Adh Migr. 2012; 6: 374-84.
54. Bao S, Wu Q, Li Z, Sathornsumetee S, Wang H, McLendon R E, Hjelmeland A B, Rich J N. Targeting cancer stem cells through L1CAM suppresses glioma growth. Cancer Res. 2008; 68: 6043-8.
55. Jin X, Jin X, Jung J E, Beck S, Kim H. Cell surface Nestin is a biomarker for glioma stem cells. Biochem Biophys Res Commun. 2013; 433: 496-501.
56. Wang J, Sakariassen P O, Tsinkalovsky O, Immervoll H, Boe S O, Svendsen A, Prestegarden L, Rosland G, Thorsen F, Stuhr L, Molven A, Bjerkvig R, Enger P O. CD133 negative glioma cells form tumors in nude rats and give rise to CD133 positive cells. Int J Cancer. 2008; 122: 761-8.
57. Ishiwata T, Teduka K, Yamamoto T, Kawahara K, Matsuda Y, Naito Z. Neuroepithelial stem cell marker nestin regulates the migration, invasion and growth of human gliomas. Oncol Rep. 2011; 26: 91-9.
58. Matsuda Y, Naito Z, Kawahara K, Nakazawa N, Korc M, Ishiwata T. Nestin is a novel target for suppressing pancreatic cancer cell migration, invasion and metastasis. Cancer Biol Ther. 2011; 11: 512-23.
59. Wei L C, Shi M, Cao R, Chen L W, Chan Y S. Nestin small interfering RNA (siRNA) reduces cell growth in cultured astrocytoma cells. Brain Res. 2008; 1196: 103-12.
60. Wren J D, Bekeredjian R, Stewart J A, Shohet R V, Garner H R. Knowledge discovery by automated identification and ranking of implicit relationships. Bioinformatics. 2004; 20: 389-98.

REFERENCES—EXAMPLE 3

[1] Wen P Y and Kesari S. Malignant gliomas in adults. N Engl J Med 2008; 359: 492-507.
[2] Karpel-Massler G, Schmidt U, Unterberg A and Halatsch M E. Therapeutic inhibition of the epidermal growth factor receptor in high-grade gliomas: where do we stand? Mol Cancer Res 2009; 7: 1000-1012.
[3] Ohgaki H, Dessen P, Jourde B, Horstmann S, Nishikawa T, Di Patre P L, Burkhard C, Schuler D, Probst-Hensch N M, Maiorka P C, Baeza N, Pisani P, Yonekawa Y, Yasargil M G, Lutolf U M and Kleihues P. Genetic pathways to glioblastoma: a population-based study. Cancer Res 2004; 64: 6892-6899.
[4] Farrell C J and Plotkin S R. Genetic causes of brain tumors: neurofibromatosis, tuberous sclerosis, von Hippel-Lindau, and other syndromes. Neurol Clin 2007; 25: 925-946, viii.
[5] Stupp R, Mason W P, van den Bent M J, Weller M, Fisher B, Taphoorn M J, Belanger K, Brandes A A, Marosi C, Bogdahn U, Curschmann J, Janzer R C, Ludwin S K, Gorlia T, Allgeier A, Lacombe D, Cairncross J G, Eisenhauer E, Mirimanoff R O, European Organisation for R, Treatment of Cancer Brain T, Radiotherapy G and National Cancer Institute of Canada Clinical Trials G. Radiotherapy plus concomitant and adjuvant temozolomide for glioblastoma. N Engl J Med 2005; 352: 987-996.

[6] Lee C Y. Strategies of temozolomide in future glioblastoma treatment. Onco Targets Ther 2017; 10: 265-270.

[7] Kitange G J, Carlson B L, Schroeder M A, Grogan P T, Lamont J D, Decker P A, Wu W, James C D and Sarkaria J N. Induction of MGMT expression is associated with temozolomide resistance in glioblastoma xenografts. Neuro Oncol 2009; 11: 281-291.

[8] Friedman H S, Prados M D, Wen P Y, Mikkelsen T, Schiff D, Abrey L E, Yung W K, Paleologos N, Nicholas M K, Jensen R, Vredenburgh J, Huang J, Zheng M and Cloughesy T. Bevacizumab alone and in combination with irinotecan in recurrent glioblastoma. J Clin Oncol 2009; 27: 4733-4740.

[9] Kreisl T N, Kim L, Moore K, Duic P, Royce C, Stroud I, Garren N, Mackey M, Butman J A, Camphausen K, Park J, Albert P S and Fine H A. Phase II trial of single-agent bevacizumab followed by bevacizumab plus irinotecan at tumor progression in recurrent glioblastoma. J Clin Oncol 2009; 27: 740-745.

[10] Chinot O L, Wick W, Mason W, Henriksson R, Saran F, Nishikawa R, Carpentier A F, Hoang-Xuan K, Kavan P, Cernea D, Brandes A A, Hilton M, Abrey L and Cloughesy T. Bevacizumab plus radiotherapy-temozolomide for newly diagnosed glioblastoma. N Engl J Med 2014; 370: 709-722.

[11] Jensen R L, Mumert M L, Gillespie D L, Kinney A Y, Schabel M C and Salzman K L. Preoperative dynamic contrast-enhanced MRI correlates with molecular markers of hypoxia and vascularity in specific areas of intratumoral microenvironment and is predictive of patient outcome. Neuro Oncol 2014; 16: 280-291.

[12] Das S and Marsden P A. Angiogenesis in glioblastoma. N Engl J Med 2013; 369: 1561-1563.

[13] Poellinger L and Lendahl U. Modulating Notch signaling by pathway-intrinsic and pathway-extrinsic mechanisms. Curr Opin Genet Dev 2008; 18: 449-454.

[14] Miller A C, Lyons E L and Herman T G. cis-Inhibition of Notch by endogenous Delta biases the outcome of lateral inhibition. Curr Biol 2009; 19: 1378-1383.

[15] Masiero M, Simoes F C, Han H D, Snell C, Peterkin T, Bridges E, Mangala L S, Wu S Y, Pradeep S, Li D, Han C, Dalton H, Lopez-Berestein G, Tuynman J B, Mortensen N, Li J L, Patient R, Sood A K, Banham A H, Harris A L and Buffa F M. A core human primary tumor angiogenesis signature identifies the endothelial orphan receptor ELTD1 as a key regulator of angiogenesis. Cancer Cell 2013; 24: 229-241.

[16] Nechiporuk T, Umess L D and Keating M T. ETL, a novel seven-transmembrane receptor that is developmentally regulated in the heart. ETL is a member of the secretin family and belongs to the epidermal growth factor-seven-transmembrane subfamily. J Biol Chem 2001; 276: 4150-4157.

[17] Towner R A, Jensen R L, Colman H, Vaillant B, Smith N, Casteel R, Saunders D, Gillespie D L, Silasi-Mansat R, Lupu F, Giles C B and Wren J D. ELTD1, a potential new biomarker for gliomas. Neurosurgery 2013; 72: 77-90; discussion 91.

[18] van Tellingen O, Yetkin-Arik B, de Gooijer M C, Wesseling P, Wurdinger T and de Vries H E. Overcoming the blood-brain tumor barrier for effective glioblastoma treatment. Drug Resist Updat 2015; 19: 1-12.

[19] Buss N A, Henderson S J, McFarlane M, Shenton J M and de Haan L. Monoclonal antibody therapeutics: history and future. Curr Opin Pharmacol 2012; 12: 615-622.

[20] Razpotnik R, Novak N, Curin Serbec V and Rajcevic U. Targeting Malignant Brain Tumors with Antibodies. Front Immunol 2017; 8: 1181.

[21] Lee Y, Kim H and Chung J. An antibody reactive to the Gly63-Lys68 epitope of NT-proBNP exhibits O-glycosylation-independent binding. Exp Mol Med 2014; 46: e114.

[22] Boussif O, Lezoualc'h F, Zanta M A, Mergny M D, Scherman D, Demeneix B and Behr J P. A versatile vector for gene and oligonucleotide transfer into cells in culture and in vivo: polyethylenimine. Proc Natl Acad Sci USA 1995; 92: 7297-7301.

[23] Andris-Widhopf J, Rader C, Steinberger P, Fuller R and Barbas C F, 3rd. Methods for the generation of chicken monoclonal antibody fragments by phage display. J Immunol Methods 2000; 242: 159-181.

[24] Barbas C F. Phage Display: A Laboratory Manual. Cold Spring Harbor Laboratory Press: Cold Spring Harbor, NY, 2001.

[25] Han J, Lee J H, Park S, Yoon S, Yoon A, Hwang D B, Lee H K, Kim M S, Lee Y, Yang W J, Youn H D, Kim H and Chung J. A phosphorylation pattern-recognizing antibody specifically reacts to RNA polymerase I I bound to exons. Exp Mol Med 2016; 48: e271.

[26] Ziegler J, Pody R, Coutinho de Souza P, Evans B, Saunders D, Smith N, Mallory S, Njoku C, Dong Y, Chen H, Dong J, Lerner M, Mian O, Tummala S, Battiste J, Fung K M, Wren J D and Towner R A. ELTD1, an effective anti-angiogenic target for gliomas: preclinical assessment in mouse GL261 and human G55 xenograft glioma models. Neuro Oncol 2017; 19: 175-185.

[27] Zhu W, Kato Y and Artemov D. Heterogeneity of tumor vasculature and antiangiogenic intervention: insights from MR angiography and DCE-MRI. PLoS One 2014; 9: e86583.

[28] Towner R A, Smith N, Doblas S, Garteiser P, Watanabe Y, He T, Saunders D, Herlea O, Silasi-Mansat R and Lupu F. In vivo detection of inducible nitric oxide synthase in rodent gliomas. Free Radic Biol Med 2010; 48: 691-703.

[29] Dafni H, Landsman L, Schechter B, Kohen F and Neeman M. MRI and fluorescence microscopy of the acute vascular response to VEGF165: vasodilation, hyper-permeability and lymphatic uptake, followed by rapid inactivation of the growth factor. NMR Biomed 2002; 15: 120-131.

[30] Hermanson G. Bioconjugate techniques. New York: Academic Press, 1996.

[31] Ziegler J, Zalles M, Smith N, Saunders D, Lerner M, Fung K M, Patel M, Wren J D, Lupu F, Battiste J and Towner R A. Targeting ELTD1, an angiogenesis marker for glioblastoma (GBM), also affects VEGFR2: molecular-targeted MRI assessment. Am J Nucl Med Mol Imaging 2019; 9: 93-109.

[32] Haacke E. Magnetic resonance imaging: physical principles and sequence design. New York: Wiley-Liss, 1999.
[33] Serban F, Daianu O, Tataranu L G, Artene S A, Emami G, Georgescu A M, Alexandru O, Purcaru S O, Tache D E, Danciulescu M M, Sfredel V and Dricu A. Silencing of epidermal growth factor, latrophilin and seven transmembrane domain-containing protein 1 (ELTD1) via siRNA-induced cell death in glioblastoma. J Immunoassay Immunochem 2017; 38: 21-33.
[34] Kuan C T, Srivastava N, McLendon R E, Marasco W A, Zalutsky M R and Bigner D D. Recombinant single-chain variable fragment antibodies against extracellular epitopes of human multidrug resistance protein MRP3 for targeting malignant gliomas. Int J Cancer 2010; 127: 598-611.
[35] Zhu X, Bidlingmaier S, Hashizume R, James C D, Berger M S and Liu B. Identification of internalizing human single-chain antibodies targeting brain tumor sphere cells. Mol Cancer Ther 2010; 9: 2131-2141.
[36] Patil S S, Railkar R, Swain M, Atreya H S, Dighe R R and Kondaiah P. Novel anti IGFBP2 single chain variable fragment inhibits glioma cell migration and invasion. J Neurooncol 2015; 123: 225-235.
[37] Lu Z, Kamat K, Johnson B P, Yin C C, Scholler N and Abbott K L. Generation of a Fully Human scFv that binds Tumor-Specific Glycoforms. Sci Rep 2019; 9: 5101.
[38] Mazzocco C, Fracasso G, Germain-Genevois C, Dugot-Senant N, Figini M, Colombatti M, Grenier N and Couillaud F. In vivo imaging of prostate cancer using an anti-PSMA scFv fragment as a probe. Sci Rep 2016; 6: 23314.
[39] Yang L, Mao H, Wang Y A, Cao Z, Peng X, Wang X, Duan H, Ni C, Yuan Q, Adams G, Smith M Q, Wood W C, Gao X and Nie S. Single chain epidermal growth factor receptor antibody conjugated nanoparticles for in vivo tumor targeting and imaging. Small 2009; 5: 235-243.
[40] Lariviere M, Lorenzato C S, Adumeau L, Bonnet S, Hemadou A, Jacobin-Valat M J, Noubhani A, Santarelli X, Minder L, Di Primo C, Sanchez S, Mornet S, Laroche-Traineau J and Clofent-Sanchez G. Multi-modal molecular imaging of atherosclerosis: Nanoparticles functionalized with scFv fragments of an anti-alphaIIbbeta3 antibody. Nanomedicine 2019; 22: 102082.

What is claimed is:

1. A pharmaceutical formulation comprising an anti-EGF, latrophilin and seven transmembrane domain-containing protein 1 (ELTD1) monoclonal antibody, or one or more anti-ELTD 1 monoclonal antibody fragments thereof, wherein the antibody or one or more antibody fragments thereof have light chain variable region complementarity determining regions (CDR) CDR1, CDR2, and CDR3 of SEQ ID NOS: 25, 26 and 27; 31, 32 and 33; 37, 38 and 39; 43, 44 and 45; 49, 50 and 51; 55, 56 and 57; 61, 62 and 63; 67, 68 and 69; 73, 74 and 75; 79, 80 and 81; 85, 86 and 87; 91, 92 and 93; 109, 110 and 111; 115, 116 and 117; 121, 122 and 123; or 127, 128 and 129, respectively; and the antibody has heavy chain variable regions CDR1, CDR2, and CDR3 of SEQ ID NOS: 28, 29 and 30; 88, 35 and 36; 40, 41 and 42; 46, 47 and 48; 58, 59 and 60; 64, 65 and 66; 70, 71 and 72; 76, 77 and 78; 82, 83 and 84; 88, 89 and 90; 94, 95 and 96; 100, 101 and 102; 106, 107 and 108; 112, 113 and 114; or 118, 119 and 120, respectively.

2. The pharmaceutical formulation of claim 1, wherein the antibody or one or more fragments thereof:

is an Fab fragment, F(ab')2 fragment, or Fv fragment;

is chimeric, humanized, or bispecific;

is a single chain fragment variable (scFv);

is a monovalent antibody;

comprises an Fc portion mutated to alter Fc Receptor (FcR) binding;

comprises an Fc portion mutated to increase half-life;

comprises an Fc portion mutated to alter antibody-dependent cellular cytotoxicity; or comprises an Fc portion mutated to alter complement activation.

3. The pharmaceutical formulation of claim 1, wherein at least one of the light chain variable regions and the heavy chain variable regions has the amino acid sequences of SEQ ID NOS: 2 and 4, 6 and 8, 10 and 12, 14 and 16, 18 and 20, or 22 and 24, respectively.

4. A method of treating a subject with cancer comprising administering to the subject with cancer a therapeutically effective amount of an anti-ELTD 1 monoclonal antibody or antibody fragment, wherein the cancer is glioma, glioblastoma, and/or glioblastoma multiforme, and wherein the monoclonal antibody or antibody fragment comprises light chain variable regions CDR1, CDR2, and CDR3 of SEQ ID NOS: 25, 26 and 27; 31, 32 and 33; 37, 38and 39; 43,38 and 45; 49, 50and 51; 55, 56 and 57; 61, 62 and 63; 67, 68 and 69; 73, 74 and 75; 79, 80 and 81; 85, 86 and 87; 91, 92 and 93; 109, 110 and 111; 115, 116 and 117; 121, 122 and 123; or 127, 128 and 129, respectively; and the antibody has heavy chain variable regions CDR1, CDR2, and CDR3 of SEQ ID NOS: 28, 29 and 30; 88, 35 and 36; 40, 41 and 42; 46, 47 and 48; 58, 59 and 60; 64, 65 and 66; 70, 71 and 72; 76, 77 and 78; 82, 83 and 84; 88, 89 and 90; 94, 95 and 96; 100, 101 and 102; 106, 107 and 108; 112, 113 and 114; or 118, 119 and 120, respectively.

5. The method of claim 4, wherein the monoclonal antibody or antibody fragment:
- is an Fab fragment, F(ab')2 fragment, or Fv fragment;
- is chimeric, humanized, or bispecific;
- is a single chain fragment variable (scFv);
- is a monovalent antibody;
- comprises an Fc portion mutated to alter Fc Receptor (FcR) binding;
- comprises an Fc portion mutated to increase half-life;
- comprises an Fc portion mutated to alter antibody-dependent cellular cytotoxicity; or
- comprises an Fc portion mutated to alter complement activation.

6. The method of claim 4, wherein the antibody light chain variable region and heavy chain variable region have the amino acid sequences of SEQ ID NOS: 2 and 4, 6 and 8, 10 and 12, 14 and 16, 18 and 20, or 22 and 24, respectively.

7. The method of claim 4, wherein the glioma, glioblastoma, and/or glioblastoma multiforme is metastatic or recurrent.

8. The method of claim 4, further comprising treating the subject with a second cancer therapy selected from radiation, chemotherapy, immunotherapy, toxin therapy or surgery.

9. The method of claim 4, wherein the subject shows reduced or no hemorrhage during administration.

10. A monoclonal antibody or fragment thereof that binds specifically to ELTD1 comprising a light chain variable region and a heavy chain variable region with an amino acid sequences of SEQ ID NOS: 2 and 4, 6 and 8, 10 and 12, 14 and 16, 18 and 20, or 22 and 24, respectively.

11. The monoclonal antibody of claim 10, wherein the antibody or fragment thereof:
- is an Fab fragment, F(ab')2 fragment, or Fv fragment;
- is chimeric, humanized, or bispecific;
- is a single chain fragment variable (scFv);
- is a monovalent antibody;
- comprises an Fc portion mutated to alter Fc Receptor (FcR) binding;
- comprises an Fc portion mutated to increase half-life;
- comprises an Fc portion mutated to alter antibody-dependent cellular cytotoxicity; or
- comprises an Fc portion mutated to alter complement activation.

12. A method of treating a cancer with an anti-EGF, latrophilin and seven transmembrane domain-containing protein 1 (ELTD1) antibody or fragment thereof in a subject comprising:
- identifying a subject with cancer; and
- administering to the subject with cancer a therapeutically effective amount of the anti-ELTD 1 antibody or fragment thereof sufficient to reduce the symptoms from or treat the cancer, wherein the cancer is glioma, glioblastoma, and/or glioblastoma multiforme, and wherein the antibody or fragment thereof has light chain variable regions CDR1, CDR2, and CDR3 of SEQ ID NOS: 25, 26 and 27; 31, 32 and 33; 37, 38 and 39; 43, 38 and 45; 49, 50 and 51; 55, 56 and 57; 61, 62 and 63; 67, 68 and 69; 73, 74 and 75; 79, 80 and 81; 85, 86 and 87; 91, 92 and 93; 109, 110 and 111; 115, 116 and 117; 121, 122 and 123; or 127, 128 and 129, respectively; and the monoclonal antibody has heavy chain variable regions CDR1, CDR2, and CDR3 of SEQ ID NOS: 28, 29 and 30; 88, 35 and 36; 40, 41 and 42; 46, 47 and 48; 58, 59 and 60; 64, 65 and 66; 70, 71 and 72; 76, 77 and 78; 82, 83 and 84; 88, 89 and 90; 94, 95 and 96; 100, 101 and 102; 106, 107 and 108; 112, 113 and 114; or 118, 119 and 120, respectively.

* * * * *